US010829798B2

(12) United States Patent
Anderson et al.

(10) Patent No.: US 10,829,798 B2
(45) Date of Patent: Nov. 10, 2020

(54) DNA-LINKED ENZYME-COUPLED ASSAYS

(71) Applicants: THE REGENTS OF THE UNIVERSITY OF CALIFORNIA, Oakland, CA (US); David J. Sukovich, San Francisco, CA (US); Cyrus Modavi, Kensington, CA (US)

(72) Inventors: John Christopher Anderson, Berkeley, CA (US); David J. Sukovich, San Francisco, CA (US); Cyrus Modavi, Kensington, CA (US); Markus De Raad, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 65 days.

(21) Appl. No.: 15/514,777

(22) PCT Filed: Sep. 29, 2015

(86) PCT No.: PCT/US2015/052920
§ 371 (c)(1),
(2) Date: Mar. 27, 2017

(87) PCT Pub. No.: WO2016/054024
PCT Pub. Date: Apr. 7, 2016

(65) Prior Publication Data
US 2017/0240952 A1    Aug. 24, 2017

Related U.S. Application Data

(60) Provisional application No. 62/057,123, filed on Sep. 29, 2014.

(51) Int. Cl.
*C12P 19/34* (2006.01)
*C12Q 1/48* (2006.01)
*G01N 33/542* (2006.01)

(52) U.S. Cl.
CPC ............ *C12Q 1/48* (2013.01); *G01N 33/542* (2013.01); *G01N 2333/91091* (2013.01)

(58) Field of Classification Search
CPC ........... C12Q 1/48; G01N 2333/91091; G01N 33/542
See application file for complete search history.

(56) References Cited

U.S. PATENT DOCUMENTS

2002/0155489 A1   10/2002  Short
2005/0118665 A1    6/2005  Zhou et al.

FOREIGN PATENT DOCUMENTS

WO    WO 2000/050630    8/2000

OTHER PUBLICATIONS

Robertson et al., Nucleic acids Research, vol. 39, No. 8, e55, pp. 1-10, (Year: 2011).*
Morera et al., J. Mol. Biol. 292, 717-730 (1999).
Terragni et al., Biochemistry, 51, 1009-1019 (2012).

* cited by examiner

*Primary Examiner* — Cynthia B Wilder
(74) *Attorney, Agent, or Firm* — Morgan, Lewis & Bockius LLP; Jeffry S. Mann; Todd Esker

(57) ABSTRACT

Traditional enzyme characterization methods are low-throughput, and therefore limit engineering efforts in synthetic biology and biotechnology. Here we propose a DNA-linked enzyme-coupled assay (DLEnCA) to monitor enzyme reactions in a high-throughput manner. Throughput is improved by removing the need for protein purification and by limiting the need for liquid chromatography mass spectrometry (LCMS) product detection by linking enzymatic function to DNA modification. DLEnCA is generalizable for many enzymatic reactions, and here we adapt it for glucosyltransferases, methyltransferases, and oxidoreductases. The assay utilizes cell free transcription/translation systems to produce enzymes of interest, while UDP-Glucose and T4-β-glucosyltransferase are used to modify DNA, which is detected post-reaction using qPCR or similar means of DNA analysis. For monitoring methyltransferases, consumption of SAM is observed by coupling to EcoRI methyltransferase. For monitoring oxidoreductases, consumption of NADH is observed by coupling to Taq or *E. coli* DNA ligase. OleD and two glucosyltransferases from *Arabidopsis* were used to verify the assay's generality toward glucosyltransferases. Two methyltransferases from human and *Arabidopsis* were used to verify the assay's generality towards methyltransferases. We show DLEnCA's utility by mapping out the substrate specificity for these enzymes and observing the multiple steps of a biosynthetic pathway.

14 Claims, 36 Drawing Sheets
Specification includes a Sequence Listing.

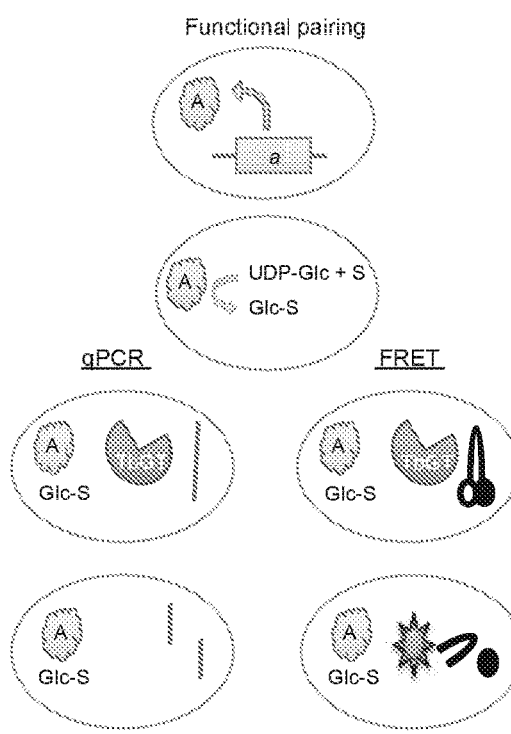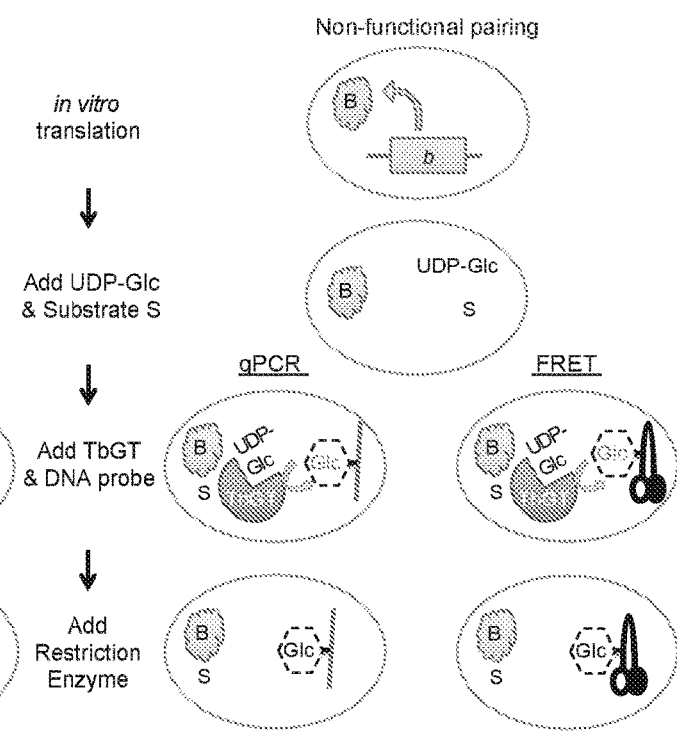
FIG. 1A Functional pairing
FIG. 1B Non-functional pairing

FIG. 21

| Primer | Sequence | Used for |
| --- | --- | --- |
| P01 | AGAAATAATTTTGTTTAACTTTAAGAAGGAGATATACCATGGCTACCACCCAGACCACTC | To make OleD |
| P02 | TTCCTTTCGGGCTTTGTTAGCAGCCGGATCTCAGTCGACGGCGCTATTCAGATCCTCTTC | |
| P03 | GAAGAGGATCTGAATAGCGCCGTCGACTGAGATCCGGCTGCTAACAAAGCCCGAAAGGAA | To make backbone |
| P04 | GAGTGGTCTGGGTGGTAGCCATGGTATATCTCCTTCTTAAAGTTAAACAAAATTATTTCT | |
| P05 | ATACCATGGAGGAATCCAAAACACCTCACGTTG | To make GT05 |
| P06 | ATTAGATCTTAGTGGTTGCCATTTTGCTCTAACTCTTTTTTGTG | |
| P07 | ATAAGGTCTCACATGAAAGTGAACGAGGAAAACAACAAGC | To make GT06 |
| P08 | ACACGGTCTCAGATCTCATTTGTTTAGTCCTAAACTAACGACATGTTGG | |
| P09 | GATGCGTCCGGCGTAGAGGATCGAG | To make linear DNA |
| P10 | TTGCTAACGCAGTCAGGCACCGTGTATG | |
| P11 | GCTGAAGCGCAAAATGATCCCTG | To make probe |
| P12 | TGACAACTTGACGGCTACATCATTCACTTTTTCT | |
| Fluorescent Probe | /5Cy3/GACC/i5HydMe-dC/AATTGCGATTCCGTCTCCGGAATCG/i5HydMe-dC/AATTGGGTC/3BHQ_2/ | Fluorescent probe |

FIG. 22

OleD - DQ195536:

ATGGCTACCACCCAGACCACTCCCGCCCACATCGCCATGTTCTCCATCGCC
GCCCACGGCCATGTGAACCCCAGCCTGGAGGTGATCCGTGAACTCGTCGC
CCGCGGCCACCGGGTCACGTACGCCATTCCGCCCGTCTTCGCCGACAAGG
TGGCCGCCACCGGCGCCCGGCCCGTCCTCTACCACTCCACCCTGCCCGGC
CCCGACGCCGACCCGGAGGCATGGGGAAGCACCTGCTGGACAACGTCG
AACCGTTCCTGAACGACGCGATCCAGGCGCTCCCGCAGCTCGCCGATGCC
TACGCCGACGACATCCCCGATCTCGTCCTGCACGACATCACCTCCTACCCG
GCCCGCGTCCTGGCCCGCCGCTGGGGCGTCCCGGCGGTCTCCCTCTCCC
CGAACCTCGTCGCCTGGAAGGGTTACGAGGAGGAGGTCGCCGAGCCGATG
TGGCGCGAACCCCGGCAGACCGAGCGCGGACGGGCCTACTACGCCCGGT
TCGAGGCATGGCTGAAGGAGAACGGGATCACCGAGCACCCGGACACGTTC
GCCAGTCATCCGCCGCGCTCCCTGGTGCTCATCCCGAAGGCGCTCCAGCC
GCACGCCGACCGGGTGGACGAAGACGTGTACACCTTCGTCGGCGCCTGCC
AGGGAGACCGCGCCGAGGAAGGCGGCTGGCAGCGGCCCGCCGGCGCGG
AGAAGGTCGTCCTGGTGTCGCTCGGCTCGGCGTTCACCAAGCAGCCCGCC
TTCTACCGGGAGTGCGTGCGCGCCTTCGGGAACCTGCCCGGCTGGCACCT
CGTCCTCCAGATCGGCCGGAAGGTGACCCCGCCGAACTGGGGGAGCTG
CCGGACAACGTGGAGGTGCACGACTGGGTGCCGCAGCTCGCGATCCTGCG
CCAGGCCGATCTGTTCGTCACCCACGCGGGCGCCGGCGGCAGCCAGGAG
GGGCTGGCCACCGCGACGCCCATGATCGCCGTACCGCAGGCCGTCGACC
AGTTCGGCAACGCCGACATGCTCCAAGGGCTCGGCGTCGCCGGAAGCTG
GCGACCGAGGAGGCCACCGCCGACCTGCTCCGCGAGACCGCCCTCGCTC
TGGTGGACGACCCGGAGGTCGCGCGCCGGCTCCGGCGAATCCAGGCGGA
GATGGCCCAGGAGGGCGGCACCCGGCGGGCGGCCGACCTCATCGAGGCC
GAACTGCCCGCGCCACGAGCGGCAGGAGCCGGTGGGCGACCGACCCA
ACGGTGGGGGGAATTCGAAGCTTGGGCCCGAACAAAAACTCATCTCAGAAG
AGGATCTGAATAGCGCCGTCGAC

FIG. 23

GT05 - UGT72B1 (Q9M156)

ATGGAGGAATCCAAAACACCTCACGTTGCGATCATACCAAGTCCGGGAATG
GGTCATCTCATACCACTCGTCGAGTTTGCTAAACGACTCGTCCATCTTCACG
GCCTCACCGTTACCTTCGTCATCGCCGGCGAAGGTCCACCATCAAAAGCTC
AGAGAACCGTCCTCGACTCTCTCCCTTCTTCAATCTCCTCCGTCTTTCTCCC
TCCTGTTGATCTCACCGATCTCTCTTCGTCCACTCGCATCGAATCTCGGATC
TCCCTCACCGTGACTCGTTCAAACCCGGAGCTCCGGAAAGTCTTCGACTCG
TTCGTGGAGGGAGGTCGTTTGCCAACGGCGCTCGTCGTCGATCTCTTCGGT
ACGGACGCTTTCGACGTGGCCGTAGAATTTCACGTGCCACCGTATATTTTCT
ACCCAACAACGGCCAACGTCTTGTCGTTTTTCTCCATTTGCCTAAACTAGA
CGAAACGGTGTCGTGTGAGTTCAGGGAATTAACCGAACCGCTTATGCTTCC
TGGATGTGTACCGGTTGCCGGGAAAGATTTCCTTGACCCGGCCCAAGACCG
GAAAGACGATGCATACAAATGGCTTCTCCATAACACCAAGAGGTACAAAGAA
GCCGAAGGTATTCTTGTGAATACCTTCTTTGAGCTAGAGCCAAATGCTATAA
AGGCCTTGCAAGAACCGGGTCTTGATAAACCACCGGTTTATCCGGTTGGAC
CGTTGGTTAACATTGGTAAGCAAGAGGCTAAGCAAACCGAAGAGTCTGAAT
GTTAAAGTGGTTGGATAACCAGCCGCTCGGTTCGGTTTTATATGTGTCCTT
TGGTAGTGGCGGTACCCTCACATGTGAGCAGCTCAATGAGCTTGCTCTTGG
TCTTGCAGATAGTGAGCAACGGTTTCTTTGGGTCATACGAAGTCCTAGTGG
GATCGCTAATTCGTCGTATTTTGATTCACATAGCCAAACAGATCCATTGACAT
TTTTACCACCGGGATTTTTAGAGCGGACTAAAAAAGAGGTTTTGTGATCCC
TTTTTGGGCTCCACAAGCCCAAGTCTTGGCGCATCCATCCACGGGAGGATT
TTTAACTCATTGTGGATGGAATTCGACTCTAGAGAGTGTAGTAAGCGGTATT
CCACTTATAGCATGGCCATTATACGCAGAACAGAAGATGAATGCGGTTTGT
TGAGTGAAGATATTCGTGCGGCACTTAGGCCGCGTGCCGGGGACGATGGG
TTAGTTAGAAGAGAAGAGGTGGCTAGAGTGGTAAAAGGATTGATGGAAGGT
GAAGAAGGCAAAGGAGTGAGGAACAAGATGAAGGAGTTGAAGGAAGCAGC
TTGTAGGGTGTTGAAGGATGATGGACTTCGACAAAGCACTTAGTCTTGT
GGCCTTAAAGTGGAAAGCCCACAAAAAGAGTTAGAGCAAAATGGCAACCA
CTAA

FIG. 24

GT06 - UGT89B1 (AT1G73880)

ATGAAAGTGAACGAGGAAAACAACAAGCCGACAAAGACCCATGTCTTAATCT
TCCCATTTCCGGCGCAAGGTCACATGATTCCCCTCCTCGACTTCACCCACC
GCCTTGCTCTCCGCGGCGGCGCCGCCTTAAAAATAACCGTCCTAGTCACTC
CAAAAAACCTTCCTTTTCTCTCTCCGCTTCTCTCCGCCGTAGTTAACATCGAA
CCACTTATCCTCCCTTTTCCCTCCCACCCTTCAATCCCCTCCGGCGTCGAAA
ACGTCCAAGACTTACCTCCTTCAGGCTTCCCTTTAATGATCCACGCGCTTGG
TAATCTCCACGCGCCGCTTATCTCTTGGATTACTTCTCACCCTTCTCCTCCA
GTAGCCATCGTATCTGATTTCTTCCTTGGTTGGACCAAAAACCTCGGAATCC
CTCGTTTCGATTTCTCTCCCTCCGCTGCTATCACTTGCTGCATACTCAATACT
CTCTGGATCGAAATGCCCACCAAGATCAACGAAGATGACGATAACGAGATC
CTCCACTTTCCCAAGATCCCGAATTGTCCAAAATACCGTTTTGATCAGATCT
CCTCTCTTTACAGAAGTTACGTTCACGGAGATCCAGCTTGGGAGTTCATAAG
AGACTCCTTTAGAGATAACGTGGCGAGTTGGGGACTCGTCGTGAACTCGTT
CACCGCCATGGAAGGTGTTTATCTCGAACATCTTAAGCGAGAGATGGGCCA
TGATCGTGTATGGGCTGTAGGCCCAATTATTCCGTTATCTGGGGATAACCGT
GGTGGCCCGACTTCTGTTTCTGTTGATCACGTGATGTCGTGGCTTGACGCA
CGTGAGGATAACCACGTGGTGTACGTGTGCTTTGGAAGTCAAGTAGTTTTG
ACTAAAGAGCAGACTCTTGCACTCGCCTCTGGGCTTGAGAAAGCGGCGTC
CATTTCATATGGGCCGTAAGGAGCCCGTTGAGAAAGACTCAACACGTGGC
AACATCCTGGACGGTTTCGACGATCGCGTGGCTGGGAGAGGTCTGGTGAT
CAGAGGATGGGCTCCACAAGTAGCTGTGCTACGTCACCGAGCCGTTGGCG
CGTTTTAACGCACTGTGGTTGGAACTCTGTGGTGGAGGCGGTTGTCGCCG
GCGTTTGATGCTGACGTGGCCGATGAGAGCTGACCAGTACACTGACGCGT
CTCTGGTGGTTGATGAGTTGAAAGTAGGTGTGCGTGCTTGCGAAGGACCTG
ACACGGTGCCTGACCCGGACGAGTTAGCTCGAGTTTTCGCTGATTCCGTGA
CCGGAAATCAAACGGAGAGGATCAAAGCCGTGGAGCTGAGGAAAGCAGCG
TTGGATGCGATTCAAGAACGTGGGAGCTCAGTGAATGATTTAGATGGATTTA
TCCAACATGTCGTTAGTTTAGGACTAAACAAATGA

FIG. 25

"Probe" DNA (araC):

GCTGAAGCGCAAAATGATCCCCTGCTGCCGGGATACTCGTTTAATGCCCAT
CTGGTGGCGGGTTTAACGCCGATTGAGGCCAACGGTTATCTCGATTTTTTA
TCGACCGACCGCTGGGAATGAAAGGTTATATTCTCAATCTCACCATTCGCG
GTCAGGGGTGGTGAAAATCAGGGACGAGAATTTGTTTGCCGACCGGGT
GATATTTTGCTGTTCCGCCAGGAGAGATTCATCACTACGGTCGTCATCCG
GAGGCTCGCGAATGGTATCACCAGTGGGTTTACTTTCGTCCGCGCGCCTAC
TGGCATGAATGGCTTAACTGGCCGTCAATATTTGCCAATACGGGGTTCTTTC
GCCCGGATGAAGCGCACCAGCCGCATTTCAGCGACCTGTTTGGGCAAATCA
TTAACGCCGGGCAAGGGGAAGGGCGCTATTCGGAGCTGCTGGCGATAAAT
CTGCTTGAGCAATTGTTACTGCGGCGCATGGAAGCGATTAACGAGTCGCTC
CATCCACCGATGGATAATCGGGTACGCGAGGCTTGTCAGTACATCAGCGAT
CACCTGGCAGACAGCAATTTTGATATCGCCAGCGTCGCACAGCATGTTTGC
TTGTCGCCGTCGCGTCTGTCACATCTTTTCCGCCAGCAGTTAGGGATTAGC
GTCTTAAGCTGGCGCGAGGACCAACGTATCAGCCAGGCGAAGCTGCTTTTG
AGCACCACCCGGATGCCTATCGCCACCGTCGGTCGCAATGTTGGTTTTGAC
GATCAACTCTATTTCTCGCGGGTATTTAAAAAATGCACCGGGGCCAGCCCG
AGCGAGTTCCGTGCCGGTTGTGAAGAAAAGTGAATGATGTAGCCGTCAAG
TTGTCA

SEQUENCE LISTING

<160> NUMBER OF SEQ ID NOS: 17

<210> SEQ ID NO 1
<211> LENGTH: 60
<212> TYPE: DNA
<213> ORGANISM: Artificial Sequence
<220> FEATURE:
<223> OTHER INFORMATION: Primer 01 to make OleD

<400> SEQUENCE: 1
agaaataatt tgtttaact ttaagaagga gatataccat ggctaccacc cagaccactc    60

<210> SEQ ID NO 2
<211> LENGTH: 60
<212> TYPE: DNA
<213> ORGANISM: Artificial Sequence
<220> FEATURE:
<223> OTHER INFORMATION: Primer 02 to make OleD

<400> SEQUENCE: 2
ttcctttcgg gctttgttag cagccggatc tcagtcgacg gcgctattca gatcctcttc    60

<210> SEQ ID NO 3
<211> LENGTH: 60
<212> TYPE: DNA
<213> ORGANISM: Artificial Sequence
<220> FEATURE:
<223> OTHER INFORMATION: Primer 03 to make backbone

<400> SEQUENCE: 3
gaagaggatc tgaatagcgc cgtcgactga gatccggctg ctaacaaagc ccgaaggaa    60

<210> SEQ ID NO 4
<211> LENGTH: 60
<212> TYPE: DNA
<213> ORGANISM: Artificial Sequence
<220> FEATURE:
<223> OTHER INFORMATION: Primer 04 to make backbone

<400> SEQUENCE: 4
gagtggtctg ggtggtagcc atggtatatc tccttcttaa agttaaacaa aattatttct    60

<210> SEQ ID NO 5
<211> LENGTH: 33
<212> TYPE: DNA
<213> ORGANISM: Artificial Sequence
<220> FEATURE:
<223> OTHER INFORMATION: P06 to make GT05

<400> SEQUENCE: 5
ataccatgga ggaatccaaa acacctcacg ttg    33

<210> SEQ ID NO 6
<211> LENGTH: 45
<212> TYPE: DNA
<213> ORGANISM: Artificial Sequence
<220> FEATURE:
<223> OTHER INFORMATION: Primer 06 to make GT05

<400> SEQUENCE: 6
attagatctt tagtggttgc cattttgctc taactctttt ttgtg    45

<210> SEQ ID NO 7
<211> LENGTH: 40
<212> TYPE: DNA
<213> ORGANISM: Artificial Sequence

```
<220> FEATURE:
<223> OTHER INFORMATION: Primer 07 to make GT06

<400> SEQUENCE: 7
ataaggtctc acatgaaagt gaacgaggaa aacaacaagc                              40

<210> SEQ ID NO 8
<211> LENGTH: 49
<212> TYPE: DNA
<213> ORGANISM: Artificial Sequence
<220> FEATURE:
<223> OTHER INFORMATION: Primer 08 to make GT06

<400> SEQUENCE: 8
acacggtctc agatctcatt tgtttagtcc taaactaacg acatgttgg                    49

<210> SEQ ID NO 9
<211> LENGTH: 25
<212> TYPE: DNA
<213> ORGANISM: Artificial Sequence
<220> FEATURE:
<223> OTHER INFORMATION: Primer 09 to make linear DNA

<400> SEQUENCE: 9
gatgcgtccg gcgtagagga tcgag                                              25

<210> SEQ ID NO 10
<211> LENGTH: 28
<212> TYPE: DNA
<213> ORGANISM: Artificial Sequence
<220> FEATURE:
<223> OTHER INFORMATION: Primer 10 to make linear DNA

<400> SEQUENCE: 10
ttgctaacgc agtcaggcac cgtgtatg                                           28

<210> SEQ ID NO 11
<211> LENGTH: 24
<212> TYPE: DNA
<213> ORGANISM: Artificial Sequence
<220> FEATURE:
<223> OTHER INFORMATION: Primer 11 to make probe

<400> SEQUENCE: 11
gctgaagcgc aaaatgatcc cctg                                               24

<210> SEQ ID NO 12
<211> LENGTH: 34
<212> TYPE: DNA
<213> ORGANISM: Artificial Sequence
<220> FEATURE:
<223> OTHER INFORMATION: Primer 12 to make probe

<400> SEQUENCE: 12
tgacaacttg acggctacat cattcacttt ttct                                    34

<210> SEQ ID NO 13
<211> LENGTH: 38
<212> TYPE: DNA
<213> ORGANISM: Artificial Sequence
<220> FEATURE:
<223> OTHER INFORMATION: Fluorescent probe

<400> SEQUENCE: 13
gaccaattgc gattccgtct ccggaatcga attgggtc                                38
```

<210> SEQ ID NO 14
<211> LENGTH: 1314
<212> TYPE: DNA
<213> ORGANISM: Artificial Sequence
<220> FEATURE:
<223> OTHER INFORMATION: OleD - DQ195536

<400> SEQUENCE: 14

```
atggctacca cccagaccac tcccgcccac atcgccatgt tctccatcgc cgcccacggc      60
catgtgaacc ccagcctgga ggtgatccgt gaactcgtcg cccgcggcca ccgggtcacg     120
tacgccattc cgccgtcttc cgccgacaag gtggccgcca ccggcgcccg gcccgtcctc     180
taccactcca ccctgcccgg ccccgacgcc gacccgaggc atggggaagc accctgctg      240
gacaacgtcg aaccgttcct gaacgacgcg atccaggcgc tcccgcagct cgccgatgcc     300
tacgccgacg acatccccga tctcgtcctg cacgacatca cctcctaccc ggcccgcgtc     360
ctggcccgcc gctggggcgt cccggcggtc tccctctccc cgaacctcgt cgcctggaag     420
ggttacgagg aggaggtcgc cgagccgatg tggcgcgaac cccggcagac cgagcgcgga     480
cgggcctact acgcccggtt cgaggcatgg ctgaaggaga acgggatcac cgagcacccg     540
gacacgttcg ccagtcatcc gccgcgctcc ctggtgctca tcccgaaggc gctccagccg     600
cacgccgacc gggtggacga agacgtgtac accttcgtcg gcgcctgcca gggagaccgc     660
gccgaggaag gcggctggca gcggcccgcc ggcgcggaga aggtcgtcct ggtgtcgctc     720
ggctcggcgt tcaccaagca gcccgccttc taccgggagt gcgtgcgcgc cttcgggaac     780
ctgcccggct ggcacctcgt cctccagatc ggccggaagg tgaccccccgc cgaactgggg     840
gagctgccgg acaacgtgga ggtgcacgac tgggtgccgc agctcgcgat cctgcgccag     900
gccgatctgt tcgtcaccca cgcgggcgcc ggcggcagcc aggaggggct ggccaccgcg     960
acgcccatga tcgccgtacc gcaggccgtc gaccagttcg gcaacgccga catgctccaa    1020
gggctcggcg tcgcccggaa gctggcgacc gaggaggcca ccgccgacct gctccgcgag    1080
accgccctcg ctctggtgga cgacccggag gtcgcgcgcc ggctccggcg aatccaggcg    1140
gagatggccc aggagggcgg caccggcgg gcggccgacc tcatcgaggc cgaactgccc    1200
gcgcgccacg agcggcagga gccggtgggc gaccgaccca acgtggggg gaattcgaag    1260
cttgggcccg aacaaaaact catctcagaa gaggatctga atagcgccgt cgac          1314
```

<210> SEQ ID NO 15
<211> LENGTH: 1443
<212> TYPE: DNA
<213> ORGANISM: Artificial Sequence
<220> FEATURE:
<223> OTHER INFORMATION: GT05- UGT7281(Q9M156)

<400> SEQUENCE: 15

```
atggaggaat ccaaaacacc tcacgttgcg atcataccaa gtccgggaat gggtcatctc      60
ataccactcg tcgagtttgc taaacgactc gtccatcttc acggcctcac cgttaccttc     120
gtcatcgccg gcgaaggtcc accatcaaaa gctcagagaa ccgtcctcga ctctctccct     180
tcttcaatct cctccgtctt tctccctcct gttgatctca ccgatctctc ttcgtccact     240
cgcatcgaat ctcggatctc cctcaccgtg actcgttcaa acccggagct ccggaaagtc     300
ttcgactcgt tcgtggaggg aggtcgtttg ccaacggcgc tcgtcgtcga tctcttcggt     360
acggacgctt tcgacgtggc cgtagaattt cacgtgccac cgtatatttt ctacccaaca     420
acggccaacg tcttgtcgtt ttttctccat ttgcctaaac tagacgaaac ggtgtcgtgt    480
```

| | |
|---|---:|
| gagttcaggg aattaaccga accgcttatg cttcctggat gtgtaccggt tgccgggaaa | 540 |
| gatttccttg acccgccca agaccggaaa gacgatgcat acaaatggct tctccataac | 600 |
| accaagaggt acaaagaagc cgaaggtatt cttgtgaata ccttctttga gctagagcca | 660 |
| aatgctataa aggccttgca agaaccgggt cttgataaac caccggttta tccggttgga | 720 |
| ccgttggtta acattggtaa gcaagaggct aagcaaaccg aagagtctga atgtttaaag | 780 |
| tggttggata ccagccgct cggttcggtt ttatatgtgt cctttggtag tggcggtacc | 840 |
| ctcacatgtg agcagctcaa tgagcttgct cttggtcttg cagatagtga gcaacggttt | 900 |
| cttttgggtca tacgaagtcc tagtgggatc gctaattcgt cgtattttga ttcacatagc | 960 |
| caaacagatc cattgacatt tttaccaccg ggatttttag agcggactaa aaaaagaggt | 1020 |
| tttgtgatcc cttttggc tccacaagcc caagtcttgg cgcatccatc acgggagga | 1080 |
| tttttaactc attgtggatg gaattcgact ctagagagtg tagtaagcgg tattccactt | 1140 |
| atagcatggc cattatacgc agaacagaag atgaatgcgg ttttgttgag tgaagatatt | 1200 |
| cgtgcggcac ttaggccgcg tgccgggac gatgggttag ttagaagaga agaggtggct | 1260 |
| agagtggtaa aaggattgat ggaaggtgaa aaggcaaag gagtgaggaa caagatgaag | 1320 |
| gagttgaagg aagcagcttg tagggtgttg aaggatgatg ggacttcgac aaaagcactt | 1380 |
| agtcttgtgg ccttaaagtg gaaagcccac aaaaagagt tagagcaaaa tggcaaccac | 1440 |
| taa | 1443 |

<210> SEQ ID NO 16
<211> LENGTH: 1422
<212> TYPE: DNA
<213> ORGANISM: Artificial Sequence
<220> FEATURE:
<223> OTHER INFORMATION: GT06- UGT89B1(AT1G73880)

<400> SEQUENCE: 16

| | |
|---|---:|
| atgaaagtga acgaggaaaa caacaagccg acaaagaccc atgtcttaat cttcccattt | 60 |
| ccggcgcaag gtcacatgat tcccctcctc gacttcaccc accgccttgc tctccgcggc | 120 |
| ggcgccgcct taaaaataac cgtcctagtc actccaaaaa accttccttt tctctctccg | 180 |
| cttctctccg ccgtagttaa catcgaacca cttatcctcc cttttccctc ccacccttca | 240 |
| atcccctccg gcgtcgaaaa cgtccaagac ttacctcctt caggcttccc tttaatgatc | 300 |
| cacgcgcttg gtaatctcca cgcgccgctt atctcttgga ttacttctca cccttctcct | 360 |
| ccagtagcca tcgtatctga tttcttcctt ggttggacca aaaacctcgg aatccctcgt | 420 |
| ttcgatttct ctccctccgc tgctatcact tgctgcatac tcaatactct ctggatcgaa | 480 |
| atgcccacca agatcaacga agatgacgat aacgagatcc tccactttcc caagatcccg | 540 |
| aattgtccaa ataccgtttt tgatcagatc tcctctcttt acagaagtta cgttcacgga | 600 |
| gatccagctt gggagttcat aagagactcc tttagagata cgtggcgag ttggggactc | 660 |
| gtcgtgaact cgttcaccgc catggaaggt gtttatctcg aacatcttaa gcgagagatg | 720 |
| ggccatgatc gtgtatgggc tgtaggccca attattccgt tatctgggga taaccgtggt | 780 |
| ggcccgactt ctgtttctgt tgatcacgtg atgtcgtggc ttgacgcacg tgaggataac | 840 |
| cacgtggtgt acgtgtgctt tggaagtcaa gtagttttga ctaaagagca gactcttgca | 900 |
| ctcgcctctg ggcttgagaa aagcggcgtc catttcatat gggccgtaaa ggagcccgtt | 960 |
| gagaaagact caacacgtgg caacatcctg acggttttcg acgatcgcgt ggctgggaga | 1020 |
| ggtctggtga tcagaggatg ggctccacaa gtagctgtgc tacgtcaccg agccgttggc | 1080 |

-continued

```
gcgtttttaa cgcactgtgg ttggaactct gtggtggagg cggttgtcgc cggcgttttg    1140
atgctgacgt ggccgatgag agctgaccag tacactgacg cgtctctggt ggttgatgag    1200
ttgaaagtag gtgtgcgtgc ttgcgaagga cctgacacgg tgcctgaccc ggacgagtta    1260
gctcgagttt tcgctgattc cgtgaccgga aatcaaacgg agaggatcaa agccgtggag    1320
ctgaggaaag cagcgttgga tgcgattcaa gaacgtggga gctcagtgaa tgatttagat    1380
ggatttatcc aacatgtcgt tagtttagga ctaaacaaat ga                       1422
```

<210> SEQ ID NO 17
<211> LENGTH: 873
<212> TYPE: DNA
<213> ORGANISM: Artificial Sequence
<220> FEATURE:
<223> OTHER INFORMATION: "Probe" DNA (araC)

<400> SEQUENCE: 17

```
gctgaagcgc aaaatgatcc cctgctgccg ggatactcgt ttaatgccca tctggtggcg      60
ggtttaacgc cgattgaggc caacggttat ctcgattttt ttatcgaccg accgctggga     120
atgaaaggtt atattctcaa tctcaccatt cgcggtcagg gggtggtgaa aaatcaggga     180
cgagaatttg tttgccgacc gggtgatatt ttgctgttcc cgccaggaga gattcatcac     240
tacggtcgtc atccggaggc tcgcgaatgg tatcaccagt gggtttactt tcgtccgcgc     300
gcctactggc atgaatggct taactggccg tcaatatttg ccaatacggg gttctttcgc     360
ccggatgaag cgcaccagcc gcatttcagc gacctgtttg ggcaaatcat taacgccggg     420
caaggggaag ggcgctattc ggagctgctg gcgataaatc tgcttgagca attgttactg     480
cggcgcatgg aagcgattaa cgagtcgctc catccaccga tggataatcg ggtacgcgag     540
gcttgtcagt acatcagcga tcacctggca gacagcaatt ttgatatcgc cagcgtcgca     600
cagcatgttt gcttgtcgcc gtcgcgtctg tcacatcttt tccgccagca gttagggatt     660
agcgtcttaa gctggcgcga ggaccaacgt atcagccagg cgaagctgct tttgagcacc     720
acccggatgc ctatcgccac cgtcggtcgc aatgttggtt ttgacgatca actctatttc     780
tcgcgggtat ttaaaaaatg caccggggcc agcccgagcg agttccgtgc cggttgtgaa     840
gaaaaagtga atgatgtagc cgtcaagttg tca                                  873
```

DNA-LINKED ENZYME-COUPLED ASSAYS

CROSS-REFERENCE TO RELATED APPLICATIONS

This application is a 371 U.S. National Phase application of PCT International Application No. PCT/US2015/052920 filed Sep. 29, 2015 which claims the benefit under 35 U.S.C. § 119(e) of U.S. Provisional Application No. 62/057,123 filed on Sep. 29, 2014, both of which are incorporated herein by reference in their entireties for all purposes.

FIELD OF THE INVENTION

The present invention provides methods of monitoring enzyme reactions by detecting enzymatic modification of nucleic acids.

BACKGROUND OF THE INVENTION

Enzymatic biochemical reactions have been studied for decades, as they are responsible for the thousands of metabolic processes required for life. With the rise of biotechnology, synthetic biology, and metabolic engineering, enzymes are increasingly viewed as tools to catalyze a desired chemical reaction (Kim, et al., (2007) *J. Microb. Biotechnol.* 17, 116-122; Williams, et al., (2007) *Nat Chem Biol.* 3, 657-662; Volpato, et al., (2010) *Curr. Med. Chem.* 17, 3855-3873), even those that are non-natural (Meyer, et al., (2011) *JACS.* 133, 3609-3616; Seelig, et al., (2007) *Nature.* 448, 828-831). As enzymes often act on an array of structurally related compounds, they are often probed for activity on substrates other than their natural one to form a structure activity relationship (SAR) (Cisneros, et al., (2012) *J Med. Chem.* 55, 824-836). Additionally, when searching for the best performing enzyme, it is often desirable to either apply protein engineering to create new enzymes with a desired characteristic (Hibbert, et al., (2008) *J. Biotechnol.* 134, 240-245) or screen several homologs (Kubota, et al., (2013) *Appl. Microbiol. Biotechnol.* 97, 8139-8149; (9) Canganella, et al., (1994) *Appl. Microbiol. Biotechnol.* 42, 239-245).

The space to mine for the best performing enzyme is quite large. Large protein libraries can be generated in *E. coli* when applying protein engineering (Hibbert, et al., (2008)*J. Biotechnol.* 134, 240-245; Brissos, et al., (2008) *Protein Eng. Des. Sel.* 21, 387-393; Miyazaki, et al., (1999)*J. Mol. Evol.* 49, 716-720; Reetz, et al., (2010) *JACS.* 132, 9144-9152; Zaccolo, et al., (1999)*J. Mol. Biol.* 285, 775-783) and over 85,000 enzymatic reaction observations are cataloged in the largest public database (BRENDA) (Schomberg, et al., (2013) *Nucleic Acids Res.,* 41, D764-D772). Even this is dwarfed by estimates of total gene diversity in the environment (Henne, et al., (1999) *Appl. and Environ. Microbiol.,* 65:3901-3907; Qin, et al., J. (2010) *Nature,* 464:59-65; Venter, et al., (2004) *Science,* 304:66-74). Though there are many assays for monitoring enzymatic reactions, many reactions can only be observed using liquid or gas chromatography mass spectrometry (LCMS or GCMS) applied to purified protein. These are laborious and low-throughput and therefore severely limit the space that can be experimentally mined. As gene synthesis costs continue to decrease, the ability to perform such assays becomes the dominant bottleneck in mining efforts.

Natural products continue to serve as a key platform for drug development, many of which are decorated with essential sugar residues. Weymouth-Wilson A C (1997) *Nat Prod Rep* 14: 99-110. Adding or changing sugars attached to such natural products can improve the parent compound's pharmacological properties, specificity at multiple levels and/or even the molecular mechanism of action. Thorson J S, et al. (2002) in *Carbohydrate-Based Drug Discovery*, ed. Wong C-H (Wiley-VCH, Weinheim), pp. 685-712; Ahmed A, et al. (2006) *J Am Chem Soc* 128: 14224-5. An emerging method to differentially glycosylate natural products employs glycorandomization using natural or engineered permissive glycosyltransferases (GT). The successful glycorandomization of various natural product scaffolds has been reported including the antibiotic vancomycin, the antihelmenthic avermectin, and the anticancer agent calicheamicin. Fu X, et al. (2003) *Nat Biotechnol* 21: 1467-9; Zhang C, et al. (2006) *J Am Chem Soc* 128: 16420-1; Zhang C, et al. (2006) *Science* 313: 1291-4. In contrast, other recent antibiotic glycorandomization studies revealed novobiocin and erythromycin GTs, (NovM and EryBV), to accept only 2 alternative sugar nucleotides out of 25-40 potential donors tested. Albermann C, et al. (2003) *Org Lett* 5: 933-6; Zhang C, et al. (2007) *Chembiochem* 8: 385-390. Thus, while permissive GTs open new opportunities for drug discovery, the stringent specificity of other GTs remains a limiting factor in natural product diversification and highlights a need for general GT engineering and/or evolution platforms. Moreover, there remains a need for high throughput assays for monitoring GT reactivity and specificity A high throughput assay for enzyme activity, which matches the scalability of new DNA synthesis methods would constitute a significant advance in the art.

SUMMARY OF THE INVENTION

Traditional enzyme characterization methods are low-throughput, and therefore limit large-scale monitoring of enzyme activity and engineering efforts in synthetic biology and biotechnology. In various embodiments, the invention provides methodology to improve throughput and cost of enzyme characterization that matches the scalability of new DNA synthesis methods.

In an exemplary embodiment, the invention provides a DNA-linked enzyme-coupled assay (DLEnCA) to monitor enzyme reactions in a manner amenable to multiplex gene synthesis (Borovkov, et al., (2010) Nucleic acids research, 38, e180-e180; Kosuri, et al., (2010) *Nature Biotech.,* 28:1295-1299; Quan, et al., (2011) *Nature Biotech.,* 29:449-452) linked to multiplex readout in droplets and deep sequencing instrumentation (Mardis, E. R., (2008) *Annual Review of Ge-nomics and Human Genetics,* 9:387-402; Shendure, et al., (2008) *Nature Biotech.,* 26:1135-1145). The sample preparation steps of cloning plasmid DNA, transformation, and protein purification are eliminated, as is LCMS for analytics. We achieve this by uniting PCR and cell-free transcription/translation systems to generate protein and link the enzymatic output to modifications in DNA for easy analysis with agarose gels, quantitative PCR (qPCR), FRET probes, or next generation sequencing (Kinney, et al., (2011) *J. Biol. Chem.,* 286:24685-24693; Laird, P. W., (2010) *Nature Reviews Genetics,* 11:191-203; Terragni, et al., (2012) *Biochemistry,* 51:1009-1019).

DLEnCA is based on a competition between two enzymatic reactions for a common cofactor. The reactions are separated temporally, such that depletion of the cofactor in the first reaction results in no modification in the second reaction. In DLEnCA, the second reaction results in a modification of a polynucleotide in a polynucleotide preparation, e.g., DNA. The method of the invention is of use in monitoring any enzyme capable of modifying a nucleic acid residue within a polynucleotide preparation. Exemplary enzymes include glycosyltransferases and methyltransferases.

In an exemplary embodiment, the invention provides an assay for enzyme activity comprising the following steps: (a) incubating an enzyme preparation comprising the enzyme of interest with at least one cofactor for the enzyme of interest and at least one substrate for the enzyme of interest under conditions sufficient for the enzyme of interest to modify the at least one substrate with a moiety derived from the at least one cofactor; (b) following incubation, incubating the enzyme preparation with a polynucleotide preparation comprising the polynucleotide and a second enzyme capable of using the at least one cofactor to modify a nucleic acid of the polynucleotide, wherein the incubating is under conditions sufficient for the second enzyme to modify the nucleic acid of the polynucleotide preparation; and (c) determining whether the second enzyme modified the polynucleotide.

In an exemplary embodiment, the nucleic acid is a hydroxymethylated nucleic acid. In one embodiment, the hydroxymethylated nucleic acid is hydroxymethylcytidine.

The enzyme of interest is derived from any source. In an exemplary embodiment, the assay utilizes a cell free transcription/translation system to express the enzymes of interest. Thus, in an exemplary embodiment, prior to step (a), the enzyme of interest is expressed in a cell free transcription/translation system. As will be appreciated by those of skill in the art, the expression of the enzyme of interest is accomplished by an art-recognized means. In various embodiments, the enzyme of interest is expressed by incubating a linear DNA encoding the enzyme of interest operatively linked to a promoter in the cell free transcription/translation system.

The DNA-modifying enzymes are detectable downstream from the DNA modification by detecting the modification to the DNA mediated by the enzyme. Determining whether the polynucleotide is modified with a moiety derived from the cofactor is performed by any known method. In an exemplary embodiment, depletion of the cofactor in the first reaction (cofactor+substrate) is recorded as an absence of a chemical modification to the polynucleotide (e.g., DNA probe), and this difference can be translated into an easily observed signal by DNA digestion, followed by known methods, e.g., agarose gel analysis, qPCR, fluorescence, or deep sequencing.

In an exemplary embodiment, the modification to the DNA is detected by a DNA amplification methodology, e.g., Polymerase Chain Reaction (PCR), q-PCR, etc. In an exemplary embodiment, amplification is interrupted by the modification that the enzyme has made to the DNA template, and the modification is detectable The DLEnCA assays of the present invention are generalizable for many enzymatic reactions. In an exemplary embodiment, the invention provides a method for monitoring glycosyltransferases. The reactivity of the enzymes of interest is queried, while a nucleotide sugar and a glycosyltransferase are used to modify DNA, which is detected post-reaction using qPCR or similar means of DNA analysis.

In an exemplary embodiment, the invention provides an assay for monitoring OleD.

The present invention is exemplified for purposes of illustration by reference to an assay monitoring the activity of a glycosyltransferase. In the case of a glucosyltransferase version of DLEnCA, the assay employs the enzyme T4-β-glucosyltransferase (TbGT). TbGT modifies 5-hydroxym-ethyl-cytosine (5-hm-cytosine) residues in a DNA with the glucose moiety from uridine diphosphate glucose (UDP-Glc) (Kinney, et al., (2011) *J. Biol. Chem.*, 286:24685-24693; Terragni, et al., (2012) *Biochemistry*, 51:1009-1019; Morera, et al., (1999) *J. Mol. Biol.*, 292:717-730; Robertson, et al., (2011) *Nucleic Acids Res.*, 39, e55; Szwagierczak, et al., (2010) *Nucleic Acids Res.*, 38, e18125-28). This atypical base modification can be incorporated into a DNA using polymerase reactions containing 5-hydroxymethyl-dCTP (Huang, et al., (2010) *PLoS One*, 5, e8888) or by phosphoramidite synthesis (Jin, et al., (2010) *Nucleic Acids Res.*, 38, e125; Xu, et al., (2011) *Mol. Cell.*, 42:451-464). Therefore, the 5-hm-cytosine-modified DNA, referred to as the "probe" DNA within this publication, can be a small linear DNA fragment, modified FRET probe, or even the original DNA template that initiates the assay. The modification of the 5-hm-cytosines of the probe can be identified since glucosylation of double-stranded DNA can block recognition by other DNA modification enzymes, including restriction endonuclease digestion (Kinney, et al., (2011) *J. Biol. Chem.*, 286:24685-24693; Laird, P. W., (2010) *Nature Reviews Genetics*, 11:191-203; Terragni, et al., (2012) *Biochemistry*, 51:1009-1019). Therefore, depletion of the cofactor in the first reaction is recorded as an absence of a chemical modification to the DNA probe, and this difference can be translated into an easily observed signal by DNA digestion, followed by agarose gel analysis, qPCR, fluorescence, or deep sequencing.

A schematic overview of the DLEnCA assay is shown in FIG. 1. Two workflows were developed to follow an enzymatic reaction using a cell-free transcription/translation system: (1) a qPCR-amenable workflow, and (2) a fluorescence-amenable workflow. Both assay schemes are initiated upon the addition of linear DNA encoding a promoter and an enzyme of interest to a cell-free transcription/translation system. After an initial incubation period, UDP-Glc and chemical are added to the reaction. If the enzyme of interest is able to glucosylate the substrate, UPD-Glc concentrations within the reaction are depleted (FIG. 1A). The opposite is true if the enzyme of interest is not able to glucosylate the substrate (FIG. 1B). After a second incubation period, TbGT and DNA probe is added to the reaction. The probe is a linear DNA fragment where all cytosines have been modified to 5-hm-cytosine (qPCR readouts) or a hairpin DNA oligonucleotide modified to contain two 5-hm-cytosines within an MfeI recognition site, a 5' fluorophore, and a 3' quencher (fluorescence readouts). After a third incubation period is completed, MfeI restriction enzyme is added to the assay and the enzymatic reaction is read out using qPCR or fluorometry respectively.

In an exemplary experiment, the invention provides an assay for monitoring methyltransferases by competition of two reactions for S-adenosyl-L-methionine (SAM). Depletion of SAM prevents a DNA methyltransferse from modifying the DNA. In an exemplary embodiment, the methyltransferase is EcoRI methyltransferase, and the site on the DNA is the sequence GAATTC. Methylation of the DNA blocks cleavage by a nuclease, which in the exemplary embodiment is EcoRI restriction enzyme.

In an exemplary embodiment, the invention provides an assay for monitoring NADH-consuming reactions. In an exemplary first reaction step, a dehydrogenase or other NADH-consuming enzyme, substrate, and NADH react to generate an equivalent of NAD+. In an exemplary second step, *E. coli* or Taq DNA ligase consumes NAD+ to repair nicks in a DNA probe. Though NADH/NAD+ reactions are often reversible, the Taq DNA ligase reaction cleaves the cofactor into AMP and b-nicotinamide ribonucleotide which is irreversible. Thus, the two-step reaction sequence is thermodynamically driven to completion.

In an exemplary embodiment, the invention provides an assay for monitoring ATP-consuming reactions. In the first reaction, a kinase or other ATP-consuming enzyme of interest is incubated with its substrate(s) and ATP. Subsequently, a DNA probe lacking a 5' phosphate and T4 polynucleotide kinase is added. If the ATP is not depleted, the DNA becomes phosphorylated and can be detected due to its sensitivity to nucleases, such as Lambda Exonuclease. In an exemplary embodiment, the assay is applied to purified enzymes due to the consumption of ATP during translation and transcription.

In an exemplary embodiment, the present invention provides a DNA-linked enzyme-coupled assay (DLEnCA) to detect the presence of an enzyme of interest and monitor and characterize enzyme reactions in a high throughput format assay. High throughput in exemplary assays of the invention is facilitated by removing the need for protein (enzyme) purification and by limiting the need for liquid chromatography mass spectrometry (LCMS) product detection by linking enzymatic function to DNA modification.

In various embodiments, the assay of the invention is used to map the enzyme substrate specificity. In various embodiments, the invention provides an assay for monitoring glycosyltransferase reactions.

In various embodiments, the assay is used to monitor multiple steps in a biosynthetic pathway. In an exemplary embodiment, a multi-step biosynthetic pathway ends in a SAM-consuming reaction. The input chemical for the pathway and each enzyme of the pathway is supplied in the assay. If the entire conversion from input chemical to final methylated product occurs, then SAM is consumed and no DNA modification can occur when an EcoRI methyltransferase is subsequently added. If any one step of the pathway fails to occur, then the DNA becomes methylated. Thus, in various embodiments, fully functioning pathways are distinguished from those that containing at least one failed reaction step.

Other embodiments, advantages and objects of the present invention are apparent in the detailed description set forth hereinbelow.

BRIEF DESCRIPTION OF THE DRAWINGS

FIG. 1A-FIG. 1B. DNA-Linked Enzyme-Coupled Assay (DLEnCA). An overview of DLEnCA where the end readout is either qPCR or fluorescence using FRET. 1A represents a functional pairing of enzyme A and substrate S, leading to depletion of UDP-Glc and no modification of either qPCR or FRET probe by TbGT. The end result is the digestion of probes upon restriction enzyme addition. 1B represents a non-functional pairing of enzyme B and chemical S, leading to no depletion of UDP-Glc and no modification of probes by TbGT. The end result is the protection of the probes from restriction enzyme digestion. Key: TbGT=T4-β-glucosyltransferase; Glc=Glucose.

FIG. 21. Primers and probes used within this study.

FIG. 22. DNA Sequence: OleD-DQ195536.

FIG. 23. DNA Sequence: GT05-UGT72B1 (Q9M156).

FIG. 24. DNA Sequence: GT06-UGT89B1 (AT1G73880).

FIG. 25. DNA Sequence: "Probe" DNA (araC).

DETAILED DESCRIPTION OF THE INVENTION

Introduction

Figure 2A:
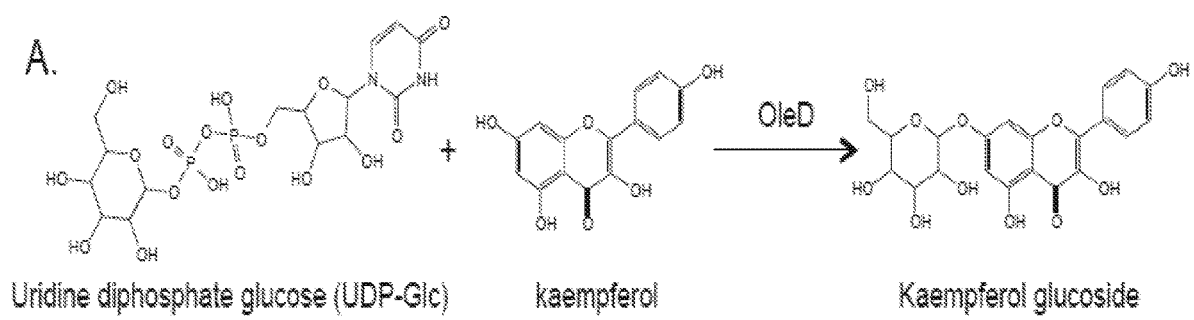
FIG. 2A-FIG. 2D. DNA-Linked Enzyme-Coupled Assay using purified model enzyme (OleD). A. The OleD-catalyzed glucosylation of kaempferol using UDP-Glc as a donor-molecule. B. Purified recombinant OleD (0.5 µM) was incubated with probe DNA (4.5 nM) in the presence of kaempferol (0.5 mM) and various concentrations of UDP-Glc at 37° C. for 1 hour. Following incubation with TbGT, DNA was digested with MfeI. Digests were analyzed on a 2% agarose gel. (i) % recovery of intact probe DNA was identified using band intensities quantified by ImageJ, and compared to completely protected probe intensities (n=4, error bars=standard error). (ii) A representative gel of the UDP-Glc titration reaction, as-well-as a "ladder" depicting expected DNA digestion sizes, is shown. C. Purified recombinant OleD (0.5 µM) was incubated with probe DNA (4.5 nM) in the presence of 4-hydroxybenzoic acid (0.5 mM) as acceptor and various concentrations of UDP-Glc at 37° C. for 1 hour. Following incubation with TbGT, DNA was digested with MfeI. Digests were analyzed on a 2% agarose gel (n=4). A representative gel of the titration, along with a "ladder" depicting expected DNA digestion sizes, is shown. D. Purified recombinant OleD (0.5 µM) was incubated with probe DNA (4.5 nM) in the presence of kaempferol (0.5 mM) and UDP-Glc (20 µM) at 37° C. for 1 hour. Following incubation with TbGT, DNA was incubated with MfeI. Digests were analyzed on a 2% agarose gel (n=4). A representative gel, including component knockdown reactions, along with a "ladder" depicting expected DNA digestion sizes is shown. Key: (P)=protected DNA after digestion with MfeI; (UP)=unprotected DNA after digestion with MfeI; (+)=presence of component in reaction; (−)=absence of component in reaction.

The DNA-linked enzyme-coupled assay (DLEnCA) of the present invention is based on a competition between two enzymatic reactions for a common cofactor. The reactions are separated temporally, such that depletion of the cofactor in the first reaction results in no modification in the second reaction. In DLEnCA, the second reaction results in a modification of a nucleic acid residue in a polynucleotide preparation, e.g., a DNA modification. An exemplary competition reaction involves the glycosylation of a nucleic acid site in a polynucleotide preparation by a glycosyltransferase (GT).

GTs constitute a large family with currently 23,000 predicted or known GT sequences in the CAZY database divided into 87 families based upon amino acid similarity. Despite the vast range of GT sugar donors and acceptors (sugars, proteins, nucleic acids, lipids, and small molecules), GTs are generally classified into two simple groups based upon mechanism (inverting or retaining), and primarily fall within two main structural superfamilies (GT-A and GT-B). Lairson L L, et al. (2004) *Chem Commun* 2243-8; Hu Y. et al. (2002) *Chem Biol* 9: 1287-96. The GT-B fold is the predominate fold of natural product GTs and is characterized by two closely associated Rossman-like domains, each of which is usually distinguished as the acceptor- and donor-binding domains (N and C-terminal domains, respectively).

Despite the wealth of GT structural and biochemical information, attempts to alter GT donor/acceptor specificities via rational engineering have been largely unsuccessful and primarily limited to sequence-guided single site mutagenesis. Hancock S M, et al. (2006) *Curr Opin Chem Biol* 10: 509-19. While there exists precedent for the directed evolution of carbohydrate-utilizing enzymes, the lack of sensitive high-throughput screens for GTs has also hampered GT directed evolution. Hoffmeister D, et al. (2003) *Proc Natl Acad Sci USA* 100: 13184-9; Williams G J, et al. (2006) *J Am Chem Soc* 128: 16238-47. Withers et al recently described a unique in vivo selection for the directed evolution of the bifunctional sialyltransferase CstII, the structure of which closely resembles those of the GT-A superfamily, and has recently been suggested to be classified into a third structural superfamily (GT-C). Aharoni A, et al. (2006) *Nat Methods* 3: 609-14; Chiu C P, et al. (2004) *Nat Struct Mol Biol* 11: 163-70; Breton C, et al. (2006) *Glycobiology* 16: 29R-37R. The CstII directed evolution study relied upon trapping a fluorescently-tagged acceptor sugar inside *E. coli* upon modification by the negatively-charged sialic acid as an in vivo screen. Yet, there remains a lack of versatile high throughput screens or directed evolution studies targeted toward the structurally distinct and functionally important GT family.

Definitions

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The "polynucleotide preparation" refers to a single polynucleotide or a plurality of polynucleotides in solution or immobilized on a matrix. The polynucleotide preparation may contain a single copy or multiple copies of a single sequence or may contain a mixture of polynucleotides with varying sequences. The polynucleotides may be synthetic or derived from genomic DNA where the genomic DNA may be a mammalian or other eukaryotic genome or a prokaryotic genome but does not include bacterial virus DNA. The polynucleotides in the preparation may include additional defined sequences in the form of double- or single-stranded oligonucleotides hybridized to one or both termini. These oligonucleotides may be synthetic and include adapters or primers or labels.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. The nucleic acid can comprise DNA, RNA or chimeric mixtures or derivatives or modified versions thereof. In addition to the naturally occurring "nucleobases," adenine, cytosine, guanine and thymine, nucleic acid components of the compounds of the invention optionally include modified bases. These components can also include modified sugars.

A "reference" polynucleotide as used here refers to a polynucleotide optionally in a database with defined properties that provides a control for assessing the modification of the polynucleotide in the polynucleotide preparation or polynucleotide being investigated for derivitization by an enzyme in a method of the invention.

As used herein, the term "glycosyltransferase," refers to any enzyme/protein that has the ability to derivatize a polynucleotide, e.g., transfer a donor sugar to an acceptor moiety.

"Substantially similar" as used here refers to at least compositions or patterns or other items which, when compared, are not necessarily identical but share at least 50%, or as much as 60%, 70%, 80% or 90% of a quantified amount of a trait.

As used herein, "DNA methyltransferase" is a protein which is capable of methylating a particular DNA sequence.

Abbreviations

"FET", as used herein, refers to "Fluorescence Energy Transfer."

"FRET", as used herein, refers to "Fluorescence (Foerster) Resonance Energy Transfer." These terms are used herein to refer to both radiative and non-radiative energy transfer processes. For example, processes in which a photon is emitted and those involving long-range electron transfer are included within these terms.

EXEMPLARY EMBODIMENTS

In an exemplary embodiment, the invention provides an assay for enzyme activity comprising the following steps: (a) incubating an enzyme preparation comprising the enzyme of interest with at least one cofactor for the enzyme of interest and at least one substrate for the enzyme of interest under conditions sufficient for the enzyme of interest to modify the at least one substrate with a residue derived from the at least one cofactor; (b) following incubation, incubating the enzyme preparation with a polynucleotide preparation comprising the polynucleotide and a second enzyme known to use the at least one cofactor to modify a nucleic acid of the polynucleotide, wherein the incubating is under conditions sufficient for the second enzyme to modify the nucleic acid of the polynucleotide preparation; and (c) determining whether the second enzyme modified the polynucleotide.

In an exemplary embodiment, the invention provides a DNA-linked enzyme-coupled assay (DLEnCA) to monitor enzyme reactions in a manner amenable to multiplex gene synthesis (Borovkov, et al., (2010) Nucleic acids research, 38, e180-e180; Kosuri, et al., (2010) Nature Biotech., 28:1295-1299; Quan, et al., (2011) Nature Biotech., 29:449-452) linked to multiplex readout in droplets and deep sequencing instrumentation (Mardis, E. R., (2008) Annual Review of Ge-nomics and Human Genetics, 9:387-402; Shendure, et al., (2008) Nature Biotech., 26:1135-1145). The sample preparation steps of cloning plasmid DNA, transformation, and protein purification are eliminated, as is LCMS for analytics. In an exemplary embodiment, the invention provides a method uniting PCR and cell-free transcription/translation systems to generate protein and link the enzymatic output to modifications in DNA for easy analysis with agarose gels, quantitative PCR (qPCR), FRET probes, or next generation sequencing (Kinney, et al., (2011) J. Biol. Chem., 286:24685-24693; Laird, P. W., (2010) Nature Reviews Genetics, 11:191-203; Terragni, et al., (2012) Biochemistry, 51:1009-1019).

Figure 28A:
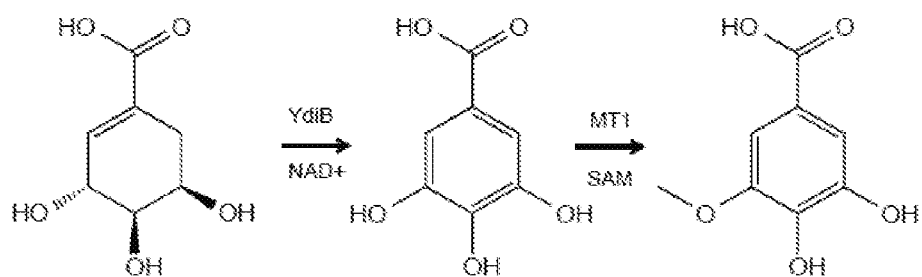
FIG. 28A-FIG. 28B. Following a pathway using DMTase and the fluorescent probe. (A) A two-step reaction sequence in which shikimic acid is oxidized and subsequently methylated to 3-O-methylgallic acid by YdiB and MT1, respectively. (B) Monitoring of the two step pathway by DLEnCA. When MT1 and YdiB are supplied on a plasmid, and the NAD+ cofactor and shickimate are provided, SAM is consumed, the oligo probe remains unmethylated, and is cleaved with EcoRI restriction endonuclease resulting in fluorescence. Omission of either biosynthetic gene, NAD+, or shikimate results in signal loss.
Figure 28B:
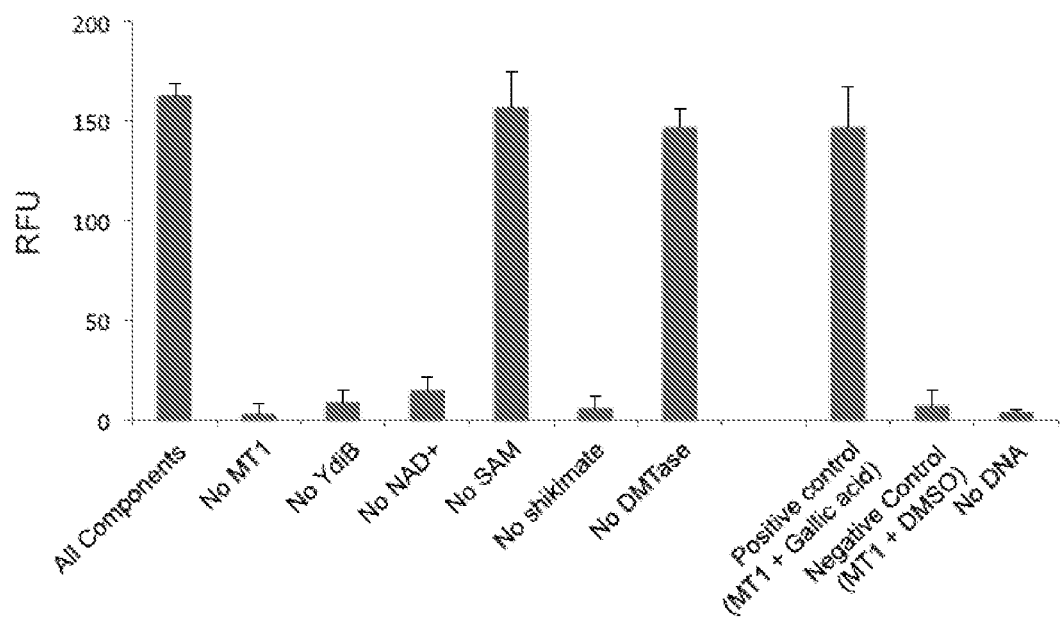
Figure 29:
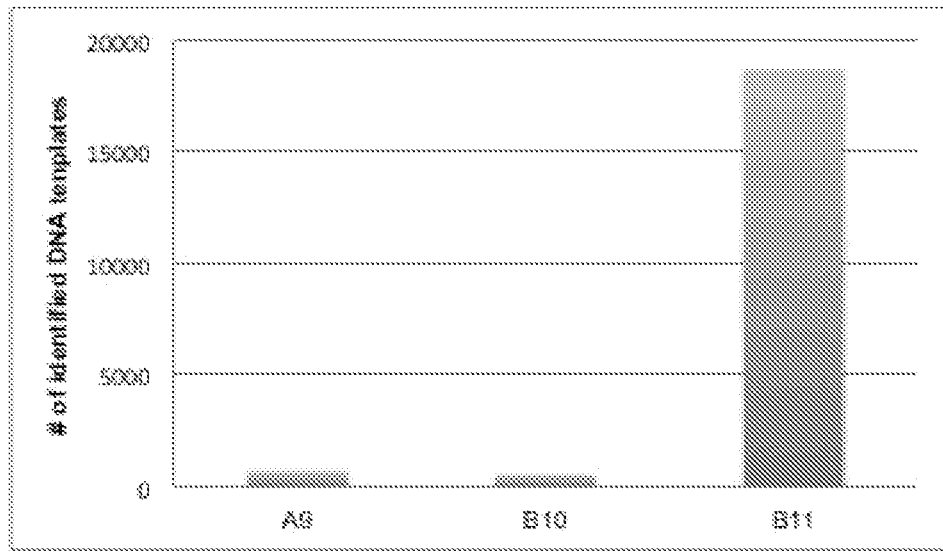
FIG. 29. Counts of DNAs present in a deep-sequencing run to readout DLEnCA.

In various embodiments, DLEnCA is used in a method for monitoring an entire biosynthetic pathways for high-throughput prototyping applications, including directed evolution and combinatorial experiments. For example, if a sequence of reactions ends with a step that consumes a cofactor detectable by DLEnCA, then a lack of conversion at any previous step will result in a loss of cofactor depletion. Thus, a positive DLEnCA signal confirms all earlier steps in the pathway. In an exemplary embodiment, the method provides a method for testing a two-step pathway whose last step is a methylation reaction using the FRET variant of the methyltransferase DLEnCA assay (FIG. 28A-B). When all components are provided, the cofactor is consumed, the DNA is unmethylated, and a signal is observed. When any single component is omitted, the signal is lost confirming that each individual component of the pathway is necessary for it to occur.

As will be apparent to those of skill in the art, the invention can be practiced on a range of enzymes Exemplary embodiments of the invention involve querying the reactivity of glycosyltransferases, designing new glycosyltransferases and synthesizing compounds using newly designed glycosyltransferases.

Glycosyltransferases

Glycosyltransferases catalyze the addition of activated sugars (donor NDP-sugars), in a step-wise fashion, to molecules (e.g., terpenoids, non-ribosomal peptides, polyketides, flavonoids and the like), a protein, glycopeptide, lipid or glycolipid or to the non-reducing end of a growing oligosaccharide. A very large number of glycosyltransferases are known in the art.

The glycosyltransferase to be used in the present invention may be any as long as it can utilize the modified sugar as a sugar donor. Examples of such enzymes include Leloir pathway glycosyltransferases, such as galactosyltransferase, N-acetylglucosaminyltransferase, N-acetylgalactosaminyltransferase, fucosyltransferase, sialyltransferase, mannosyltransferase, xylosyltransferase, glucuronylnyltransferase and the like.

For enzymatic saccharide syntheses that involve glycosyltransferase reactions, glycosyltransferases can be cloned, or isolated from any source. Many cloned glycosyltransferases are known, as are their polynucleotide sequences. See, e.g., Taniguchi et al., 2002, Handbook of Glycosyltransferases and Related Genes, Springer, Tokyo.

Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid and transferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out using oligonucleotide probes generated from the glycosyltransferases nucleic acid sequence. Probes may be labeled with a detectable label, such as, but not limited to, a fluorescent group, a radioactive atom or a chemiluminescent group in accordance with known procedures and used in conventional hybridization assays. In the alternative, glycosyltransferases nucleic acid sequences may be obtained by use of the polymerase chain reaction (PCR) procedure, with the PCR oligonucleotide primers being produced from the glycosyltransferases nucleic acid sequence. See, U.S. Pat. No. 4,683,195 to Mullis et al. and U.S. Pat. No. 4,683,202 to Mullis.

A glycosyltransferase enzyme may be synthesized in a host cell transformed with a vector containing DNA encoding the glycosyltransferases enzyme, or in a cell free transcription/translation system. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host (or cell free system). The need for such control sequences will vary depending upon the expression system selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the glycosyltransferase is expressed in an in vitro cell free transcription/translation system. Constructs for expression of glycosyltransferases and other enzymes are generally known in the art and are applicable in the invention set forth herein.

In the case of a glucosyltransferase version of DLEnCA, an exemplary assay employs the enzyme T4-β-glucosyltransferase (TbGT). TbGT modifies 5-hydroxymethyl-cytosine (5-hm-cytosine) residues in a DNA with the glucose moiety from uridine diphosphate glucose (UDP-Glc) (Kinney, et al., (2011) $J.$ $Biol.$ $Chem.,$ 286:24685-24693; Terragni, et al., (2012) $Biochemistry,$ 51:1009-1019; Morera, et al., (1999)$J.$ $Mol.$ $Biol.,$ 292:717-730; Robertson, et al., (2011) $Nucleic$ $Acids$ $Res.,$ 39, e55; Szwagierczak, et al., (2010) $Nucleic$ $Acids$ $Res.,$ 38, e18125-28). This atypical base modification can be incorporated into a DNA using polymerase reactions containing 5-hydroxymethyl-dCTP (Huang, et al., (2010) $PLoS$ $One,$ 5, e8888) or by phosphoramidite synthesis (Jin, et al., (2010) $Nucleic$ $Acids$ $Res.,$ 38, e125; Xu, et al., (2011) $Mol.$ $Cell.,$ 42:451-464). Therefore, the 5-hm-cytosine-modified DNA, referred to as the "probe" DNA within this publication, can be a small linear DNA fragment, modified FRET probe, or even the original DNA template that initiates the assay. The modification of the 5-hm-cytosines of the probe can be identified since glucosylation of double-stranded DNA can block recognition by other DNA modification enzymes, including restriction endonuclease digestion (Kinney, et al., (2011)$J.$ $Biol.$ $Chem.,$ 286:24685-24693; Laird, P. W., (2010) $Nature$ $Reviews$ $Genetics,$ 11:191-203; Terragni, et al., (2012) $Biochemistry,$ 51:1009-1019). Therefore, depletion of the cofactor in the first reaction is recorded as an absence of a chemical modification to the DNA probe, and this difference can be translated into an easily observed signal by DNA digestion, followed by agarose gel analysis, qPCR, fluorescence, or deep sequencing.

A schematic overview of an exemplary DLEnCA assay is shown in FIG. 1. Two workflows were developed to follow an enzymatic reaction using a cell-free transcription/translation system: (1) a qPCR-amenable workflow, and (2) a fluorescence-amenable workflow. Both assay schemes are initiated upon the addition of linear DNA encoding a promoter and an enzyme of interest to a cell-free transcription/translation system. After an initial incubation period, UDP-Glc and chemical are added to the reaction. If the enzyme of interest is able to glucosylate the substrate, UPD-Glc concentrations within the reaction are depleted (FIG. 1A). The opposite is true if the enzyme of interest is not able to glucosylate the substrate (FIG. 1B). After a second incubation period, TbGT and DNA probe is added to the reaction. The probe is a linear DNA fragment where all cytosines have been modified to 5-hm-cytosine (qPCR readouts) or a hairpin DNA oligonucleotide modified to contain two 5-hm-cytosines within an MfeI recognition site, a 5' fluorophore, and a 3' quencher (fluorescence readouts). After a third incubation period is completed, MfeI restriction enzyme is added to the assay and the enzymatic reaction is read out using qPCR or fluorometry respectively.

The invention also encompasses a DNA-linked assay for identifying a mutant enzyme. These enzymes can be mutated to alter any desirable property, e.g., expanded or contracted substrate specificity, increased or decreased stability, accessibility of synthetic or degradative reaction pathways, etc. In the present disclosure, this embodiment of the invention is illustrated by reference to a glycosyltransferase as a representative enzyme that can be mutated and assayed by the method of the invention.

In an exemplary embodiment, the invention provides a glycosyltransferase exhibiting expanded substrate specificity as compared to a corresponding non-mutated glycosyltransferase. Such a method includes steps of: (a) providing a library of mutant glycosyltransferases; and (b) submitting the library to one or more cycle of DLEnCA. In an exemplary embodiment, each mutant glycosyltransferase is incubated with a nucleotide sugar and a polynucleotide preparation in which the polynucleotide includes at least one nucleic acid capable of being acceptor for the sugar moiety of the nucleotide sugar; and (c) detecting glycosylation of the sugar acceptor in the polynucleotide preparation incubated with each mutant glycosyltransferase. Each mutant glycosyltransferase's ability to transfer a sugar from the nucleotide sugar to the polynucleotide sugar acceptor is detectable, e.g., indicated by an alteration in the nuclease digestion pattern of the glycoslyated polynucleotide. In an exemplary embodiment, the glycosyltransferase is a glucosyltransferase (e.g., OleD).

In various embodiments, the invention uses a DNA-linked assay in a method of optimizing glycosyltransferases toward non-natural acceptors through a comprehensive program of 'hot spot' saturation mutagenesis of functional positions. The method comprises a general enzyme optimization strategy (hot spot saturation mutagenesis) applicable to reactions limited by amenable high throughput screens using a model glycosyltransferase. Specifically, a high throughput screen (based upon DLEnCA) is used to identify key amino acid 'hot spots' that contribute to GT proficiency and/or promiscuity. Saturation mutagenesis of the corresponding hot spots, and subsequent assay of the resulting mutant glycosyltransferases by a method of the invention provides a glycosyltransferase with expanded/different substrate specificity relative to the wild type glycosyltransferase. In an exemplary embodiment, the glycosyltransferase is a glucosyltransferase (e.g., OleD).

Yet another embodiment of the invention is directed to a method of providing a mutant glycosyltransferase with expanded substrate specificity. An exemplary method includes steps of: (a) expressing a selected glycosyltransferase mutated at one or more amino acids; and (b) isolating from the host cell the mutant glycosyltransferase that exhibits an expanded substrate specificity as compared to a corresponding non-mutated glycosyltransferase. The glycosyltransferase can be expressed in a host cell or a cell free transcription/translation system. In an exemplary embodiment, the glycosyltransferase is a glucosyltransferase (e.g., OleD).

The invention also provides a method of preparing a glycosylated compound which includes steps of: (a) combining: (i) a nucleotide sugar; (ii) an isolated mutant glycosyltransferase, characterized by a method of the invention, and mutated at one or more amino acids wherein the isolated mutant glycosyltransferase exhibits an expanded substrate specificity as compared to a corresponding non-mutated glycosyltransferase; and (iii) an aglycon capable of being glycosylated; and (b) recovering the glycosylated compound. The isolated mutant glycosyltransferase transfers a sugar from the nucleotide sugar to the aglycon thereby producing the glycosylated compound. In an exemplary embodiment, the glycosyltransferase is a glucosyltransferase (e.g., OleD).

A broad range of nucleotide sugars may be used in the method including naturally occurring and non-natural nucleotide sugars. Similarly, a broad range of aglycons may be included in the method, including but not limited to, macrolide, flavonoid, isoflavone, coumarin, aminocouramin or coumarin acid molecules. Exemplary macrolides useful as aglycones include natural or synthetic pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones, flavonoids, isoflavones, coumarins, aminocoumarins, coumarin acids, polyketides, pluramycins, aminoglycosides, oligosaccharides, nucleosides, peptides and proteins.

In certain methods of preparing a glycosylated compound, there is included the additional step of preparing the nucleotide sugar by combining a nucleotide triphosphate (NTP) and a sugar phosphate in the presence of a nucleotidyltransferase before or concurrently with the glycosylation reaction. In fact, the nucleotidyltransferase and glycosyltransferase reactions may be optionally carried out in a single reaction vessel. LT2 rmlA-encoded alpha-D-glucopyranosyl phosphate thymidylyltransferase ($E_p$) is an exemplary nucleotidyltransferase for use in the method although other nucleotidyltransferases may be utilized, including both wild-type and mutant forms.

DNA Analysis for DNA Modification Detection and Mapping

The availability of selective tools for DNA modification permits detection and mapping of modification to yield information about the reactivity and specificity of the enzyme catalyzing the modification of the DNA.

Individual DNA modifications may be identified and mapped on a reference nucleic acid that may already have modified/modifiable locations identified or may be limited to an unmodified nucleic acid. A single modification or a cluster of modifications containing multiple modifications may be identified at a particular locus, and subsequent analysis allows mapping of that locus. A series of nucleic acid maps of modification sites sampled at appropriate times can reveal how a pattern of modification changes over time and in changing environments, as well as among different nucleic acids, e.g., different nucleic acids corresponding to the genome of tissues differing in type, function, and disease state. The modification of sites on the DNA and the use of enzymes that differentially cleave or are inhibited by modification compared provide methods enabling the monitoring of changes in modification at specific loci, thus facilitating the understanding of the significance of mutations in the enzymes of interest.

Using the general approach described herein, identification and mapping of modification in a polynucleotide probe can be accomplished by various methods. In an exemplary embodiment, the method utilizes site-specific reagents for identifying modified nucleic residues within isolated polynucleotide fragments in an assay of the invention. For example, site-specific endonucleases may cleave at defined distances from the modification or, alternatively, they may fail to cleave at an expected site because of the presence of a modification. This facilitates localization and quantification of modification as the sequence context is identified in the course of sequence determination.

In various embodiments, the endonuclease is sensitive to glycosylation of the DNA. Exemplary glycosyltransferases catalyzing this modification are discussed herein.

In an exemplary embodiment, the endonuclease is sensitive to methylation of the DNA. For example, the MspJI family has been described in WO 2010/075375 and representative members have been characterized (e.g., MspJI, Sgrit 16873, Franean 1 (FspEI), lpg1234 (LpnPI), AspBHI and RlaI). These endonucleases recognize C, mC or hmC and cleave at a distance (N12/N16). Each member of the class displays some preference for specific flanking nucleotides around the modified cytosine. All of them are able to cleave genomic DNA on both sides of a subset of symmetrically methylated sites to produce a set of homogeneously-sized fragments containing a centrally located mN or modification. Interestingly, RlaI, an enzyme acting on mCWG but not on mCpG sites, generates different digestion patterns between the plant and mammalian genomic DNA.

In various embodiments, the cleavage fragments from the endonuclease digestion can then be ligated to external DNA sequences required for selective amplification and/or subsequent sequence analysis. Following ligation, samples are treated with an enzyme that selectively modifies the unmodified nucleic acid, but not the modified nucleic acid. In various embodiments, the enzyme selectively modifies the modified DNA (e.g., cleaving methylated DNA) but not the unmodified DNA. Subsequently, the modified samples are once again incubated with the site-specific endonuclease. DNA fragments containing unmodified DNA are liberated from the ligated flanking sequences, and thus not amplified or analyzed in subsequent steps. In contrast, DNA fragments containing modification are not cleaved, and thus retain the ability to be amplified and/or sequenced using the ligated flanking sequences. The use of different endonucleases allows interrogation of different subsets of sites and thus expands coverage of the modified polynucleotide.

In an exemplary embodiment, modifications to the probe are queried using deep sequencing of digested DNA fragments generated from these enzymes, providing a means to map the majority of the modified sites.

In an exemplary embodiment, modifications to the probe are queried using deep sequencing of digested DNA fragments containing DNA barcodes. Individual DNAs encoding enzymes to be tested and a unique DNA barcode are added to small in vitro transcription/translation reactions. After incubation, a substrate is added to each reaction, allowed to react, and then the DNA modifying enzyme is added. The reactions are then quenched, pooled, and as a population treated with the restriction enzyme or other DNA modifying enzyme sensitive to the initial modification. The population of DNAs inside the pool that was cleaved by the enzyme can be ligated to adapters and submitted for deep sequencing. The activity of the original enzyme is read out by counting how many of each barcode is present in the sequencing data. In another embodiment, a second DNA barcode is included in each reaction that encodes the substrate, and many substrates are examined against many enzymes within a single run of the experiment.

In an embodiment, differentiating cleaved from uncleaved molecules may be carried out by a variety of methods known in the art. For example, cleavage patterns can be analyzed by Southern Blots in which fragments are generated, separated by gel electrophoresis, transferred to a membrane, and probed with labeled nucleic acids homologous to sequences at and around the locus of interest. Secondary restriction endonuclease cleavage may be used to further bracket the locus of interest. Nucleic acid arrays can also be employed in which arrays contain segments spanning the cleavage site.

Hybridization of cleaved loci may be less stable as fewer contiguous nucleotides will be available for hybridization. Polynucleotide probes, employing hairpin structures whose fluorescent output is enhanced on DNA hybridization, but decreased in the absence of probes, can also be used to measure the cleavage state of the locus of interest. Alternative methods for determining the cleavage state of a specific site are known in the art, and could also be utilized.

Polynucleotide Probes

The polynucleotide preparations including a polynucleotide probe of use in the present invention may include FET or FRET components or other moieties allowing the probe itself or changes in the probe to be detected as a component of the assay.

In one embodiment, a nucleic acid comprising a fluorescent dye is used as a probe. The nucleic acid probe can be used in solution phase or it can be attached to a solid support. Chemical synthesis of polynucleotide probes containing a dye is performed by any art-recognized method. An exemplary method of synthesizing the polynucleotide is automated and is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. A fluorescent label can be incorporated during oligonucleotide synthesis using a mono- or bis-phosphoramidite derivative of the fluorescent compound. Alternatively, the label can be introduced by combining a compound of the invention that includes a reactive functional group with the nucleic acid under appropriate conditions to couple the compound to the polynucleotide. The fluorescent compound can also be attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners. The present invention also provides dual labeled probes that include both a dye of the invention and another label. Exemplary dual labeled probes include nucleic acid probes that include a nucleic acid with a dye of the invention attached thereto, typically, through an adaptor or adaptor-linker cassette. Exemplary probes include both a dye of the invention and a quencher. The probes are of use in a variety of assay formats. For example, when a nucleic acid singly labeled with a dye of the invention is the probe, the interaction between the first and second nucleic acids can be detected by observing the interaction between the dye of the invention and the nucleic acid. Alternatively, the interaction is the quenching by a quencher attached to the second nucleic acid of the fluorescence from a dye of the invention.

The present invention also provides dual labeled probes that include both a dye of the invention and another label. Exemplary dual labeled probes include nucleic acid probes that include a nucleic acid with a dye of the invention attached thereto, typically, through an adaptor or adaptor-linker cassette. Exemplary probes include both a dye of the invention and a quencher. The probes are of use in a variety of assay formats. For example, when a nucleic acid singly labeled with a dye of the invention is the probe, the interaction between the first and second nucleic acids can be detected by observing the interaction between the dye of the invention and the nucleic acid. Alternatively, the interaction is the quenching by a quencher attached to the second nucleic acid of the fluorescence from a dye of the invention.

Polynucleotide probes of use in the invention may figure in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the polynucleotide probes of use in the present invention can be in substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics,* 21:836-850 (1953); Hochstrasser, R. A., et al., *Biophysical Chemistry,* 45:133-141 (1992); Selvin, P., *Methods in Enzymology,* 246:300-334 (1995); Steinberg, I., *Ann. Rev. Biochem.,* 40:83-114 (1971); Stryer, L., *Ann. Rev. Biochem.,* 47:819-846 (1978); Wang, G., et al., *Tetrahedron Letters,* 31:6493-6496 (1990); Wang, Y., et al., *Anal. Chem.,* 67:1197-1203 (1995); Debouck, C., et al., in supplement to *nature genetics,* 21:48-50 (1999); Rehman, F. N., et al., *Nucleic Acids Research,* 27:649-655 (1999); Cooper, J. P., et al., *Biochemistry,* 29:9261-9268 (1990); Gibson, E. M., et al., *Genome Methods,* 6:995-1001 (1996); Hochstrasser, R. A., et al., *Biophysical Chemistry,* 45:133-141 (1992); Holland, P. M., et al., *Proc Natl. Acad. Sci USA,* 88:7276-7289 (1991); Lee, L. G., et al., *Nucleic Acids Rsch.,* 21:3761-3766 (1993); Livak, K. J., et al., *PCR Methods and Applications,* Cold Spring Harbor Press (1995); Vamosi, G., et al., *Biophysical Journal,* 71:972-994 (1996); Wittwer, C. T., et al., *Biotechniques,* 22:176-181 (1997); Wittwer, C. T., et al., *Biotechniques,* 22:130-38 (1997); Giesendorf, B. A. J., et al., *Clinical Chemistry,* 44:482-486 (1998); Kostrikis, L. G., et al., *Science,* 279:1228-1229 (1998); Matsuo, T., *Biochemica et Biophysica Acta,* 1379:178-184 (1998); Piatek, A. S., et al., *Nature Biotechnology,* 16:359-363 (1998); Schofield, P., et al., *Appl. Environ. Microbiology,* 63:1143-1147 (1997); Tyagi S., et al., *Nature Biotechnology,* 16:49-53 (1998); Tyagi, S., et al., *Nature Biotechnology,* 14:303-308 (1996); Nazarenko, I. A., et al., *Nucleic Acids Research,* 25:2516-2521 (1997); Uehara, H., et al., *Biotechniques,* 26:552-558 (1999); D. Whitcombe, et al., *Nature Biotechnology,* 17:804-807 (1999); Lyamichev, V., et al., *Nature Biotechnology,* 17:292 (1999); Daubendiek, et al., *Nature Biotechnology,* 15:273-277 (1997); Lizardi, P. M., et al., *Nature Genetics,* 19:225-232 (1998); Walker, G., et al., *Nucleic Acids Res.,* 20:1691-1696 (1992); Walker, G. T., et al., *Clinical Chemistry,* 42:9-13 (1996); and Compton, J., *Nature,* 350:91-92 (1991).

In view of the well-developed body of literature concerning the conjugation of small molecules to nucleic acids, many methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research,* 15: 5305-5321 (1987) (3'-thiol group on nucleic acid); Sharma et al., *Nucleic Acids Research,* 19: 3019 (1991) (3'-sulfhydryl); Giusti et al., *PCR Methods and Applications,* 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters,* 31: 1543-1546 (1990) (attachment via phosphoramidate linkages); Sproat et al., *Nucleic Acids Research,* 15: 4837 (1987) (5-mercapto group); Nelson et al., *Nucleic Acids Research,* 17: 7187-7194 (1989) (3'-amino group), and the like.

There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to polynucleotide probes having detectable moieties other than fluorescent compounds, e.g., quenchers, intercalating agents, hybridization enhancing moieties, minor groove binders, alkylating agents, cleaving agents, etc.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the dye of the invention by at least about 10 nucleotides, and more preferably by at least about 15 nucleotides. The quencher moiety is preferably attached to either the 3'- or 5'-terminal nucleotides of the probe. The dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Bioinformatic Analysis

Candidate loci may be identified by comparison of the derived sequences with a reference polynucleotide using bioinformatic methods known in the art, for example by BLAST comparison with UCSC hg18 (NCBI Build 36) which is a reference assembly for all human DNA sequence. The candidate loci from numerous polynucleotide samples may be determined using techniques such as deep sequencing (Shendure and Ji, *Nature Biotechnology* 26: 1135-1145 (2008)). It is envisaged that bioinformatic methods present in the art for determining suitable single nucleotide polymorphisms (SNPs) biomarkers may be applied to the analysis of derivatized nucleic acid biomarkers. Techniques from other fields such as astronomy that analyze time-based signals to identify patterns may also provide data mining tools for recognizing patterns where structure is correlated with function.

The following examples are provided to illustrate selected embodiments of the current invention and are not to be construed as limiting the scope of the invention.

EXAMPLES

Example 1

Methods

Enzymes and Reagents:

T4 Phage β-glucosyltransferase (M0357L), MfeI (R0589L), UDP-Glucose (S2200S), dNTP mix (N0447L), and the PURExpress In Vitro Protein Synthesis Kit (E6800L) were purchased from NEB. The glucosyltransferase was dialyzed against PBS for two hours prior to use. All other reagents were employed without further purification. 5-hydroxymethylcytosine dNTP mix (D1040) was purchased from Zymo Research. Phusion High-Fidelity DNA polymerase (F-530L) was purchased from Thermo Scientific. One Shot TOP10 Chemically Competent $E.$ $coli$ (404003) was purchased from Invitrogen. L-arabinose (A3256), Kaempferol (60010-25 mg), Kaempferol-3-glucoside (68437-5MG), Kaempferol-7-glucoside (18854-1MG), 3-hydroxybenzoic acid (H20008-100G), 3,4-dihydroxybenzoic acid (37580-25G-F), and 5-hydroxyflavone (H4405-250 mg) were purchased from Sigma Aldrich; 4-hydroxyflavone (H-411) was purchased from Indofine Chemical Company Inc.; 7-hydroxyflavone (H0852) was purchased from TCI America; 3-hydroxyflavone (A18110) and 4-hydroxybenzoic acid (Ser. No. 10/170,920) were purchased from AlfaAesar; apigenin (sc3529A), 4-methylumbelliferone (sc206910) and 7-hydroxycoumarin-4-acetic acid (sc210628) were purchased from Santa Cruz Biotechnology; 7-hydroxycoumarin-3-carboxylic acid (81215) was purchased from AnaSpec. Plates for qPCR were purchased from Bio-Rad (2239441). Water Optima-LCMS (W6-4), Formic Acid Optima-LCMS (A117-50) and Acetonitrile Optima-LCMS (A955-4) were purchased from Fisher Scientific. All oligonucleotides were purchased from Integrated DNA Technologies.

Cloning of oleD:

Genetic constructs for expression of glucosyltransferases were fabricated as clonal plasmid samples from preexisting DNAs. Each construct contained the glucosyltransferase under the transcriptional control of a T7 promoter and a $T_{rrnB}$ terminator. The sequences of primers used in this study are listed in Table S1. For the OleD construct, genomic DNA was extracted from $Streptomyces$ $antibioticus$ using the UltraClean Microbial DNA Isolation Kit (MO BIO Laboratories). The gene encoding OleD (accession # DQ195536.2) was PCR amplified with primers P01 and P02 using Phusion polymerase. The pET15B backbone containing the T7 promoter, origin of replication, and ampicillin-resistance gene was amplified using primers P03 and P04. The PCRs were carried out using a PTC-200 Peltier Thermo Cycler at the following temperatures for OleD; 98° C. 2 minutes followed by 35 cycles at 98° C. 30 seconds, 60° C. 30 seconds, and 72° C. for 1.5 minutes, with a final single extended elongation phase at 72° C. for 10 minutes. For the backbone the elongation time was extended to 5 minutes. The amplified DNA was gel purified and added to Gibson Assembly Master Mix (NEB E2611S) and assembled using the recommended protocol. Plasmid was transformed into chemically competent $E.$ $coli$ strain DH10B.

Cloning of Other GTs:

$Arabidopsis$ $thaliana$ cDNA was kindly donated by the Feldman laboratory of UC Berkeley. GT05 (accession # UGT72B1) was amplified using primers P05 and P06, while GT06 (accession # UGT89B1) was amplified using primers P07 and P08. The PCRs were carried out using the following temperature program; 98° C. 2 minutes followed by 35 cycles at 98° C. 30 seconds, 62° C. 30 seconds, and 72° C. for 1.5 minutes, with a final single extended elongation phase at 72° C. for 10 minutes. DNA was then digested using Restriction Enzymes NcoI and BamHI, and cloned into a pre-digested pET15b vector.

DNA for Assay:

Linear DNA was amplified from sequence-verified plasmids with primers P09 and P10 using the following temperatures: 98° C. 2 minutes followed by 35 cycles at 98° C. 30 seconds, 62° C. 30 seconds, and 72° C. for 1.5 minutes, with a final single extended elongation phase at 72° C. for 10 minutes. DNA was purified using DNA Clean & Concentrator (Zymo Research). DNA was quantified using NanoDrop.

Production of Probe DNA:

The araC gene was amplified from pNE2001, a derivative of pBAD/Myc-His A (Life Technologies) using primers 011 and 012, Phusion DNA polymerase, and the 5-hydroxymethylcytosine dNTP mix. The PCR was carried out using the following temperatures; 98° C. 2 minutes followed by 35 cycles at 98° C. 30 seconds, 60° C. 30 seconds, and 72° C. for 1 minute, with a final single extended elongation phase at 72° C. for 10 minutes. DNA was gel purified using the Zymoclean Gel DNA recovery Kit (Zymo Research).

Purification of OleD:

A pre-existing plasmid containing OleD under the transcriptional control of a pBAD promoter was used. Recombinant protein was expressed in TOP10 $E.$ $coli$ cultures using 0.2% arabinose for induction. Cultures were grown at 30° C., induced during logarithmic phase, and allowed to reach saturation before cells were collected and frozen at −80° C. for future use. Protein was purified using the B-PER 6×His Fusion Protein Spin Purification Kit as described by the user manual. Eluted protein was dialyzed 3× overnight in buffer (50 mM NaCl, 10 mM Tris-HCl, 10 mM $MgCl_2$, 10% glycerol, pH 7.9) using the Slide-A-Lyzer MINI Dialysis Device (Thermo Scientific 88402). Protein purity was verified using Bio-Rad Mini-Protean TGX Gels (456-1096) and protein concentration was identified using the Bradford Protein Assay.

Purified Protein Assays:

Dialyzed recombinant OleD (0.5 μM) was incubated with UDP-Glucose and Kaempferol (0.5 mM) in a buffered solution (50 mM NaCl, 10 mM Tris-HCl, 10 mM MgCl2, pH 7.9). Samples were incubated for 1 hour at 37° C. 1 unit of T4 Phage β-glucosyltransferase and probe DNA at a concentration of 4.5 nM were added, followed by a 2 hour incubation at 37° C. 1 unit of MfeI was then added followed by a 4 hour incubation at 37° C. DNA was visualized on a 2% agarose gel with 0.1% GelGreen Nucleic Acid Stain (Biotium; 41004) and blue light. DNA band intensities were identified using ImageJ. Intensities were compared to protected or unprotected samples.

qPCR Assay Protocol:

PCR tubes were used for most reactions. All incubations were performed at 37° C. Assays were initiated upon the addition of linear DNA (5 nM final concentration) to 4 μl PURExpress Solution A and 3 μl PURExpress Solution B. Samples were incubated at 37° C. for 3 hours prior to addition of UDP-Glucose and chemical (1 mM final concentration) in DMSO. Samples were incubated for an additional 3 hours prior to addition of 1 unit T4 Phage β-glucosyltransferase containing 0.2 nM probe. Samples were incubated an additional 3 hours before DNA was purified using the Zymo DNA Clean and Concentrator Kit. Samples were digested overnight with MfeI prior to analysis. Concentration of intact DNA probe was identified using the iQ SYBR Green Supermix (1708880) with probe DNA as standards. qPCR was carried out on the Bio-Rad iQ5 Multicolor Real-Time PCR Detection System using primers P13 and P14 with the following temperatures; 94° C. 30 seconds followed by 40 cycles of 94° C. 10 seconds and 55° C. for 30 seconds. All results were compared to uncut probe DNA that had been carried through the process as negative controls (considered full recovery of probe).

Fluorescence Assay Protocol:

Assays were performed using 250 nM fluorescent probe (Sequence provided in FIG. 21) in place of the linear probe. Fluorescence was detected using a Tecan Safire$^2$ using the following settings: excitation wavelength 550 nm, emission wavelength 564 nm, excitation bandwidth 5 nm, emission bandwidth 5 nm, Gain (manual) 120, Number of reads 10, FlashMode High Sensitivity, Integration time 100 µs, lag time 0 µs, Z-position 12000 µm, Temperature 37° C. Development of fluorescence after MfeI addition was monitored over an 8 hour period.

LCMS:

Determination of glucosylation was accomplished by means of an LCMS system consisting of an Agilent Technologies 1200 series HPLC with an Agilent Technologies 6520 Accurate Mass qTOF LC/MS. An Eclipse Plus C18 (4.6 mm×100 mm i.d., 3.5-µm packing, Agilent Technologies) reverse-phase column with a guard Zorbax Eclipse Plus C18 column (4.6 cm×12.5 cm, 5 µm packing, Agilent Technologies) was used for separating the samples. Water+ 0.1% Formic Acid and Acetonitrile+0.1% Formic Acid were used as mobile phases at a flow rate of 500 µl/min. The elution gradient water/acetonitrile ratio) was ramped as follows: 98:2 (v/v) (0-2 min), 98:2-5:95 (v/v) linearly (2-17 min), 5:95 (v/v) (17-27 min), and 5:95-98-2 (v/v) (27-28 min). Full scanning mode (50-750 m/z) was used for data acquisition in a positive-ion mode, and the operation parameters were as follows: ESI probe capillary voltage, +3.5 kV with a scan rate of 1.01 scans/second. The nebulizer gas flow rate was 7 L/min. During the analysis two references (121.0509 m/z ($C_5H_4N_4$) and 922.0098 m/z ($C_{18}H_{18}O_6N_3P_3F_{24}$)) were continuously measured to allow constant mass correction.

Samples were prepared directly from cell-free reactions. Equal-molar amounts of chemical and UDP-glucose were incubated with DNA encoding the glucosyltransferase of interest or water in PURExpress for 3 hours at 37° C. 10 µl reactions were combined with 20 µl 100% ethanol, followed by centrifugation at 13.4 krpm for 5 minutes. Supernatant was added to 20 µl water in LCMS vials. 10 µl of reaction/water mixture was injected onto the LCMS per run. Compound presence was identified using MS parent ions.

Results and Discussion

Figure 2B:
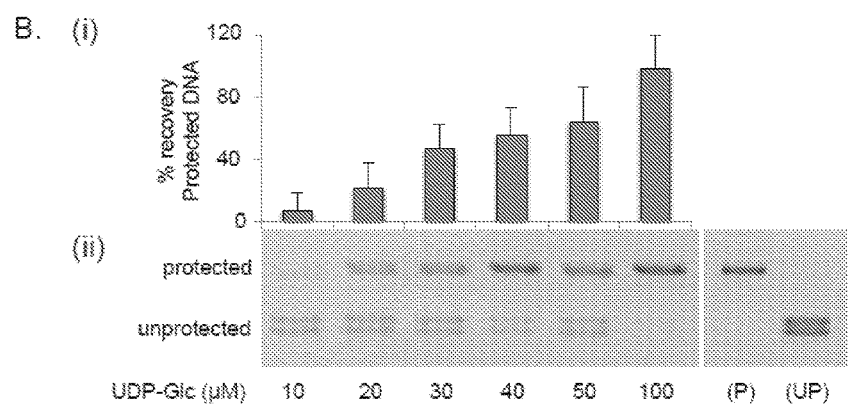
Figure 2C:
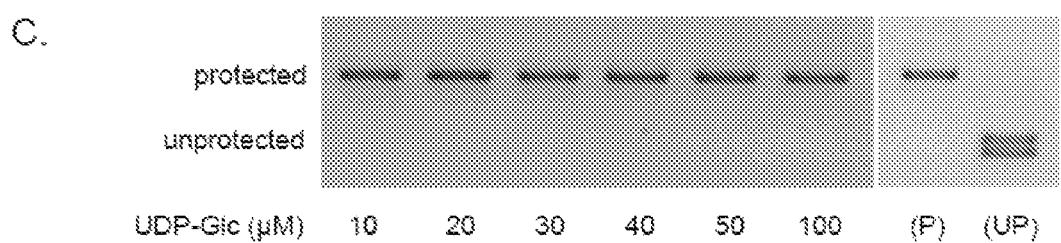
Figure 2D:
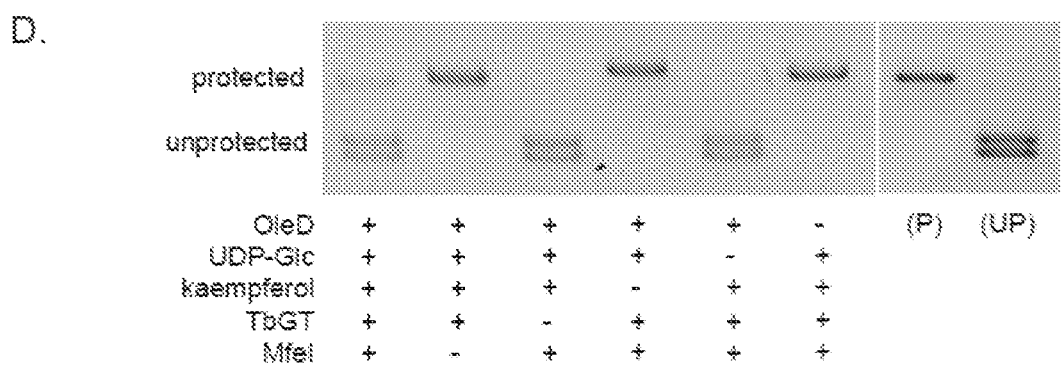
Figure 5:
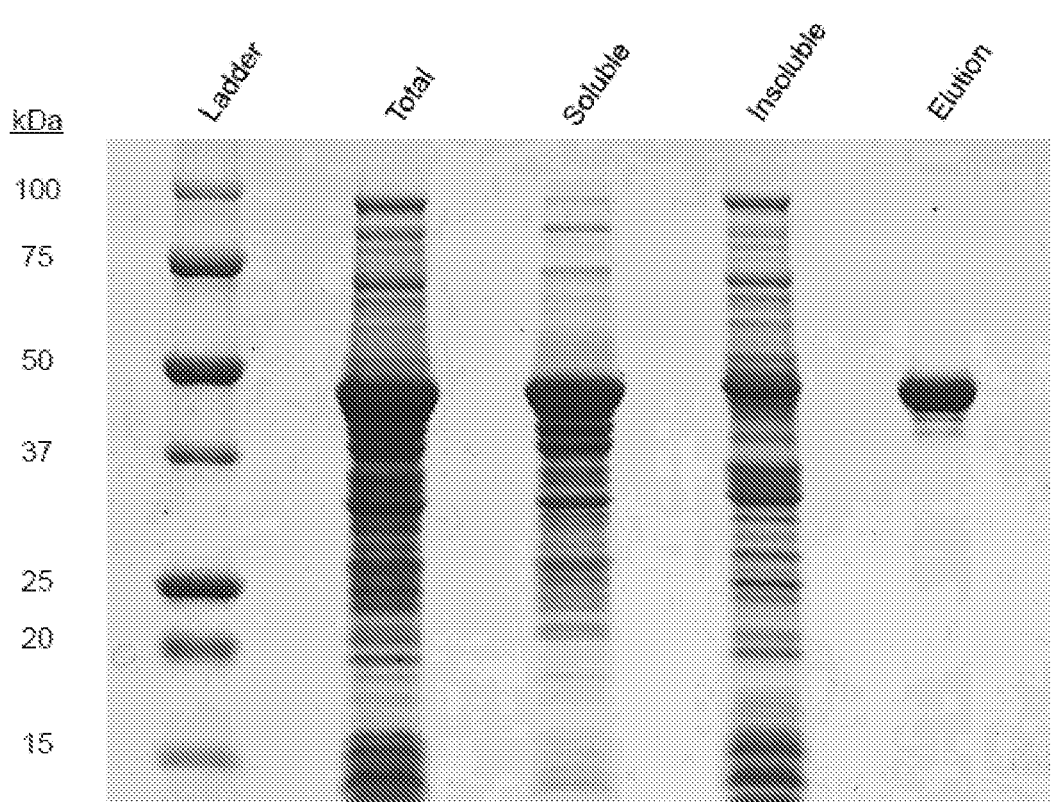
FIG. 5. Protein purification of OleD. Recombinant his-tagged OleD was expressed in TOP10 cells and purified using the B-PER 6×His Fusion Protein Spin Purification Kit. A representative SDS-PAGE gel stained with Coomassie Blue is shown. Key: Total=total protein; Soluble=soluble protein fraction; Insoluble=insoluble protein fraction; Elution=purified protein fraction eluted off of nickel-chelated beads incubated with the soluble protein fraction.

In order to verify that DNA protection using TbGT could be used to follow an enzymatic reaction under conditions amenable to downstream DNA analyses, the ability of recombinant OleD to reduce concentrations of UDP-Glc while in the presence of the substrate kaempferol was first tested. OleD is a well-characterized enzyme of interest to biotechnology due to its ability to glucosylate pharmaceuticals and, as a result, modify their physical properties[2, 32-35]. In particular, OleD has been shown to glucosylate kaempferol. A schematic of this reaction is shown in FIG. 2A. To identify if this reaction could be monitored by modification of DNA, recombinant OleD was purified (FIG. 5) and incubated with 5-hm-cytosine-modified probe DNA (4.5 nM probe DNA containing 2.5 µM modified 5-hm-cytosines), kaempferol (0.5 mM), and UDP-Glc concentrations varying from 10 µM to 1 mM in a buffered solution. As controls, probe DNA was also incubated under identical conditions with no UDP-Glc or 10 mM UDP-Glc. Following TbGT incubation and MfeI digestion, DNA integrity was identified using standard agarose gels (FIG. 2B). As expected, when less UDP-Glc was present at the start of the assay, more probe DNA was digested using the restriction enzyme MfeI. To determine whether an enzymatic reaction—and not spontaneous UDP-Glc hydrolysis—was being followed, the assay was performed under identical conditions using a different UDP-Glc acceptor (4-hydroxybenzoic acid) (FIG. 2C). Under these conditions, no DNA was digested after the UDP-Glc titration enzyme assay was completed. As a final verification, the assay was performed with various component dropouts using 20 µM as starting UDP-Glc concentration (FIG. 2D). As expected, when all components of the assay were present, significant DNA digestion occurred. Under conditions where negligible protection of probe DNA was expected (i.e. no UDP-Glc or TbGT), no protected DNA was identified. In contrast, when protection was expected (no OleD or kaempferol), significant concentrations of protected DNA was found. From this, it was concluded that an enzymatic reaction could be followed using DNA protection from restriction enzyme digestion as the readout of choice.

Figure 3A:
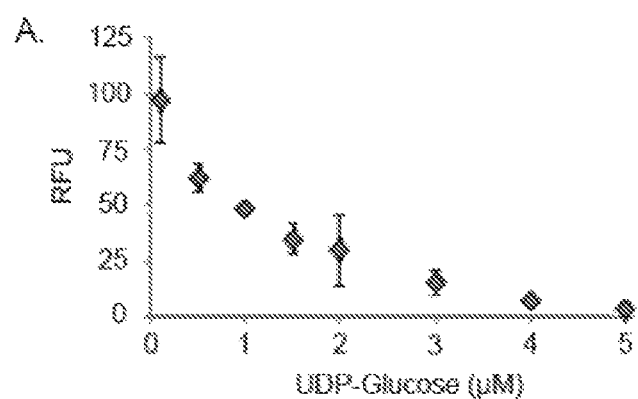
FIG. 3A-FIG. 3D. DNA-Linked Enzyme-Coupled Assay using cell-free transcription/translation system. A. UDP-Glc was titrated into reactions containing 250 nM FRET probe, TbGT, and a cell-free transcription/translation system. After 3 hours incubation at 37° C., probe was digested with MfeI and resulting digests were analyzed using fluorescent spectrometry (n=6, error bars=standard error). B. DNA encoding OleD (5 nM) was incubated in a cell-free transcription/translation system for 3 hours at 37° C., followed by the addition of UDP-Glucose (5 µM) and kaempferol (1 mM). After a subsequent incubation of 3 hours, TbGT and FRET probe (250 nM) were added. Following MfeI addition, fluorescence formation was monitored using fluorometry. Experimental results, as-well-as component knockdown reactions, are plotted as Relative Fluorescent Units (RFU) (n=8; error bars=standard error). C. UDP-Glc was titrated into assays containing probe DNA (0.2 nM), TbGT, and a cell-free transcription/translation system. After 3 hours incubation at 37° C., probe was purified and digested with MfeI. Digests were analyzed using qPCR. Results are plotted as % recovery of probe DNA (recovery of experimental DNA/ recovery of completely protected control DNA) (n=10, error bars=standard error). D. DNA encoding OleD (5 nM) was incubated for 3 hours at 37° C. in a cell-free transcription/translation system, followed by the addition of UDP-Glc (2 µM) and kaempferol (1 mM). After a subsequent incubation of 3 hours, TbGT and probe DNA (0.2 nM) were added. Following probe purification and MfeI digestion, intact DNA probe was identified using qPCR. Experimental results, as-well-as component knockdown reactions, are plotted as % recovery of probe DNA (n=11; error bars=standard error). Key: (+)=presence of component in reaction; (−)=absence of component in reaction. *=p<0.05 vs. no chemical control.
Figure 3B:
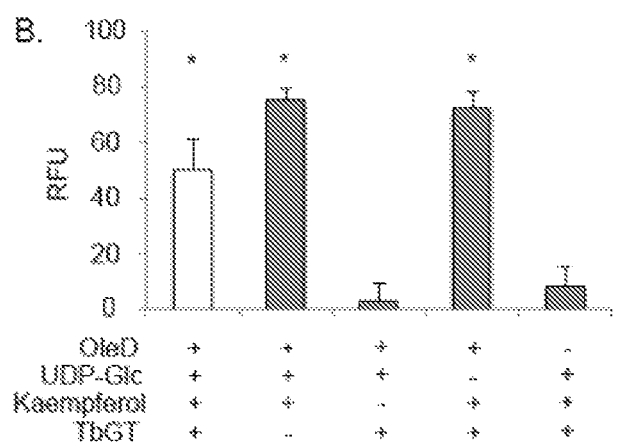

In order to further drive the assay toward a mid-throughput workflow, the assay was modified to utilize non-purified protein derived from a cell-free transcription/translation system as starting material. This assay was first examined using a fluorescent readout (FRET DLEnCA, FIG. 1—FRET workflow). A 38-mer hairpin oligonucleotide containing a Cy3-fluorophore at the 5'-termini and a Black Hole Quencher at the 3'-termini, as-well-as two 5-hm-cytosine residues overlapping an MfeI-recognition site, was purchased; the FRET probe was quenched in its initial state but became fluorescent upon release of the quencher by digestion with MfeI. To determine a threshold for probe protection under conditions amenable to the FRET DLEnCA workflow, UDP-Glc was titrated into mixtures of the cell-free transcription/translation system containing FRET probe (250 nM) and TbGT. After digestion with the restriction enzyme MfeI, the amount of relative fluorescence was monitored by fluorometry (FIG. 3A). A threshold of protection at 5 µM UDP-Glc was identified. This corresponded to a 10:1 molar ratio of UDP-Glc needed to protect the 5-hm-cytosines in the probe. To verify that an enzymatic reaction could be monitored using cell-free transcription/translation-derived protein and the FRET probe as readout, the OleD-catalyzed glucosylation reaction of kaempferol was followed using DNA encoding a promoter and OleD, kaempferol (1 mM), and 5 µM UDP-Glc as starting donor material (FIG. 3B). As expected, when all components of the assay were present, a fluorescent reading of 50 RFU was detected. This was greater than when OleD or kaempferol was omitted from the assay and significant protection of the probe was observed (3 RFU and 8 RFUs respectively). When no protection occurred, as when UDP-Glc or TbGT were omitted from the assay, 75 RFU and 72 RFUs were detected (FIG. 3B). From this it was determined that the FRET-DLEnCA workflow could be used to monitor an enzymatic reaction.

Figure 3C:
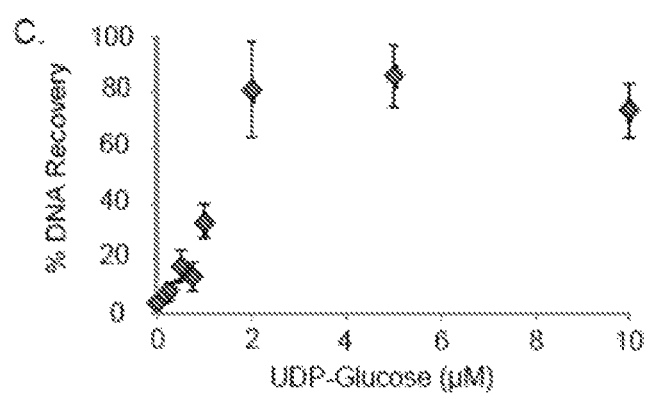
Figure 3D:
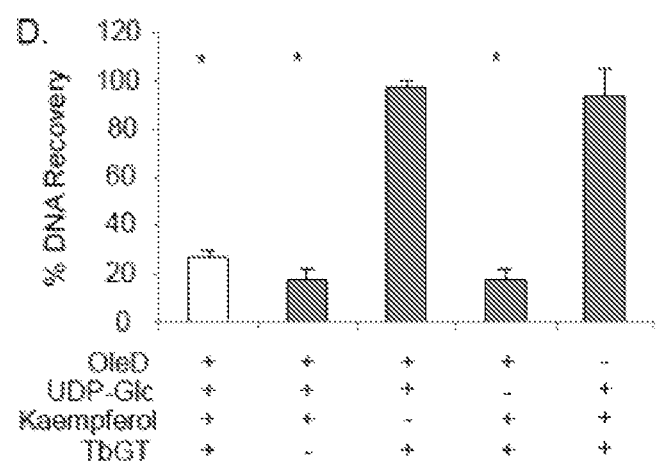

The second DLEnCA workflow developed involved qPCR as a final readout (qPCR DLEnCA, FIG. 1—qPCR workflow). A linear fragment of DNA was modified to contain 5-hm-cytosines throughout. To determine a threshold for probe protection under conditions amenable to the qPCR DLEnCA workflow, UDP-Glc was titrated into mixtures of the cell-free transcription/translation system containing 5-hm-cytosine-modified DNA probe (0.2 nM probe DNA containing 0.1 µM modified 5-hm-cytosines) and TbGT. After digestion with the restriction enzyme MfeI, the amount of intact DNA probe was determined using qPCR (FIG. 3C). As expected, greater starting concentrations of UDP-Glc resulted in greater protection of the probe DNA. A threshold for protection was identified at a 20:1 molar ratio of UDP-Glc to total 5-hm-cytosine in probe DNA; this UDP-Glc amount was used as the starting concentration of UDP-Glc for all qPCR experiments. To test the feasibility of qPCR DLEnCA, OleD was again tested upon the substrate kaempferol (FIG. 3D), using DNA encoding a promoter and OleD as starting material. As expected, when all components of the assay were present, 27% of intact probe DNA was recovered. Under conditions where negligible protection of the probe DNA was expected (i.e. no UDP-Glc or TbGT conditions), only 17% and 18% of the probe was recovered, as compared to 97% and 94% recovery under conditions where substantial protection was expected (no OleD or kaempferol respectively). LCMS was used to verify that glucosylated products were produced under expected conditions (FIG. 6).

Figure 4A:
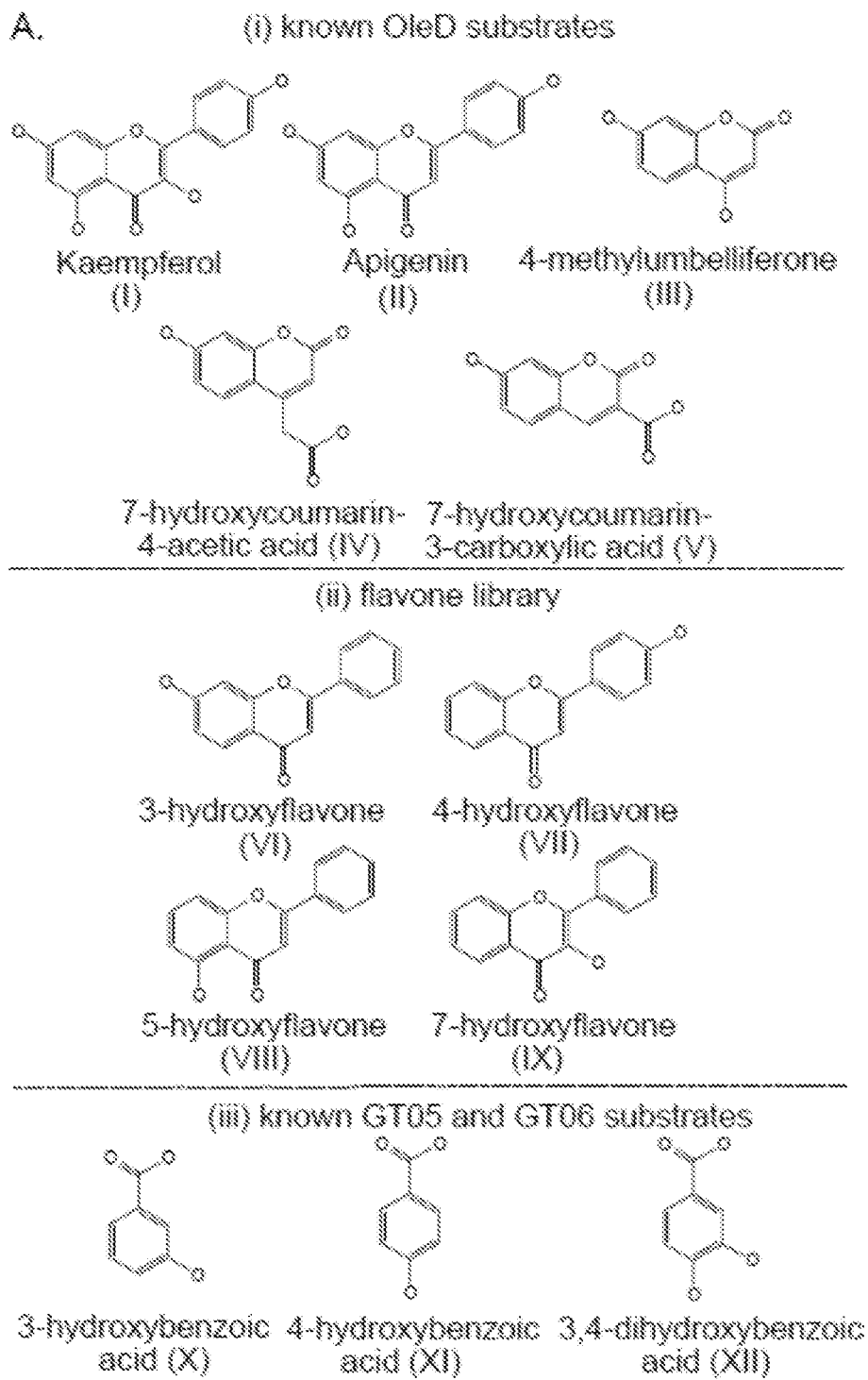
FIG. 4A-FIG. 4D. qPCR DLEnCA and substrate specificity studies. A. Chemicals used as substrates in subsequent assays: (i) known substrates of OleD; (ii) flavone library; (iii) known substrates of GT05 (UGT72B1 (Q9M156)) and GT06 (UGT89B1 (AT1 G73880)). B. DNA encoding OleD (5 nM) was incubated in a cell-free transcription/translation system for 3 hours at 37° C., followed by the addition of chemical (1 mM) and UDP-Glc (2 µM). After a subsequent incubation of 3 hours, TbGT and probe (0.2 nM) were added. After probe purification and MfeI digestion, probe integrity was identified using qPCR. Percent recovery of probe is reported (n=8; error bars=standard error). C. DNA encoding OleD (5 nM) was incubated for 3 hours at 37° C. in a cell-free transcription/translation system, followed by the addition of flavone (1 mM) and UDP-Glc (2 µM). After a subsequent incubation of 3 hours, TbGT and probe (0.2 nM) were added. After probe purification and MfeI addition, probe integrity was identified using qPCR. Percent recovery of probe is reported (n=8; error bars=standard error). D. DNA encoding OleD, GT05, or GT06 (5 nM) were incubated for 3 hours at 37° C. in a cell-free transcription/translation system, followed by the addition of chemical (1 mM) and UDP-Glc (2 µM). After a subsequent incubation of 3 hours, TbGT and probe (0.2 nM) were added. After probe purification and MfeI digestion, probe integrity was identified using qPCR. Percent recovery of probe is reported as a heat map (n=8) (specific recovery figures and percent error can be found in FIG. 16). *=p<0.05 vs. no chemical control.
Figure 4B:
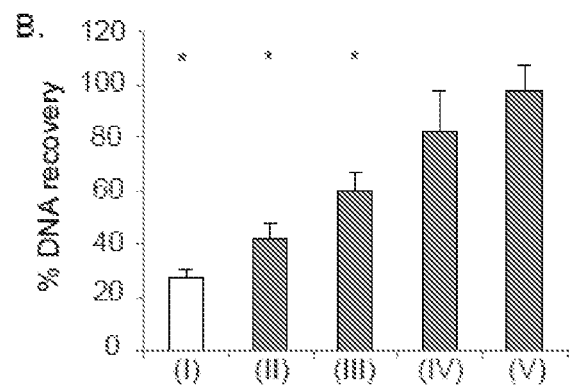
Figure 7A:
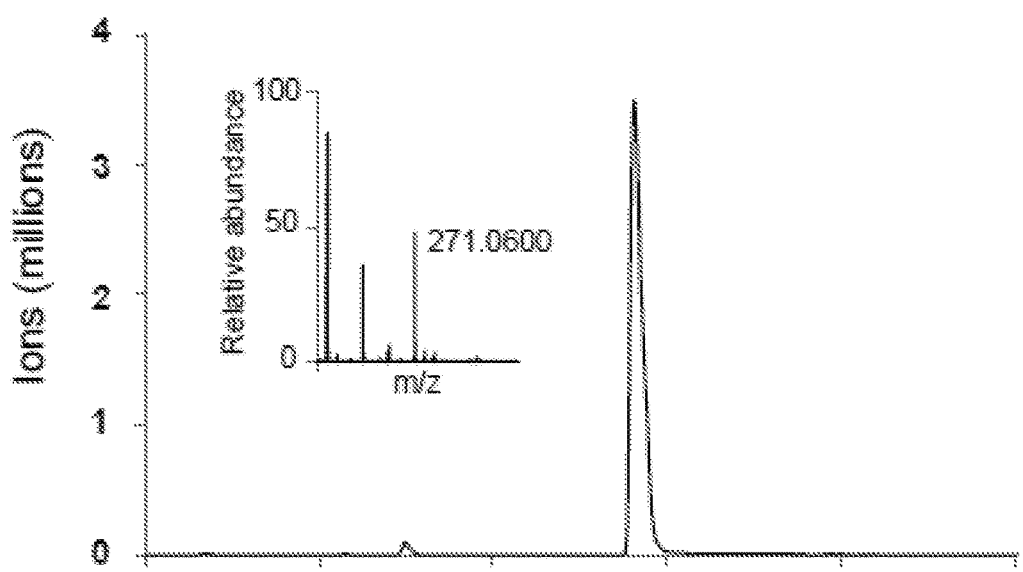
FIG. 7A-FIG. 7B. LC-ESI-MS analysis of apigenin and apigenin glucosides prepared by the OleD-catalyzed glucosylation reaction. A. Starting material elutes at 13.61 minutes and has a molecular ion [M+H]+ at m/z 271.06, representing apigenin. B. Reaction of OleD with apigenin. Unreacted apigenin elutes at 13.61 minutes. GT-catalyzed products elutes at 11.32 and 10.96 minutes. Reactant has a molecular ion [M+H]+ at m/z 433.11, representing the apigenin glucoside. Molecular mass of the molecular ion [M+H]+ of apigenin glucoside equals the sum of apigenin and one molecule of glucose with a gain of a hydrogen.
Figure 7B:
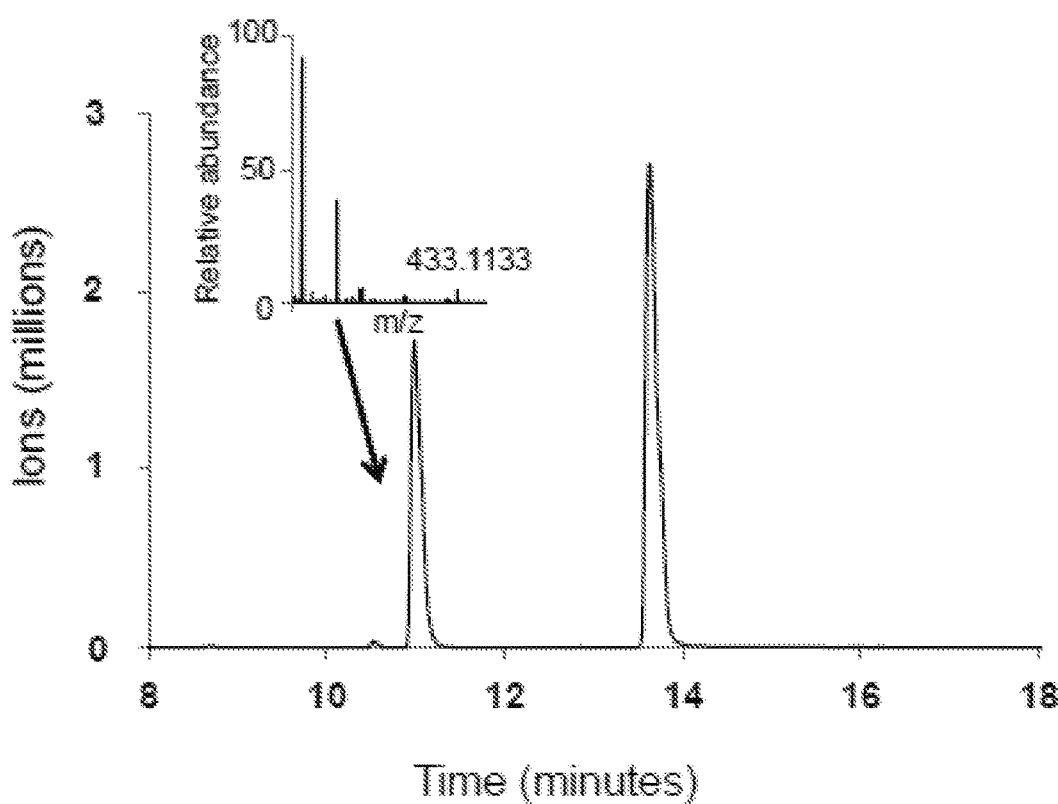
Figure 8A:
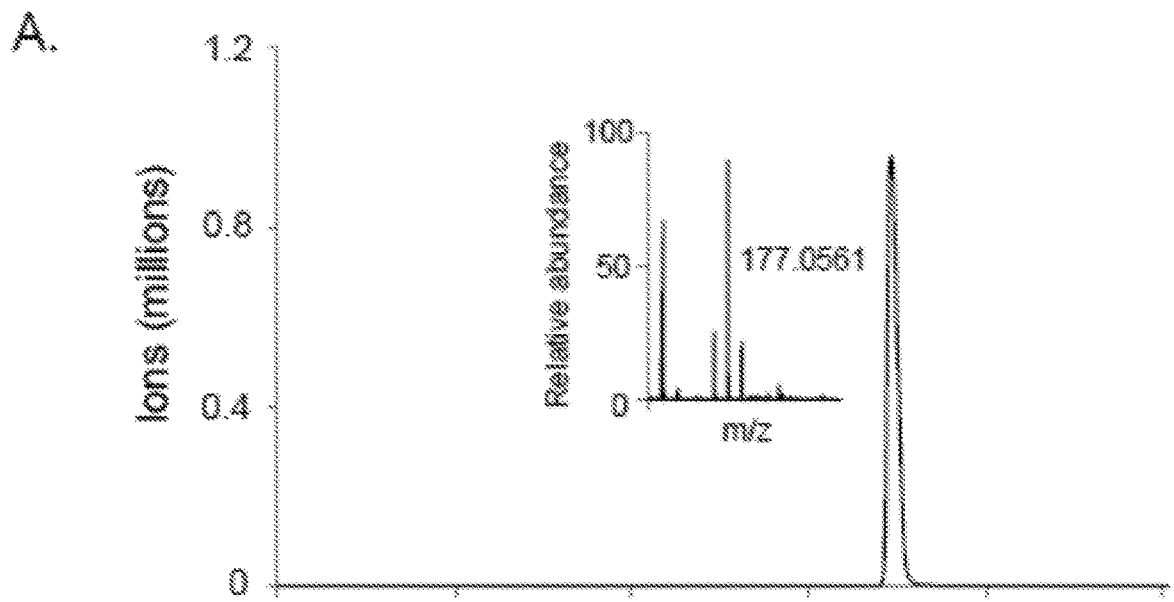
FIG. 8A-FIG. 8B. LC-ESI-MS analysis of 4-methylumbelliferone and 4-methylumbelliferone glucosides prepared by the OleD-catalyzed glucosylation reaction. A. Starting material elutes at 12.90 minutes and has a molecular ion [M+H]+ at m/z 177.06, representing 4-methylumbelliferone. B. Reaction of OleD with 4-methylumbelliferone. Unreacted 4-methylumbelliferone elutes at 12.90 minutes. GT-catalyzed product elutes at 10.15 minutes and has a molecular ion [M+H]+ at m/z 339.11, representing the 4-methylumbelliferone glucoside. Fragment at m/z 177.06 represents 4-methylumbelliferone. Molecular mass of the molecular ion [M+H]+ of 4-methylumbelliferone glucoside equals the sum of 4-methylumbelliferone and one molecule of glucose with a gain of a hydrogen.
Figure 8B:
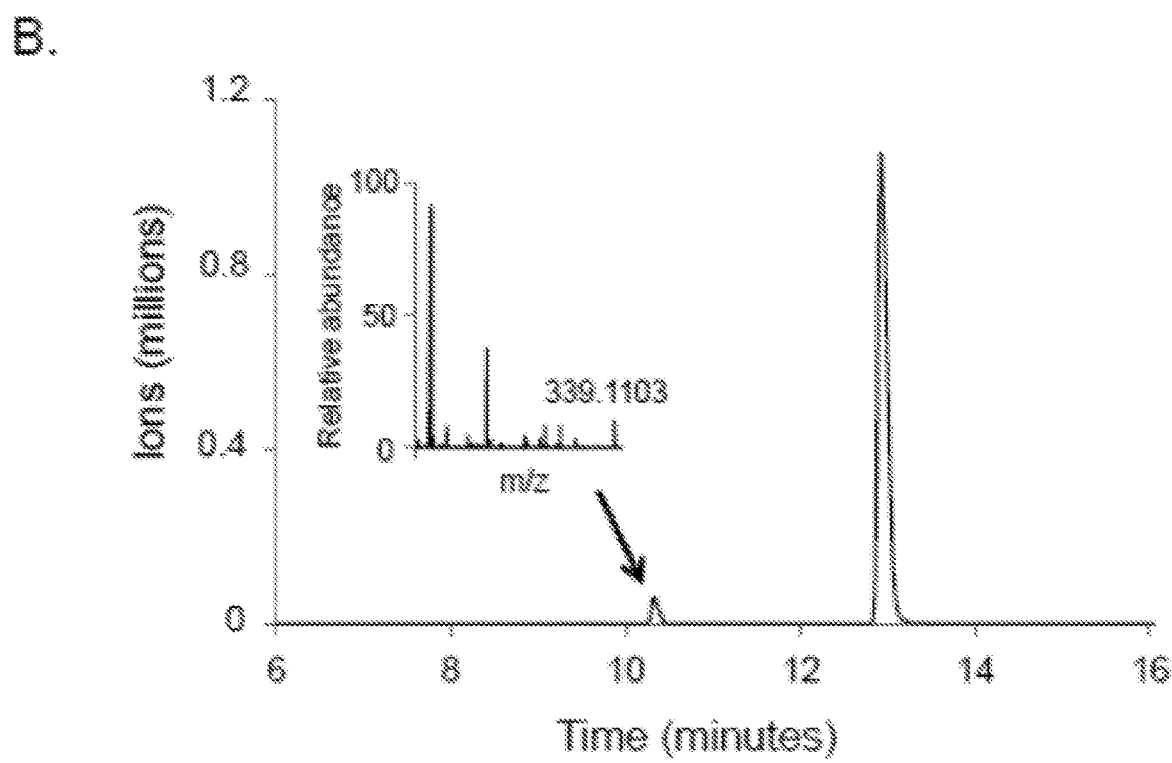
Figure 9A:
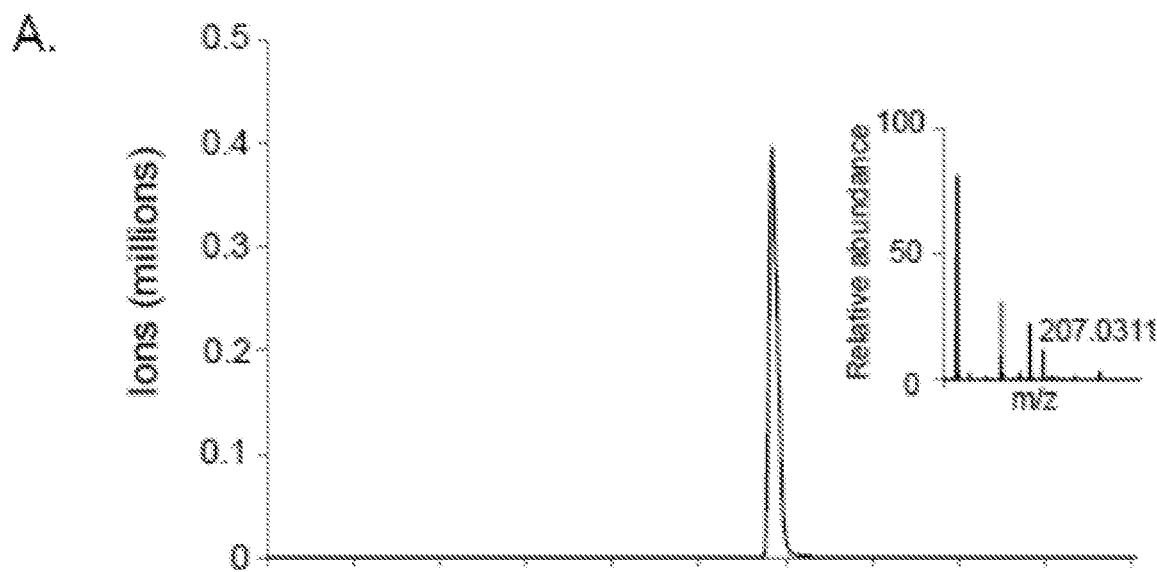
FIG. 9A-FIG. 9B. LC-ESI-MS analysis of 7-hydroxycoumarin-3-carboxylic acid prepared by the OleD-catalyzed glucosylation reaction. A. Starting material elutes at 11.85 minutes and has a molecular ion [M+H]+ at m/z 207.03, representing 7-hydroxycoumarin-3-carboxylic acid. B. Reaction of OleD with 7-hydroxycoumarin-3-carboxylic acid. Unreacted 7-hydroxycoumarin-3-carboxylic acid elutes at 11.85 minutes.
Figure 9B:
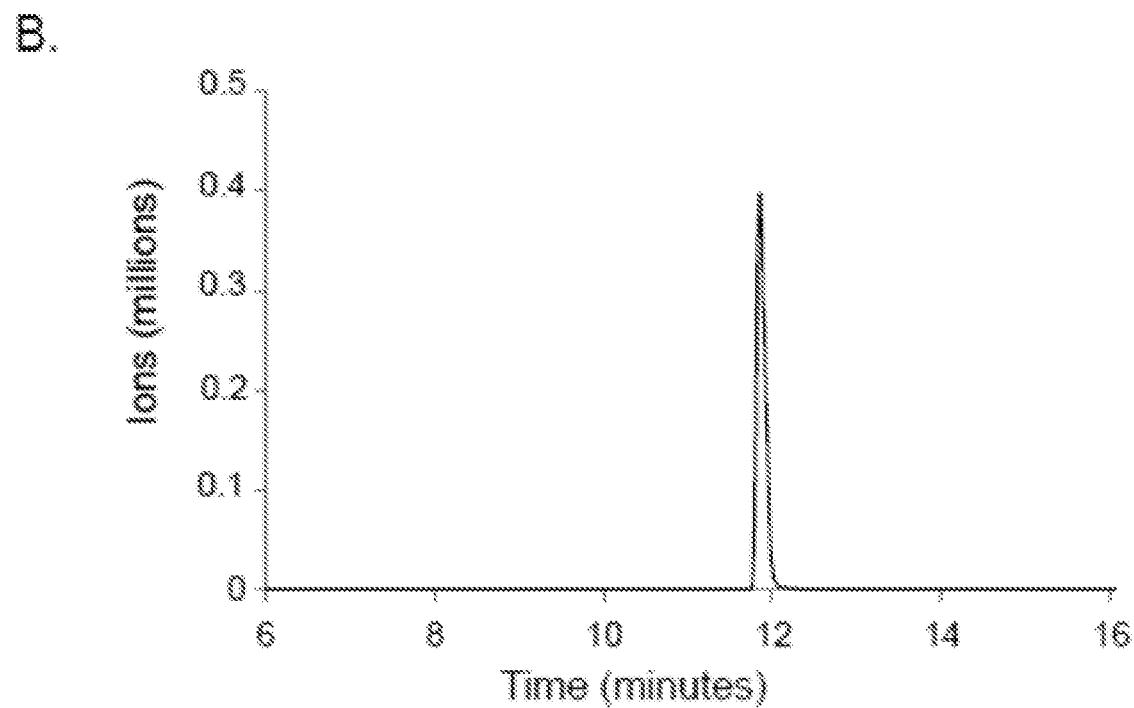
Figure 10A:
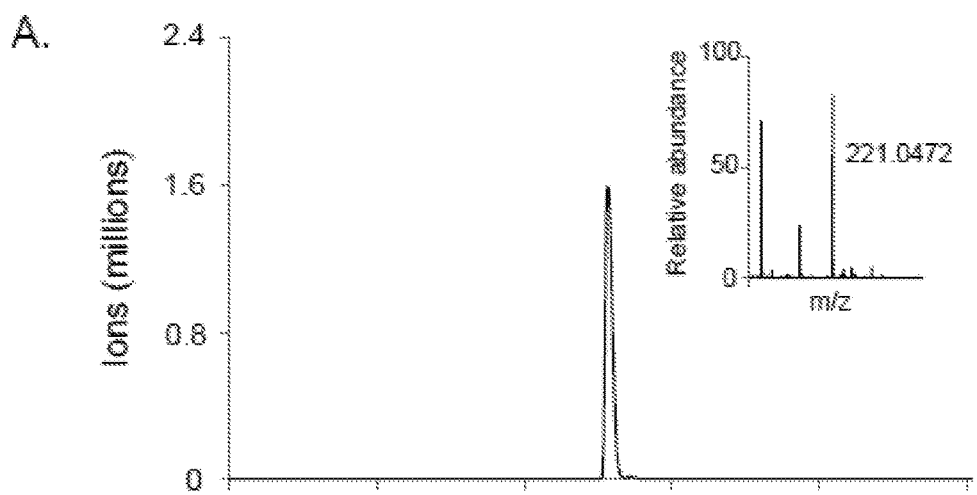
FIG. 10A-FIG. 10B. LC-ESI-MS analysis of 7-hydroxycoumarin-4-acetic acid prepared by the OleD-catalyzed glucosylation reaction. A. Starting material elutes at 11.12 minutes and has a molecular ion [M+H]+ at m/z 221.05, representing 7-hydroxycoumarin-4-acetic acid. B. Reaction of OleD with 7-hydroxycoumarin-4-acetic acid. Unreacted 7-hydroxycoumarin-4-acetic acid elutes at 11.12 minutes.
Figure 10B:
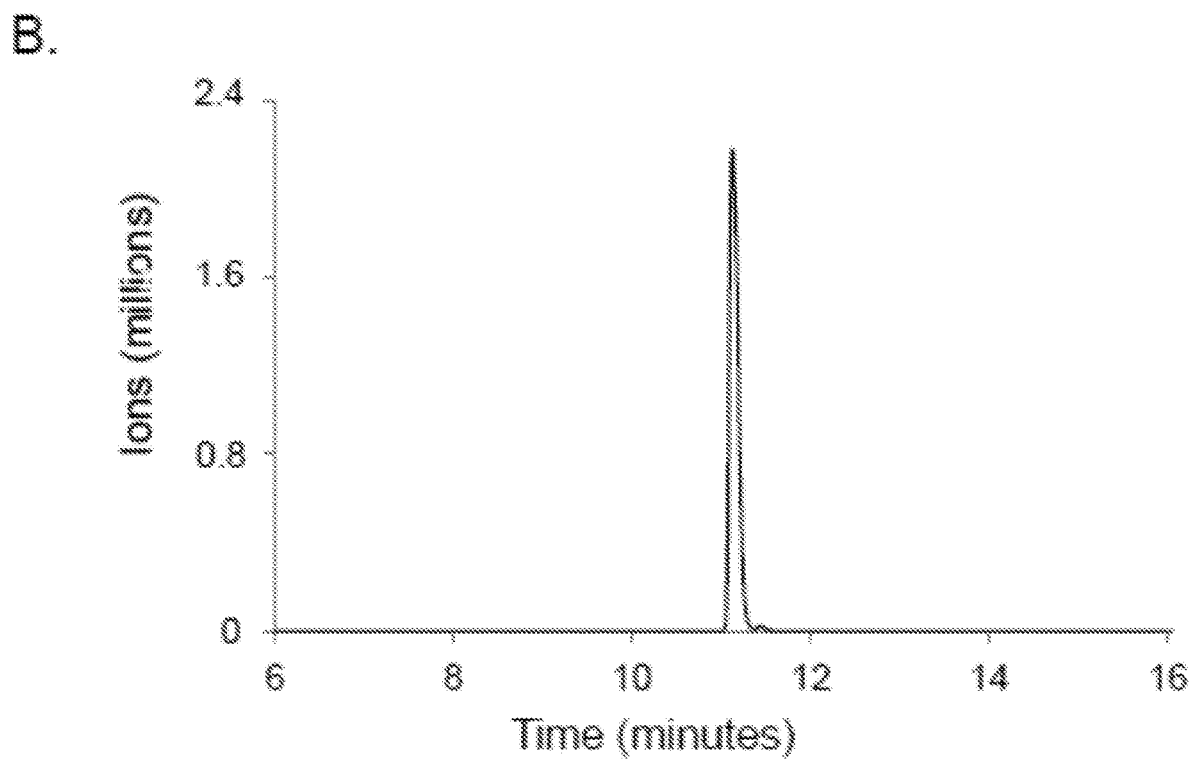
Figure 11A:
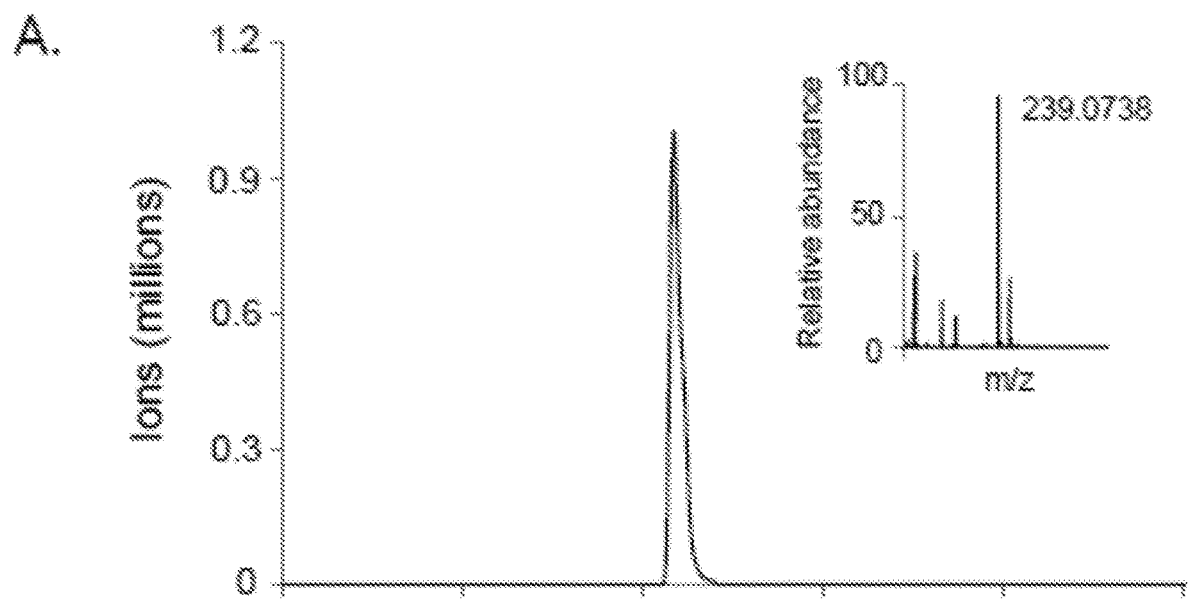
FIG. 11A-FIG. 11B. LC-ESI-MS analysis of 3-hydroxyflavone and 3-hydroxyflavone glucosides prepared by the OleD-catalyzed glucosylation reaction. A. Starting material elutes at 17.88 minutes and has a molecular ion [M+H]+ at m/z 239.07, representing 3-hydroxyflavone. B. Reaction of OleD with 3-hydroxyflavone. Unreacted 3-hydroxyflavone elutes at 17.88 minutes. GT-catalyzed product elutes at 12.56 minutes and has a molecular ion [M+H]+ at m/z 401.13, representing the 3-hydroxyflavone glucoside. Molecular mass of the molecular ion [M+H]+ of 3-hydroxyflavone glucoside equals the sum of 3-hydroxyflavone and one molecule of glucose with a gain of a hydrogen.
Figure 11B:
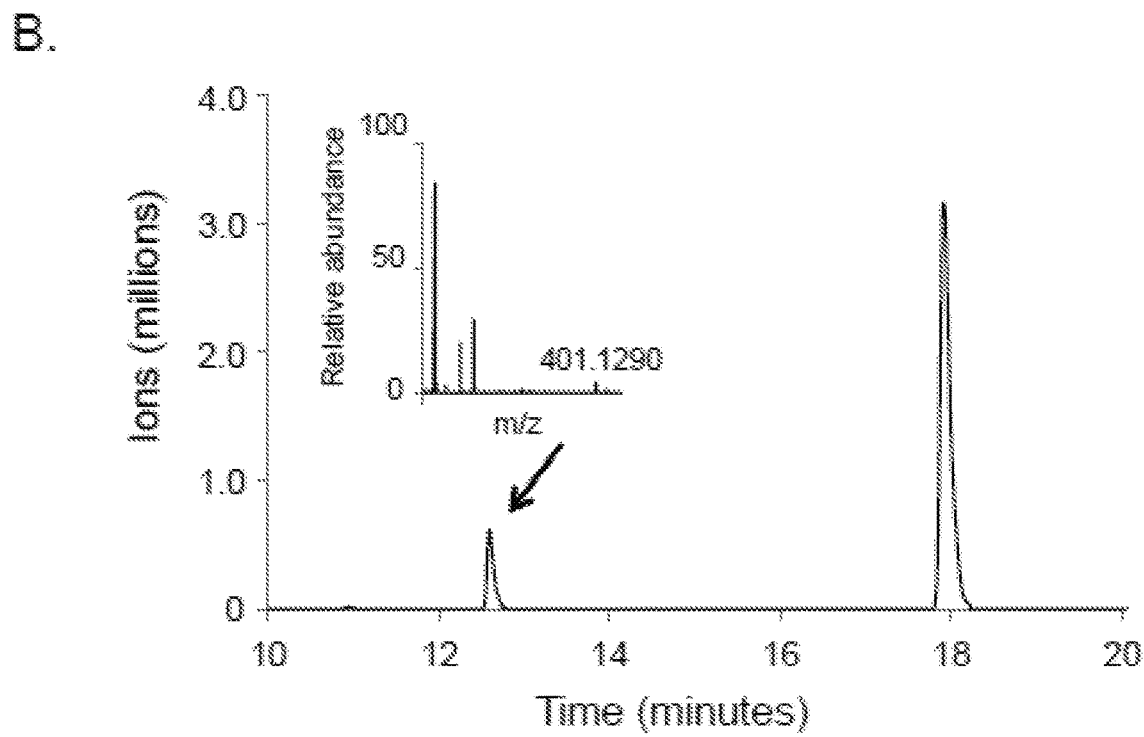
Figures 12A, 12B:
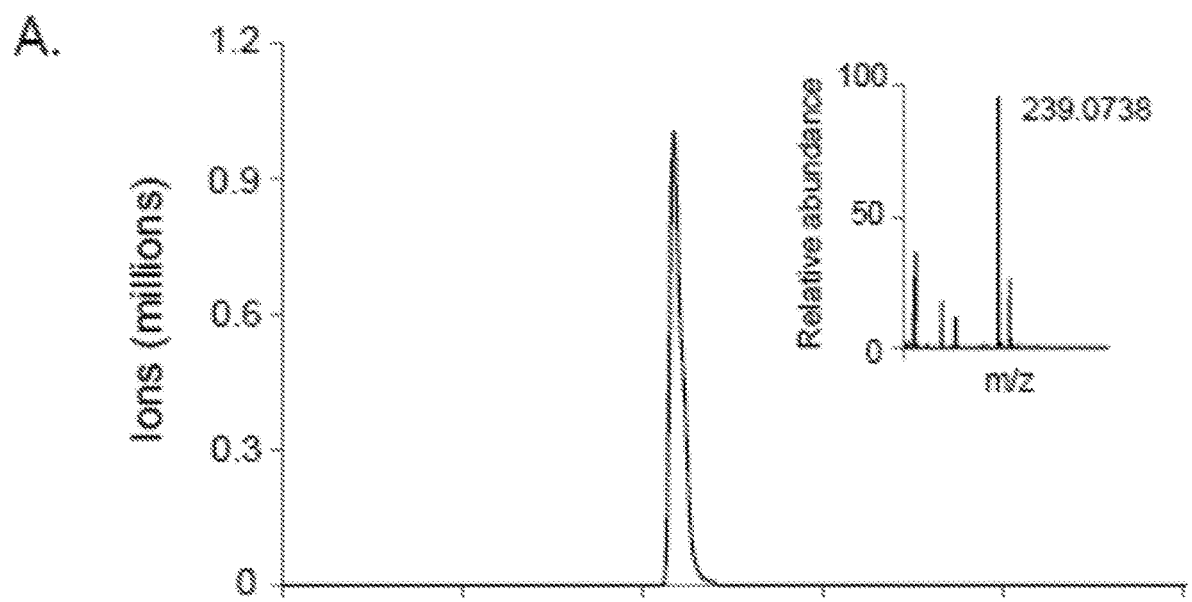
FIG. 12A-FIG. 12B. LC-ESI-MS analysis of 4-hydroxyflavone prepared by the OleD-catalyzed glucosylation reaction. A. Starting material elutes at 14.34 minutes and has a molecular ion [M+H]+ at m/z 239.07, representing 4-hydroxyflavone. B. Reaction of OleD with 4-hydroxyflavone. Unreacted 4-hydroxyflavone elutes at 14.34 minutes.
Figure 13A:
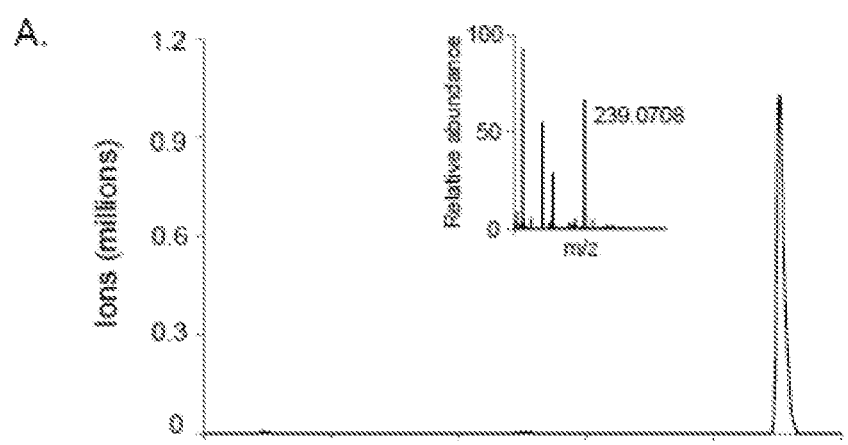
FIG. 13A-FIG. 13B. LC-ESI-MS analysis of 5-hydroxyflavone prepared by the OleD-catalyzed glucosylation reaction. A. Starting material elutes at 19.02 minutes and has a molecular ion [M+H]+ at m/z 239.07, representing 5-hydroxyflavone. B. Reaction of OleD with 5-hydroxyflavone. Unreacted 5-hydroxyflavone acid elutes at 19.02 minutes.
Figure 13B:
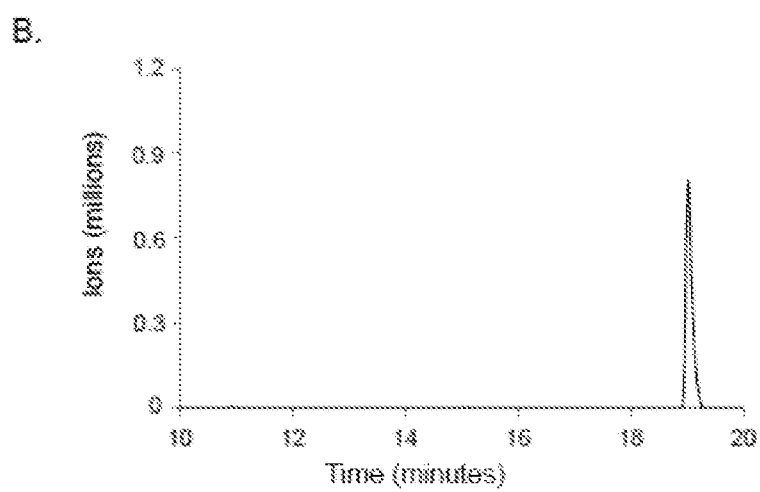
Figure 14A:
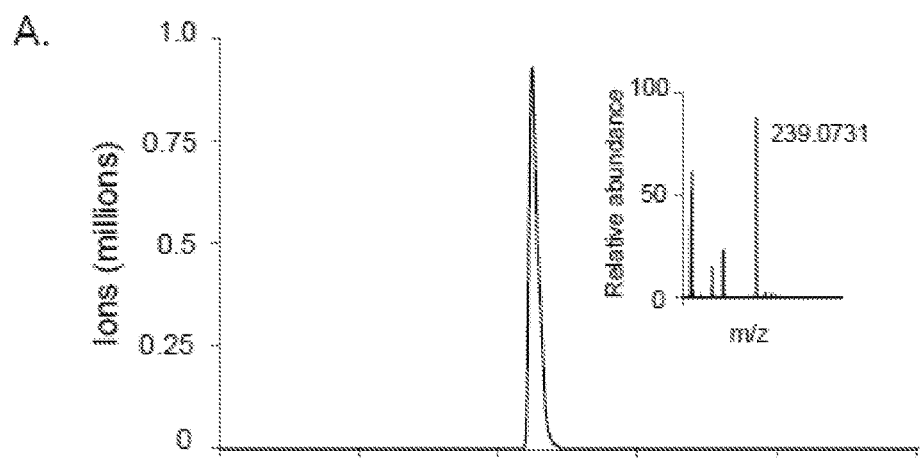
FIG. 14A-FIG. 14B. LC-ESI-MS analysis of 7-hydroxyflavone and 7-hydroxyflavone glucosides prepared by the OleD-catalyzed glucosylation reaction. A. Starting material elutes at 14.48 minutes and has a molecular ion [M+H]+ at m/z 239.07, representing 7-hydroxyflavone. B. Reaction of OleD with 7-hydroxyflavone. Unreacted 7-hydroxyflavone elutes at 14.48 minutes. GT-catalyzed product elutes at 11.56 minutes and has a molecular ion [M+H]+ at m/z 401.13, representing the 7-hydroxyflavone glucoside. Molecular mass of the molecular ion [M+H]+ of 7-hydroxyflavone glucoside equals the sum of 7-hydroxyflavone and one molecule of glucose with a gain of a hydrogen.
Figure 14B:
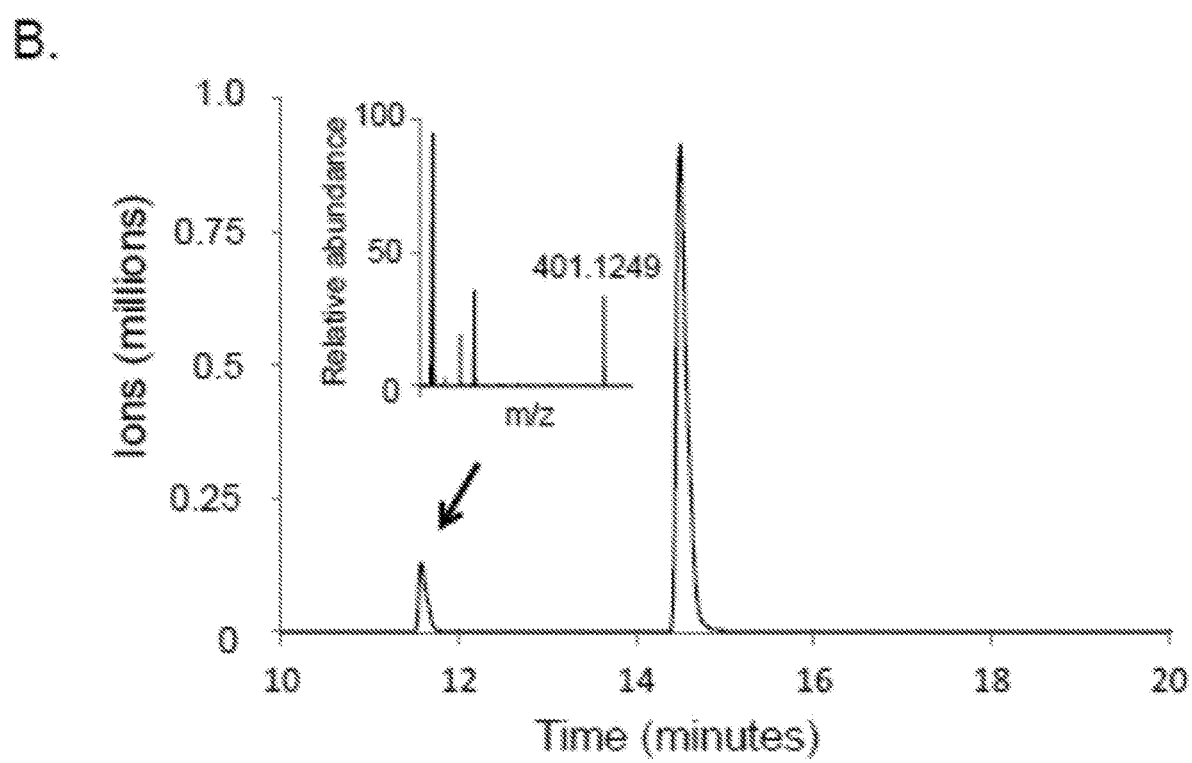
Figure 15A:
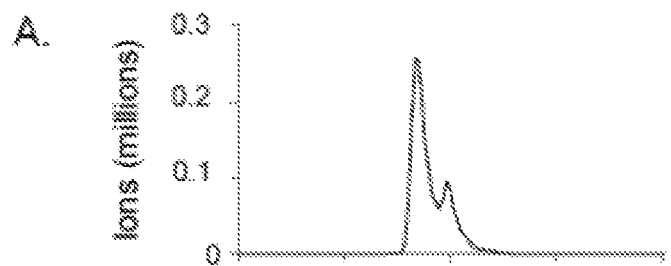
FIG. 15A-FIG. 15D. LC analysis of OleD-catalyzed glucosylation reaction with kaempferol vs. glucoside standards. A. Reaction of OleD with kaempferol. GT-catalyzed products elute at 11.32 and 11.39 minutes. B. Kaempferol-3-glucoside standard. Standard elutes at 11.32 minutes. C. Kaempferol-7-glucoside standard. Standard elutes at 11.39 minutes. D. Mixture of kaempferol-glucosides. Standard peaks elute at 11.32 and 11.39 minutes.
Figure 15B:
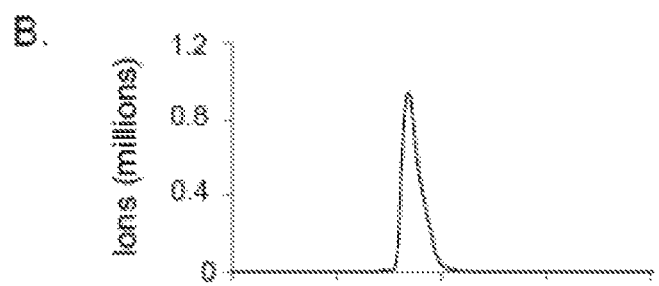
Figure 15C:
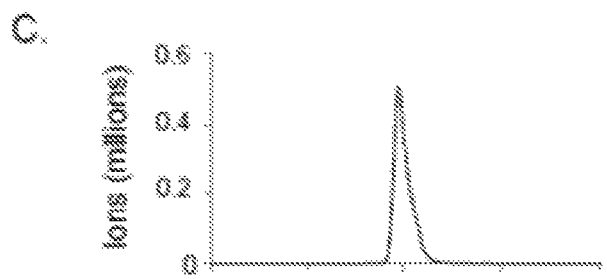
Figure 15D:
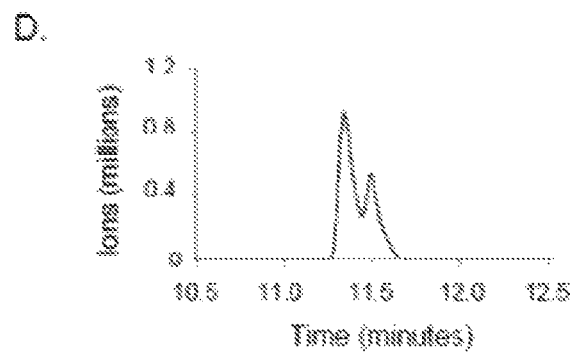
Figure 16:
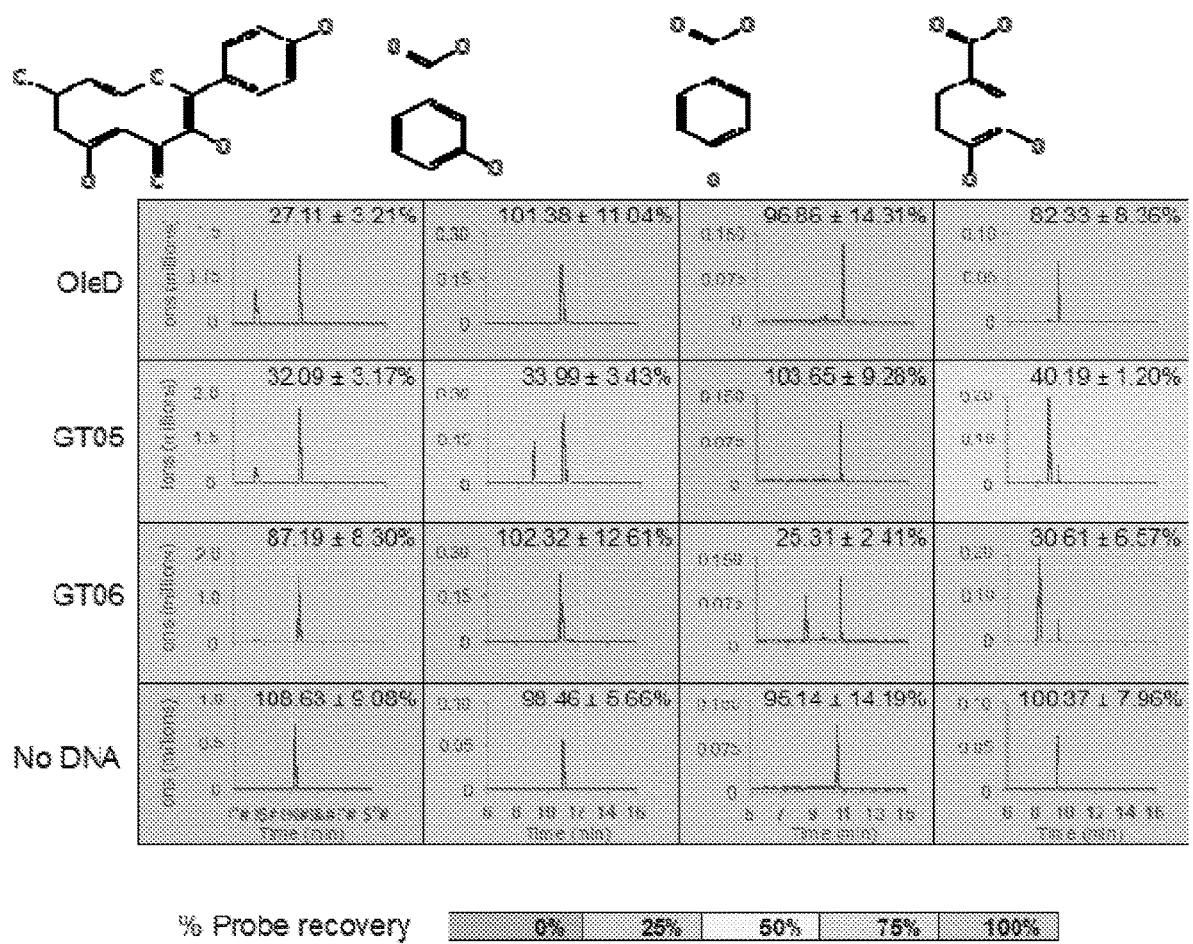
FIG. 16. Heat map depicting reactions between OleD, GT05, or GT06 with kaempferol, 3-hydroxybenzoic acid, 4-hydroxybenzoic acid, or 3,4-dihydroxybenzoic acid. Heat map representing the % probe recovery of GT-catalyzed glucosylation reactions with various chemicals. The number in the top right-hand corner of each cell corresponds to the average probe recovery±standard error of the given reaction (n=8). LCMS plot in each cell is a representative LCMS plot for each GT-catalyzed reaction.
Figure 17A:
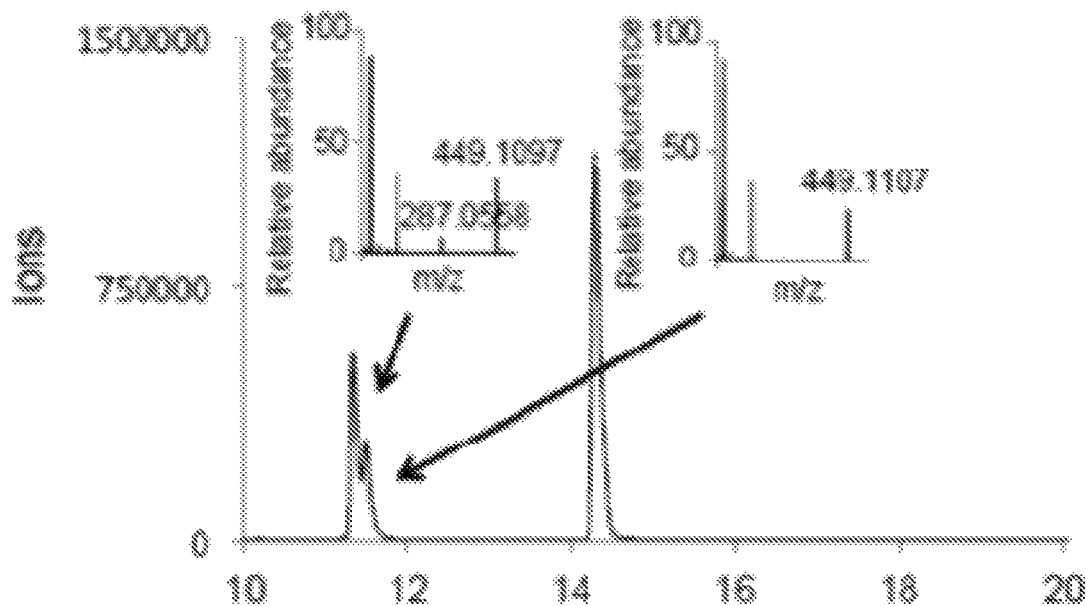
FIG. 17A-FIG. 17D. LC-ESI-MS analysis of kaempferol and kaempferol glucosides prepared by the OleD, GT05, or GT06-catalyzed glucosylation reactions. A. Reaction of OleD with kaempferol. Unreacted kaempferol elutes at 14.35 minutes. GT-catalyzed products elutes at 11.32 and 11.39 minutes. Both products have a molecular ion [M+H]+ at m/z 449.11, representing the kaempferol glucoside. Fragment at m/z 287.06 represents kaempferol. B. Reaction of GT05 with kaempferol. Unreacted kaempferol elutes at 14.35 minutes. GT-catalyzed products elute at 11.32, 11.39, and 11.55 minutes. All products have a molecular ion [M+H]+ at m/z 449.11, representing the kaempferol glucoside. Fragment at m/z 287.06 represents kaempferol. C. Reaction of GT06 with kaempferol. Unreacted kaempferol elutes at 14.35 minutes and has a molecular ion [M+H]+ at m/z 287.06, representing kaempferol. D. Kaempferol pre-GT-catalyzed glucosylation reaction. Starting material elutes at 14.35 minutes and has a molecular ion [M+H]+ at m/z 287.06, representing kaempferol. Molecular mass of the molecular ion [M+H]+ of kaempferol glucosides equals the sum of kaempferol and one molecule of glucose with a gain of a hydrogen.
Figure 17B:
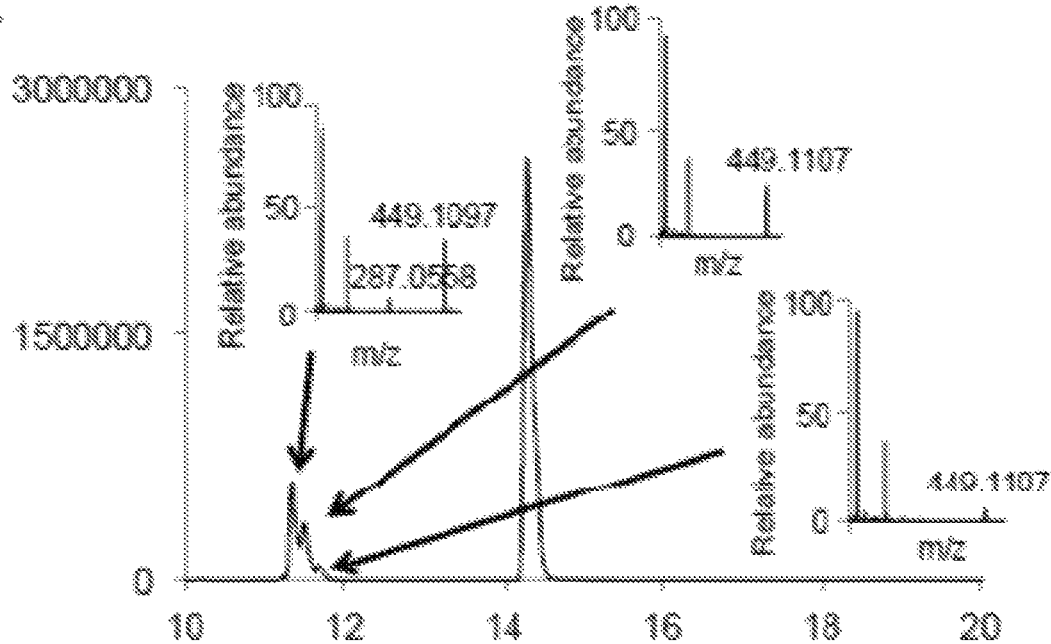
Figure 17C:
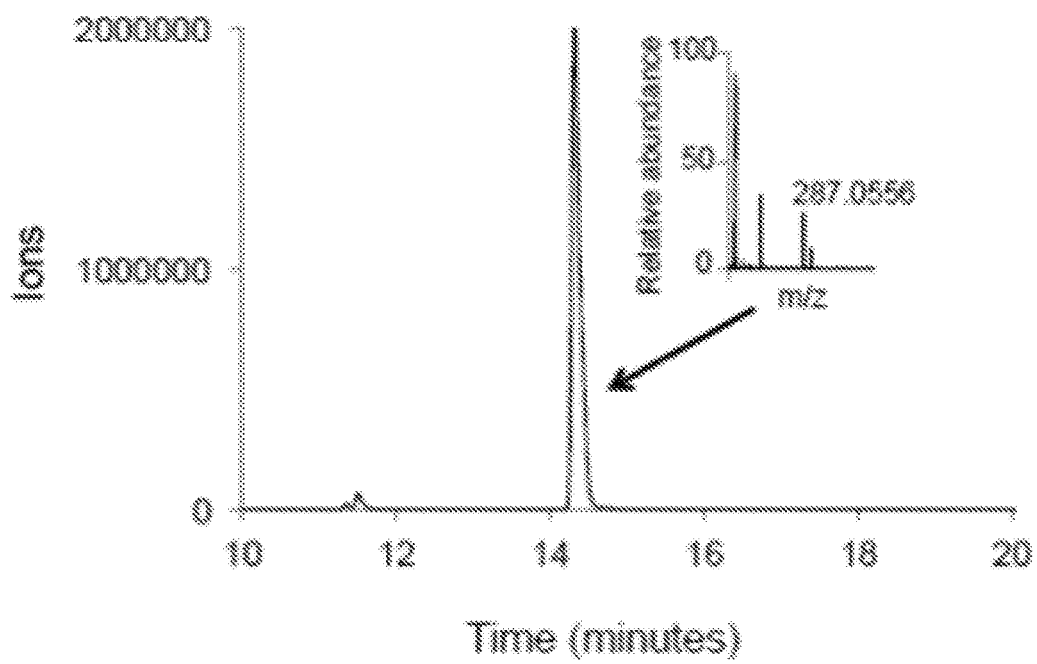
Figure 17D:
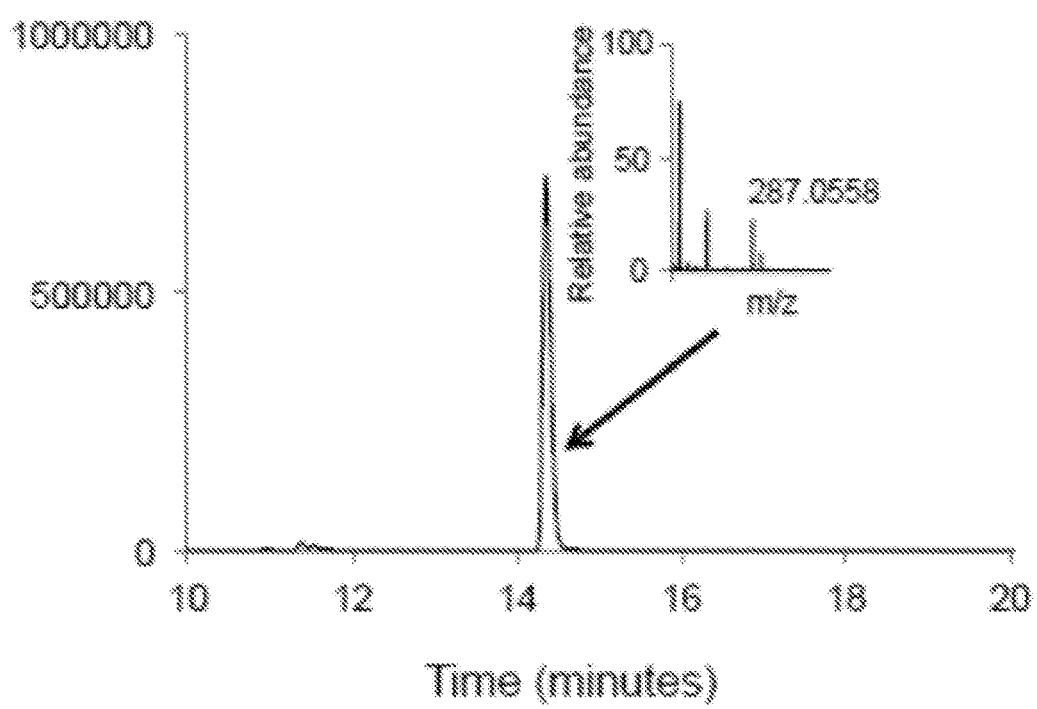
Figure 18A:
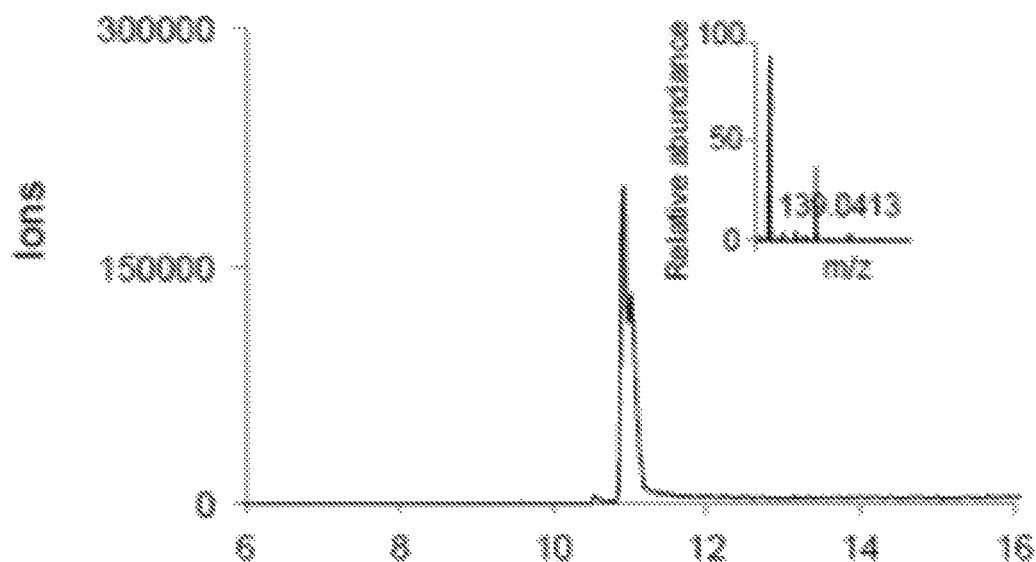
FIG. 18A-FIG. 18D. LC-ESI-MS analysis of 3-hydroxybenzoic acid and 3-hydroxybenzoic acid glucoside prepared by the OleD, GT05, or GT06-catalyzed glucosylation reactions. A. Reaction of OleD with 3-hydroxybenzoic acid. Unreacted 3-hydroxybenzoic acid elutes at 10.89 minutes and has a molecular ion [M+H]+ at m/z 139.04. B. Reaction of GT05 with 3-hydroxybenzoic acid. Unreacted 3-hydroxybenzoic acid elutes at 10.89 minutes. GT-catalyzed product elutes at 8.97 minutes and has a molecular ion [M+H]+ at m/z 301.09, representing the 3-hydroxybenzoic acid glucoside. C. Reaction of GT06 with 3-hydroxybenzoic acid. Unreacted 3-hydroxybenzoic acid elutes at 10.89 minutes and has a molecular ion [M+H]+ at m/z 139.04. D. 3-hydroxybenzoic acid pre-GT-catalyzed glucosylation reaction. Starting material elutes at 10.89 minutes and has a molecular ion [M+H]+ at m/z 139.04, representing 3-hydroxybenzoic acid. Molecular mass of the molecular ion [M+H]+ of 3-hydroxybenzoic acid glucoside equals the sum of 3-hydroxybenzoic acid and one molecule of glucose with a gain of a hydrogen.
Figure 18B:
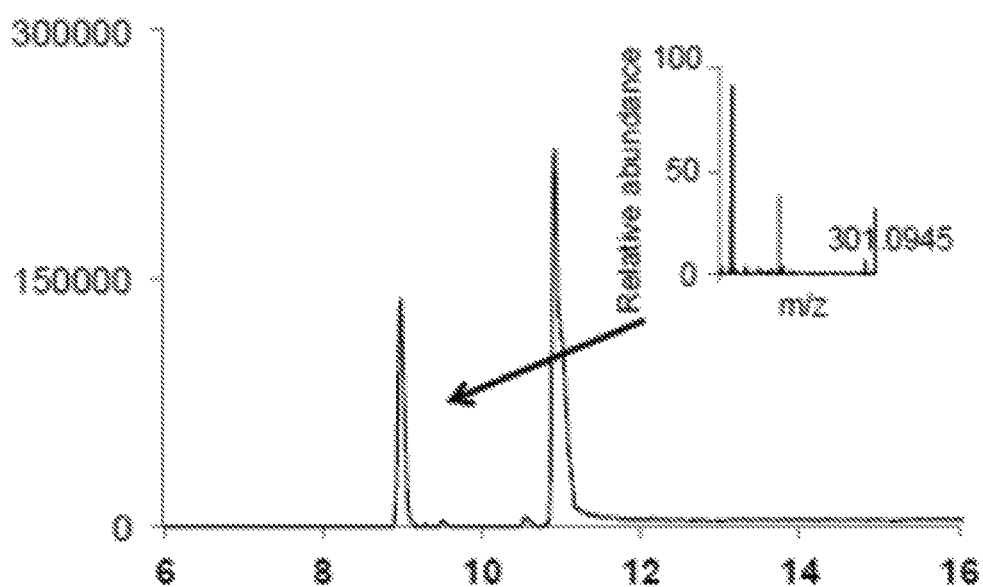
Figure 18C:
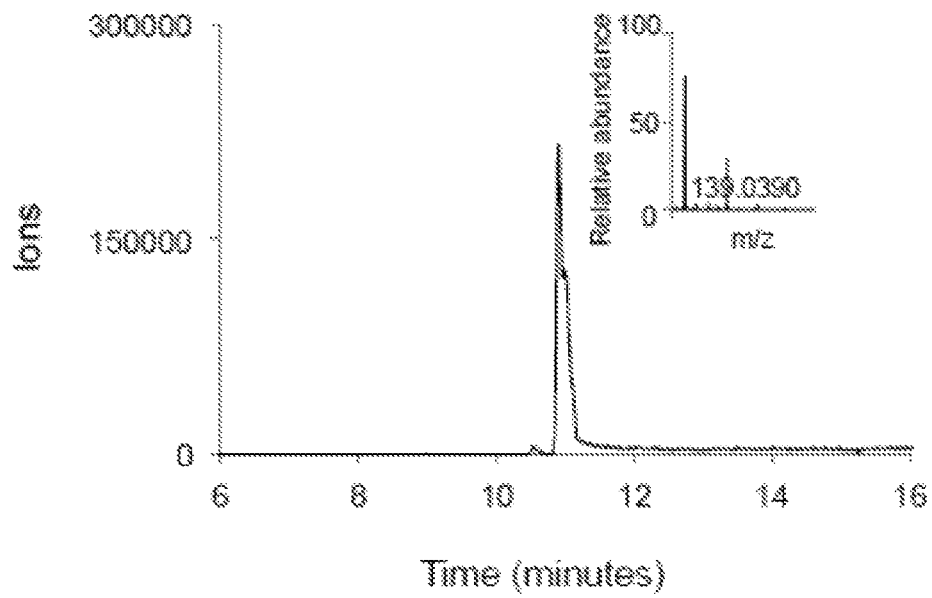
Figure 18D:
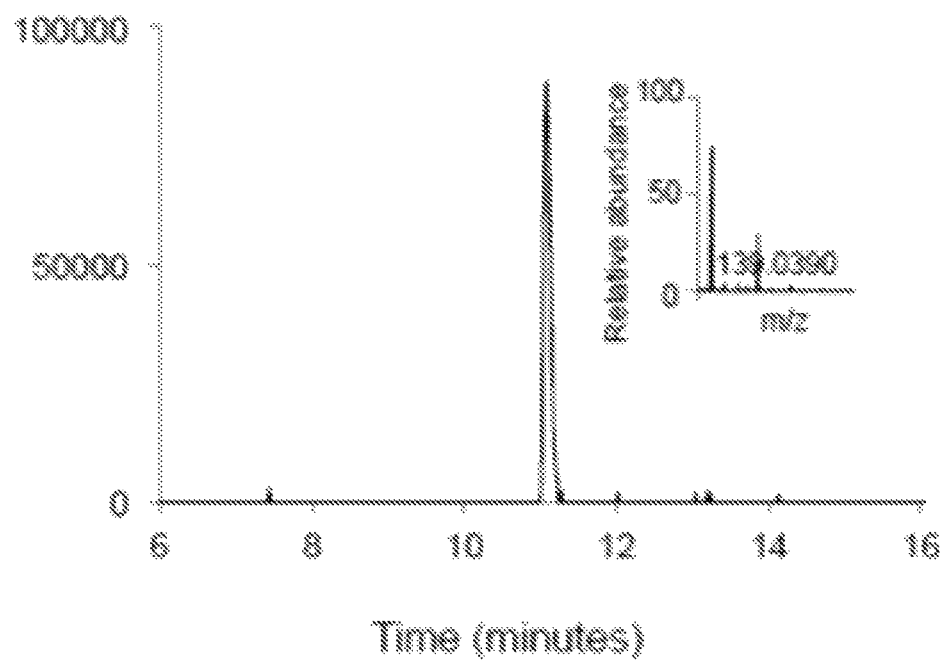
Figure 19A:
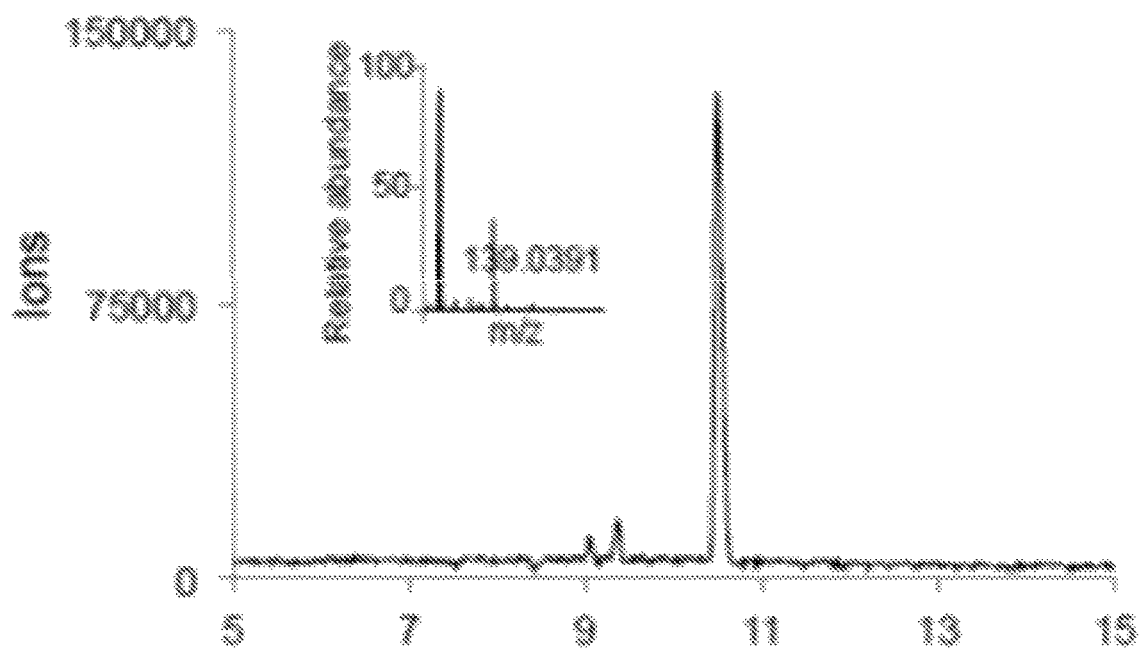
FIG. 19A-FIG. 19D. LC-ESI-MS analysis of 4-hydroxybenzoic acid and 4-hydroxybenzoic acid glucoside prepared by the OleD, GT05, or GT06-catalyzed glucosylation reactions. A. Reaction of OleD with 4-hydroxybenzoic acid. Unreacted 4-hydroxybenzoic acid elutes at 10.5 minutes and has a molecular ion [M+H]+ at m/z 139.04. B. Reaction of GT05 with 4-hydroxybenzoic acid. Unreacted 4-hydroxybenzoic acid elutes at 10.5 minutes and has a molecular ion [M+H]+ at m/z 139.04. C. Reaction of GT06 with 4-hydroxybenzoic acid. Unreacted 4-hydroxybenzoic acid elutes at 10.89 minutes and has a molecular ion [M+H]+ at m/z 139.04. GT-catalyzed product elutes at 8.24 minutes and has a molecular ion [M+H]+ at m/z 301.09, representing the 4-hydroxybenzoic acid glucoside. D. 4-hydroxybenzoic acid pre-GT-catalyzed glucosylation reaction. Starting material elutes at 10.5 minutes and has a molecular ion [M+H]+ at m/z 139.04, representing 4-hydroxybenzoic acid. Molecular mass of the molecular ion [M+H]+ of 4-hydroxybenzoic acid glucosides equals the sum of 4-hydroxybenzoic acid and one molecule of glucose with a gain of a hydrogen.
Figure 19B:
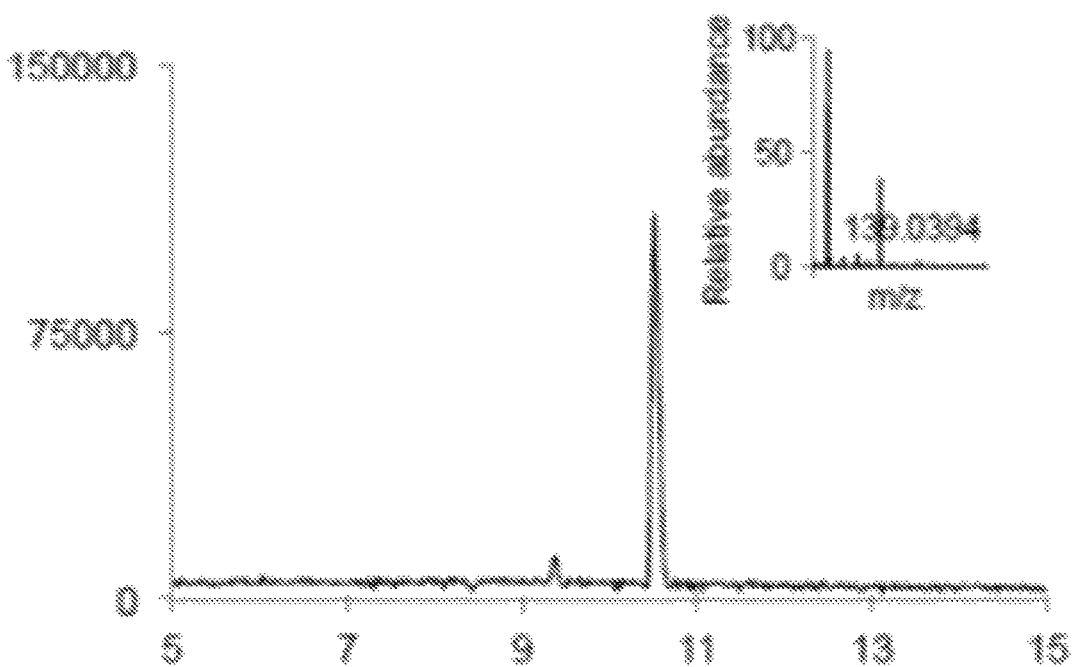
Figure 19C:
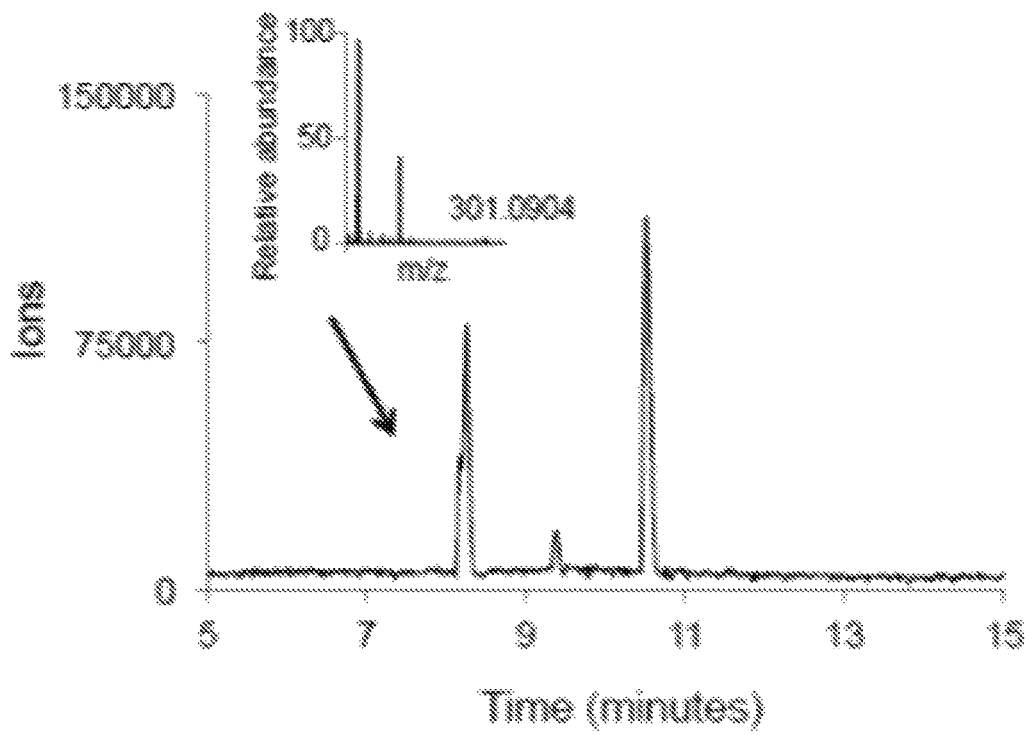
Figure 19D:
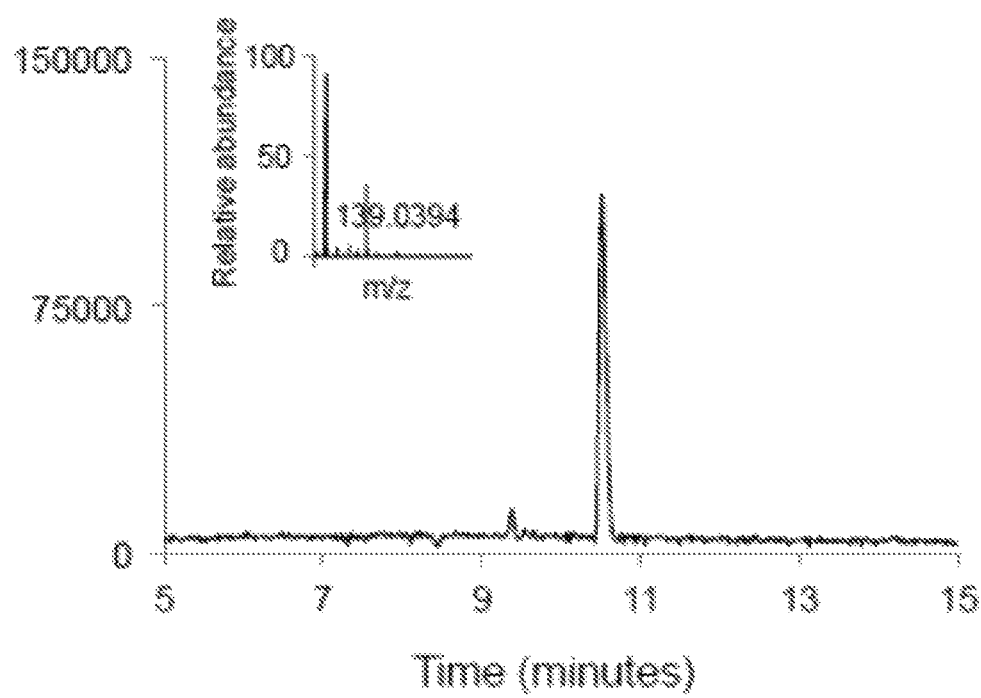
Figure 20A:
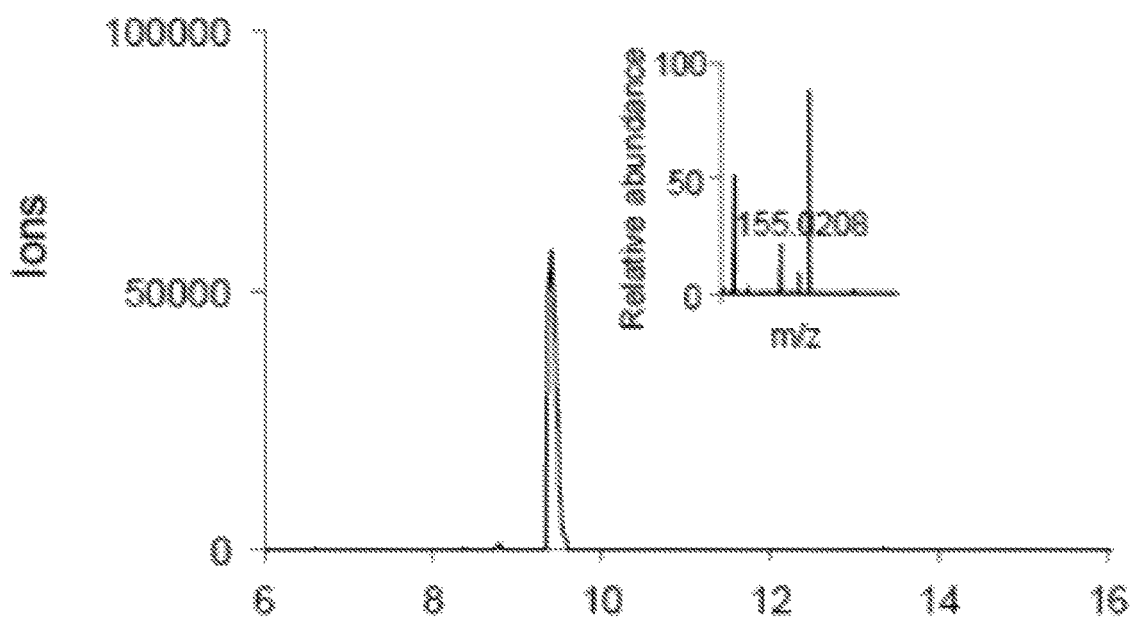
FIG. 20A-FIG. 20D. LC-ESI-MS analysis of 3,4-dihydroxybenzoic acid and 3,4-dihydroxybenzoic acid glucosides prepared by the OleD, GT05, or GT06-catalyzed glucosylation reactions. A. Reaction of OleD with 3,4-dihydroxybenzoic acid. Unreacted 3,4-dihydroxybenzoic acid elutes at 9.36 minutes and has a molecular ion [M+H]+ at m/z 155.02, representing 3,4-dihydroxybenzoic acid. B. Reaction of GT05 with 3,4-hydroxybenzoic acid. Unreacted 3,4-hydroxybenzoic acid elutes at 9.36 minutes and has a molecular ion [M+H]+ at m/z 155.02. GT-catalyzed product elutes at 8.80 minutes and has a molecular ion [M+H]+ at m/z 317.09, representing the 3,4-dihydroxybenzoic acid glucoside. C. Reaction of GT06 with 3,4-dihydroxybenzoic acid. Unreacted 3,4-dihydroxybenzoic acid elutes at 9.36 minutes and has a molecular ion [M+H]+ at m/z 155.02. GT-catalyzed product elutes at 8.15 minutes and has a molecular ion [M+H]+ at m/z 317.09, representing the 3,4-dihydroxybenzoic acid glucoside. D. 3,4-dihydroxybenzoic acid pre-GT-catalyzed glucosylation reaction. Starting material elutes at 9.36 minutes and has a molecular ion [M+H]+ at m/z 155.02, representing 3,4-dihydroxybenzoic acid. Molecular mass of the molecular ion [M+H]+ of 3,4-dihydroxybenzoic acid glucosides equals the sum of 3,4-dihydroxybenzoic acid and one molecule of glucose with a gain of a hydrogen.
Figure 20B:
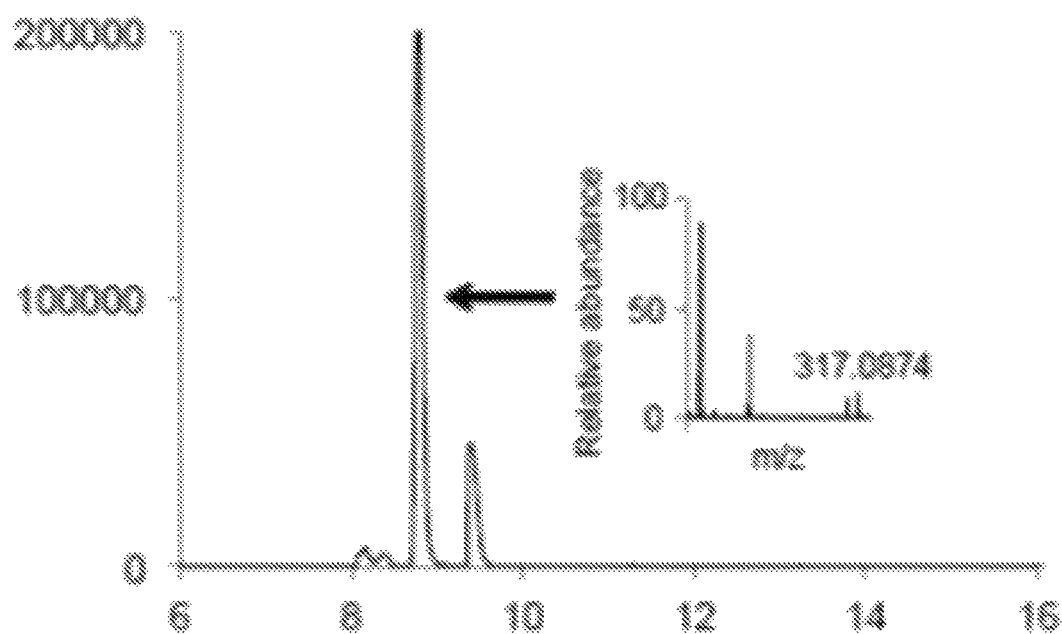
Figure 20C:
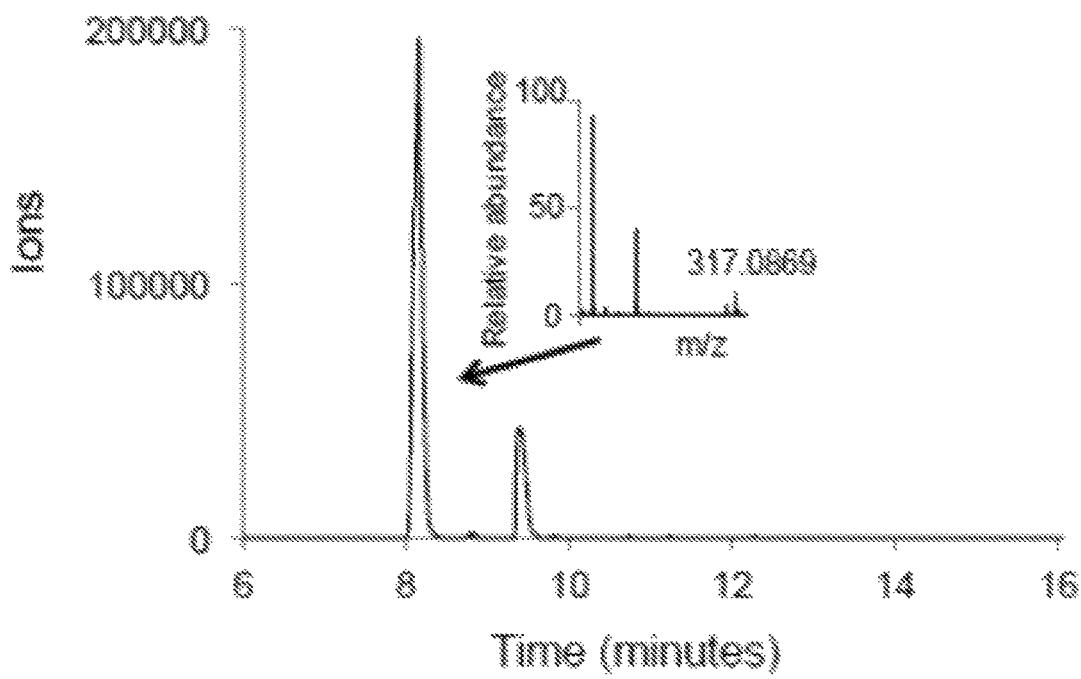
Figure 20D:
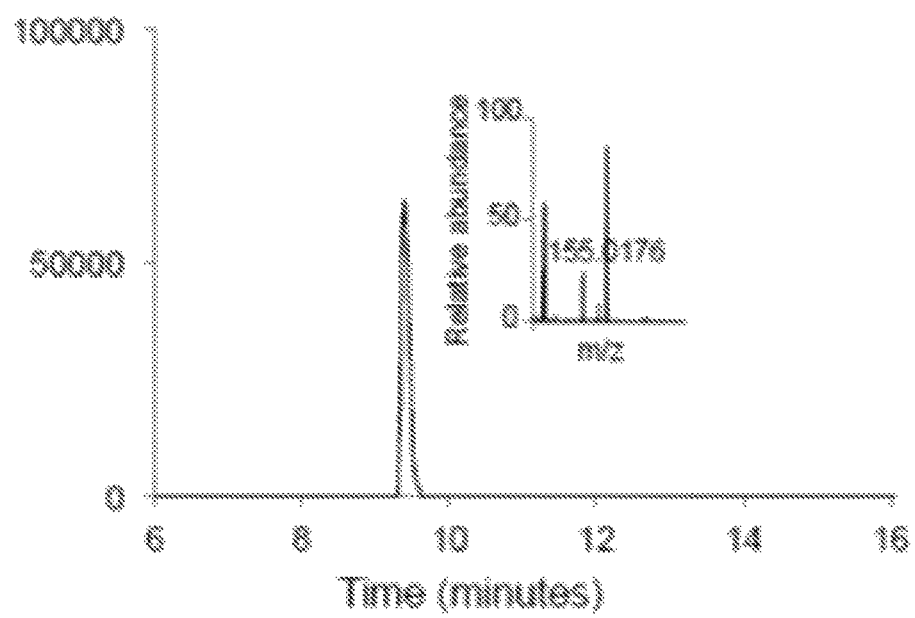

Further verification of the assay's capability was shown when OleD was tested against other known OleD substrates (FIG. 4Ai) (Williams, et al., (2007) *Nat Chem Biol.* 3, 657-662; Choi, et al., (2012) *Biotechnol Lett.*, 34:499-505; Yang, et al., (2005) *JACS Commun.*, 127:9336-9337). Using the previously described qPCR DLEnCA protocol, DNA encoding OleD was incubated with kaempferol (I), apigenin (II), 4-methylumbelliferone (III), 7-hydroxycoumarin-4-acetic acid (IV), and 7-hydroxycoumarin-3-carboxylic acid (V). Results to this assay are shown in FIG. 4B as percent DNA recovery. A threshold of activity can be seen when one takes into consideration the lower activity rate of OleD against substrates (II) and (III). In previous studies, OleD was reported to glucosylate these substrates at a slower rate or with less efficiency than with (I) (Williams, et al., (2007) *Nat Chem Biol.* 3, 657-662; Choi, et al., (2012) *Biotechnol Lett.*, 34:499-505; Yang, et al., (2005) *JACS Commun.*, 127:9336-9337). Consistent with earlier observations, while LCMS analysis identified the chemicals as substrates (FIGS. 7-8), the assay was only able to recover 42% and 60% of the probe DNA respectively. Other substrates tested include (IV) and (V). Both were found in previous publications to be very weak substrates of OleD (Williams, et al., (2007) *Nat Chem Biol.* 3, 657-662; Choi, et al., (2012) *Biotechnol Lett.*, 34:499-505; Yang, et al., (2005) *JACS* Commun., 127:9336-9337). This observation was verified using both qPCR DLEnCA (82% and 97% recovery of probe respectively) and LCMS (FIG. 9-10). From this it was concluded qPCR DLEnCA could be used to follow an enzymatic reaction.

Figure 4C:
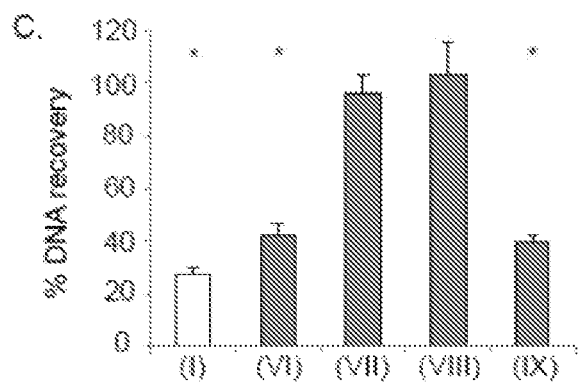
Figure 6A:
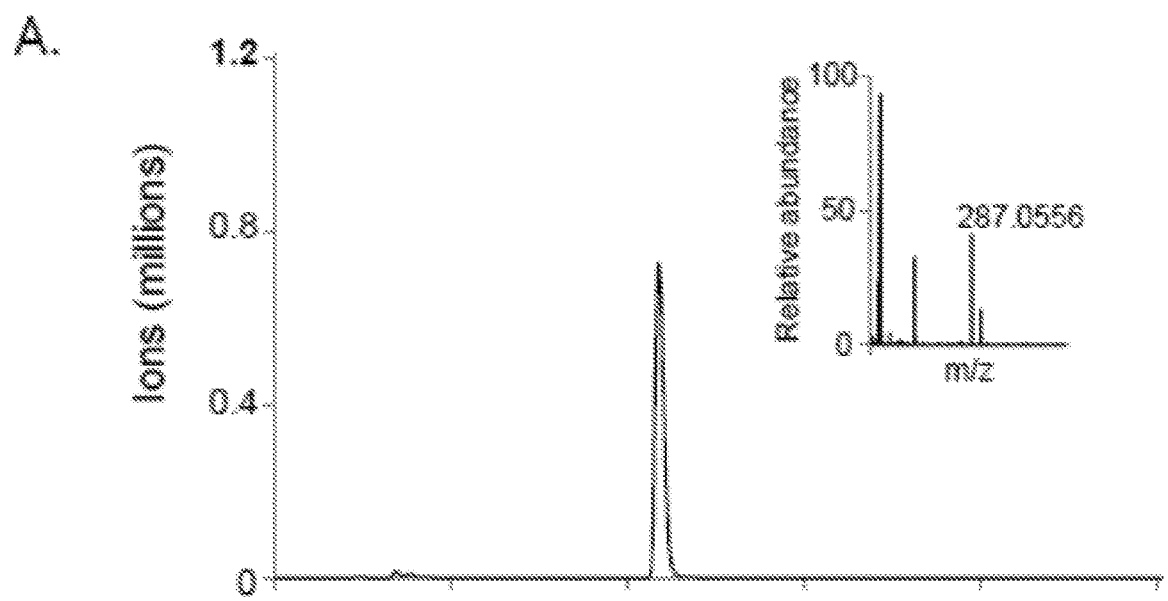
FIG. 6A-FIG. 6B. LC-ESI-MS analysis of kaempferol and kaempferol glucosides prepared by the OleD-catalyzed glucosylation reaction. A. Starting material elutes at 14.35 minutes and has a molecular ion [M+H]+ at m/z 287.06, representing kaempferol. B. Reaction of OleD with kaempferol. Unreacted kaempferol elutes at 14.35 minutes. GT-catalyzed products elute at 11.32 and 11.39 minutes. Both have a molecular ion [M+H]+ at m/z 449.11, representing the kaempferol glucoside. Fragment at m/z 287.06 represents kaempferol. Molecular mass of the molecular ion [M+H]+ of kaempferol glucoside equals the sum of kaempferol and one molecule of glucose with a gain of a hydrogen.
Figure 6B:
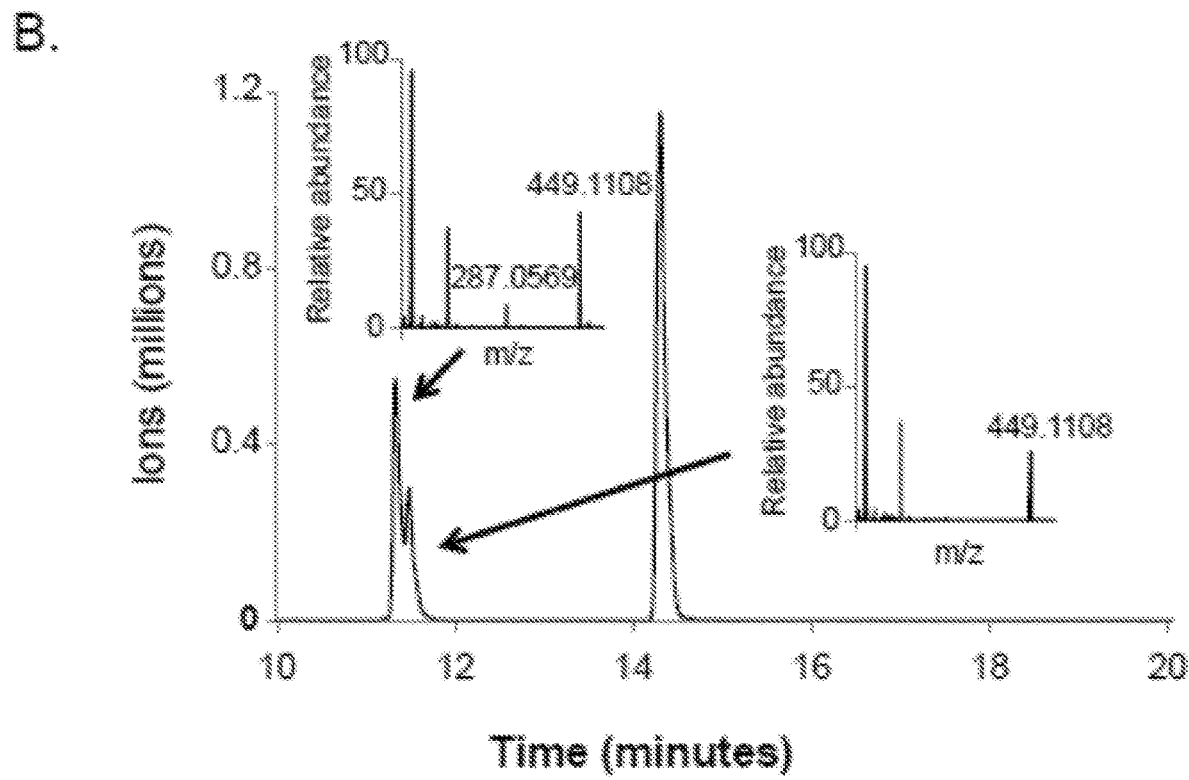

During the initial verification of the assay, it was observed that two predominant glucosides were produced when kaempferol was incubated with OleD (FIG. 6). Kaempferol has four hydroxyl-motifs amenable for glucosylation in its structure. To help identify which hydroxy groups were being preferentially glucosylated, qPCR DLEnCA was employed using four flavones as substrates for the enzyme (FIG. 4Aii). As shown in FIG. 4C, 3-hydroxyflavone (VI) and 7-hydroxyflavone (IX) resulted in a significant loss in protection of the DNA probe, at 42% and 39% respectively. This was not the case with 4-hydroxyflavone (VII) and 5-hydroxyflavone (VIII). Flavone glucosylation was also verified by LCMS (FIGS. 11-14). It was concluded that the 3-hydroxy and the 7-hydroxy positions of kaempferol were the preferential glucosylation motifs of OleD. This observation was verified by use of glucoside standards (Sigma Aldrich) on LCMS. As shown in FIG. 15, the purchased kaempferol-3-glucoside standard eluted from LCMS at the same time as the first product peak in the experimental reaction, while the elution time of the kaempferol-7-glucoside standard was identical to the second peak.

Figure 4D:
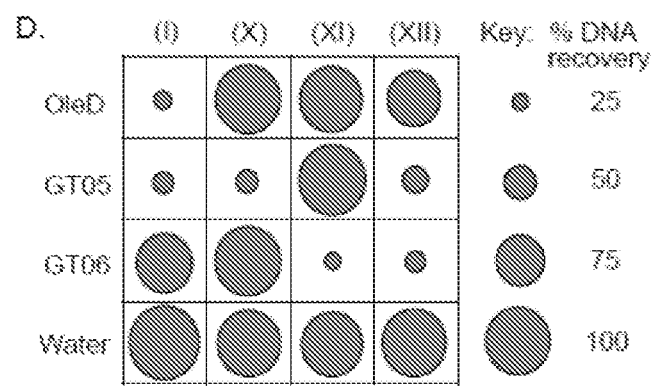

As a final verification of the assays generality to the glucosyltransferase enzyme class, qPCR DLEnCA was used to test the activity of two *Arabidopsis* glucosyltransferases against their known preferred substrates (FIG. 4Aiii) (Lim, et al., (2002) *JBC*, 277:586-592; Messner, et al., (2003) *Planta.*, 217:138-146). GT05 (71B2) and GT06 (89B1) were cloned from cDNA obtained from *Arabidopsis thaliana* and used as starting material for the cell-free transcription/translation assays; OleD was also used for verification (FIG. 4D). As expected, OleD only showed activity with (I). This was identified by qPCR DLEnCA and verified with LCMS (FIG. 4D; FIGS. 16-20). GT05 was shown to not only have activity with 3-hydroxybenzoic acid (X) (33% recovery) and 3,4-dihydroxybenzoic acid (XII) (40% recovery), but was also found to interact with (I) (32% recovery) (FIG. 4D; FIGS. 16-20). Finally, as expected, GT06 was found to interact with 4-hydroxybenzoic acid (XI) (25% recovery) and (XII) (30% recovery) (FIG. 4D; FIGS. 16-20). From this it was concluded that qPCR DLEnCA was able to follow glucosyltransferase activities from diverse sources.

The invention described herein has a number of advantages over existing methods for the biochemical analysis of enzymes, e.g., glucosyltransferases. For example, DLEnCA alleviates the need to purify proteins or use time-consuming analytics. At the same time, the speed of the assay allows for a quick screen of either substrate specificities of an enzyme of interest or testing different enzymes for activity on a given substrate. For example, in the course of a single day the glucosylation-specificity of OleD can be mapped to the 3- and 7-hydroxy-motifs found on kaempferol. This mapping can later be verified using various techniques, e.g., LCMS and glucoside standards. To our knowledge, this is the first time the glucosyl-specificity of OleD and kaempferol has been discussed.

The ability to link an enzymatic reaction to a DNA modification is a significant advantage for DLEnCA. This advantage permits a researcher to couple a protein's activity to its encoding DNA, allowing for the potential use of multiplexed or mixed enzyme libraries in a single assay. With simple modifications, this assay can probe the substrate specificities of many enzymatic classes, as long as the cofactor utilized by the enzymes of interest can also be used to modify DNA. Additionally, the throughput of the assay could be further improved by coupling the assay with liquid handling robotics and/or emulsion technologies, and next generation sequencing techniques.

In exemplary embodiments, DLEnCA incorporates the use of cell-free transcription/translation systems. While this is beneficial, given a researcher will have the ability to study the enzymatic activities of toxic or chronically-insoluble proteins without the need for protein purification and/or concentration, some issues of note should be mentioned. In an exemplary embodiment, the methods of the invention use purified protein as a starting material. Though this diminishes DLEnCA's advantage of speed, it still circumvents the need for LCMS. Finally, poor substrate purity could result in false positive signals caused by reactions of contaminating compounds. However, because the assay is stoichiometric, the contaminant would need to be present in excess of ~10 µM to see such false signals.

In summary, DNA-Linked Enzyme-Coupled Assays can monitor the reactions of known or unknown enzymes with diverse substrates. Though the embodiments presented herein are specific to monitoring the reactions of glucosyltransferases, the present invention works by monitoring consumption of cofactors; therefore additional variations on the assay are of use to probe comsumption of other cofactors, e.g., NAD+, SAM, or other nucleotide-sugar consuming reactions. A major challenge in screening large numbers of genes for function has been the ability to connect genotype with phenotype. By linking enzymatic function to chemical modifications of DNA, DLEnCA provides the solution for a large class of genes relevant to constructing microbial chemical factories.

Example 2

S-Adenosyl-L-Methionine (SAM) Coupled to DMTase

Figure 26A:
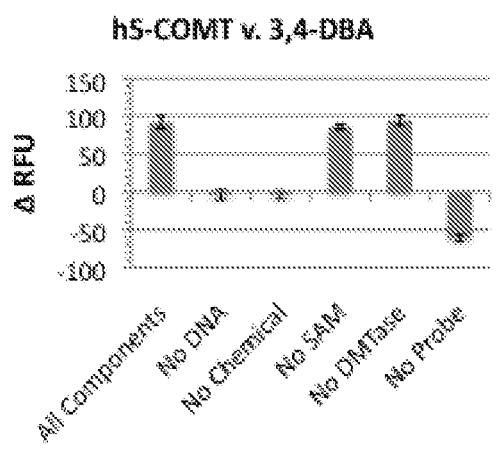
FIG. 26A-FIG. 26B. Dropout controls for DLEnCA assays monitoring methylation reactions. Plots represent RFU values after 3 hours of digestion. All RFU values are referenced against the No Restriction Enzyme control. Error-bars represent the propagated standard deviation.
Figure 26B:
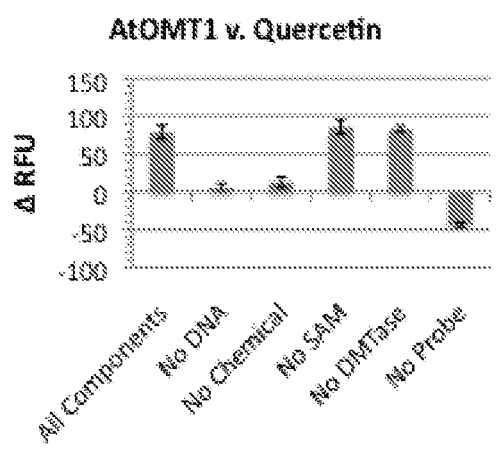

In addition to glycosylation reactions, DLEnCA assays can monitor methylation reactions through the consumption of SAM. Depletion of SAM prevents a DNA methyltransferse (DMTase) from modifying the DNA. The probe DNA for monitoring SAM consumption does not contain special bases. It only needs to encode the recognition sequence for a sequence-specific methyltransferase. Methylation of the DNA blocks cleavage by the cognate restriction enzyme. The EcoRI methyltransferase was employed as the DMTase which blocks digestion by EcoRI restriction endonuclease. The assay was tested for monitoring the methylation of 3,4-dihydroxybenzoic acid [3,4-DBA] and Quercetin by the enzymes human S-COMT and *Arabidopsis* AtOMT1, respectively. The assay involved sequential addition of (1) DNA in cell-free TxT1 mix, (2) Chemical and SAM in 80% DMSO, (3) Probe and DMTase, and lastly (4) EcoRI. Between each reagent addition there is a 3 hour incubation step at 37° C., except in the case of incubation with (2) where the temperature used was chosen based on previous literature comments about optimal enzyme activity. After addition of the EcoRI, fluorescence was monitored using a fluorescent plate-reader. Final amounts of all added reagents were: 50 µg of DNA encoding the enzyme, 1 mM chemical substrate, 10 µM S-Adenosyl methionine [SAM] cofactor, 8% DMSO, 5 pmol probe, 40 Units M.EcoRI, and 20 Units EcoRI. Total reaction volume at end of additions was 11 µL. To demonstrate the assay, we repeated the same series of dropout controls as in the Glucosyltransferase assay. As seen in FIG. 26A-B, the SAM variant of DLEnCA works and has superior signal-to-noise than does the UDP-glucose variant of the assay.

Monitoring of Methyltransferase Enzyme Kinetics

That enzyme kinetics can be followed by DLEnCA was determined. The methylation of two substrates of AtOMT1 previously characterized: Quercetin [Qer] and Luteolin [Lut] was monitored and showed approximately an order of magnitude difference in kinetics.

Figure 27A:
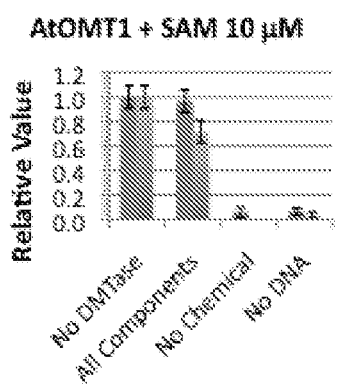
FIG. 27A-FIG. 27C. Running AtOMT1 against Quercetin (blue bars) and, the less preferred, Luteolin (red bars). Values represent the normalized RFUs taken after 3 hours of digestion of the "kinetic-DLEnCA" runs at different SAM concentrations. Error-bars represent the propagated standard deviation. Of particular relevance is the difference seen in the "All Component" runs.
Figure 27B:
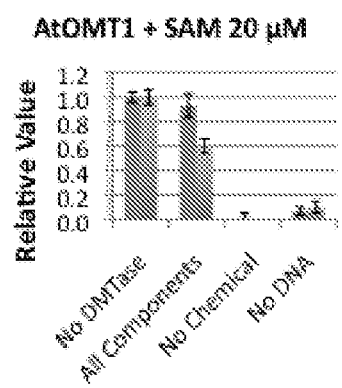
Figure 27C:
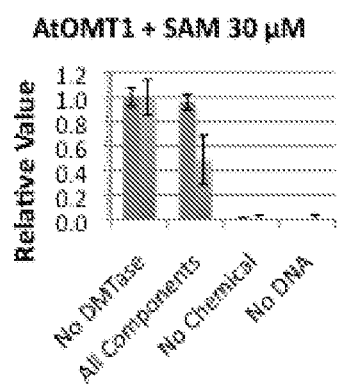

The experiments were conducted similar to the standard DLEnCA protocol with the exception that the first incubation in the TxT1 mix was conducted for only 1 hour (with SAM at either 10 µM or 30 µM already pre-added), and the incubation with chemicals limited to 30 minutes. Based on the results illustrated in FIG. 27A-C, it is apparent that condensing incubation times and titration of the cofactor concentration can be used to identify coarse differences in enzyme activity towards different chemicals.

Monitoring of Biosynthetic Pathways with a Terminal Methylation Step

An exemplary use of DLEnCA is the monitoring of entire biosynthetic pathways for high-throughput prototyping applications including directed evolution and combinatorial experiments. If a sequence of reactions ends with a step that consumes a cofactor detectable by DLEnCA, then a lack of conversion at any previous step will result in a loss of cofactor depletion. Thus, a positive DLEnCA signal confirms all earlier steps in the pathway. The assay was tested on a two-step pathway whose last step is a methylation reaction using the FRET variant of the methyltransferase DLEnCA assay (FIG. 28A-B). When all components are provided, the cofactor is consumed, the DNA is unmethylated, and a signal is observed. When any single component is omitted, the signal is lost confirming that each individual component of the pathway is necessary for it to occur.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES (1) Kim, D. Y.; Rha, E.; Choi, S.-L.; Song, J. J.; Hong, S.-P.; Sung, M.-H.; Lee, S.-G. (2007) Development of bioreactor system for L-tyrosine synthesis using thermostable tyrosine phenol-lyase. *J. Microb. Biotechnol.* 17, 116-122.
(2) Williams, G. J.; Zhang, C.; Thorson, J. S. (2007) Expanding the promiscuity of a natural-product glycosyltransferase by directed evolution. *Nat Chem Biol.* 3, 657-662.
(3) Volpato, G.; Rodrigues, R. C.; Fernandez-Lafuente, R. (2010) Use of enzymes in the production of semi-synthetic penicillins and cephalosporins: Drawbacks and perspectives. *Curr. Med. Chem.* 17, 3855-3873.
(4) Meyer, D.; Walter, L.; Kolter, G.; Pohl, M.; Muller, M.; Tittmann, K. (2011) Conversion of pyruvate decarboxylase into an enantioselective carboligase with biosynthetic potential. *JACS.* 133, 3609-3616.
(5) Seelig, B.; Szostak, J. W. (2007) Selection and evolution of enzymes from a partially randomized non-catalytic scaffold. *Nature.* 448, 828-831.
(6) Cisneros, J. A.; Bjorklund, E.; Gonzalez-Gil, I.; Hu, Y.; Canales, A.; Medrano, F. J.; Romero, A.; Ortega-Gutierrez, S.; Fowler, C. J.; Lopez-Rodriguez, M. L. (2012). Structure-activity relationship of a new series of reversible dual monoacylglycerol lipase/fatty acid amide hydrolase inhibitors. *J. Med. Chem.* 55, 824-836.
(7) Hibbert, E. G.; Senussi, T.; Smith, M. E.; Costelloe, S. J.; Ward, J. M.; Hailes, H. C.; Dalby, P. A. (2008) Directed evolution of transketolase substrate specificity towards an aliphatic aldehyde. *J. Biotechnol.* 134, 240-245.
(8) Kubota, T.; Tanaka, Y.; Hiraga, K.; Inui, M.; Yukawa, H. (2013) Characterization of shikimate dehydrogenase homologues of *Corynebacterium glutamicum*. *Appl. Microbiol. Biotechnol.* 97, 8139-8149.
(9) Canganella, F.; Andrade, C. M.; Antranikian, G. (1994) Characterization of amylolytic and pullulytic enzymes from thermophilic archaea and from a new *Fervidobacterium* species. *Appl. Microbiol. Biotechnol.* 42, 239-245.
(10) Brissos, V.; Eggert, T.; Babral, J. M. S.; Jaeger, K. E. (2008) Improving activity and stability of cutinase towards the anionic detergent AOT by complete saturation mutagenesis. *Protein Eng. Des. Sel.* 21, 387-393.

(11) Miyazaki, K.; Arnold, F. H. (1999) Exploring non-natural evolutionary pathways by saturated mutagenesis: rapid improvement of protein function. *J. Mol. Evol.* 49, 716-720.

(12) Reetz, M. T.; Prasad, S.; Carballeira, J. D.; Gumulya, Y.; Bocola, M. (2010) Iterative saturation mutagenesis accelerates laboratory evolution of enzyme stereoselectivity: rigorous comparison with traditional methods. *JACS.* 132, 9144-9152.

(13) Zaccolo, M.; Gherardi, E. (1999) The effect of high-frequency random mutagenesis on in vitro protein evolution: a study on TEM-1 beta-lactamase. *J. Mol. Biol.* 285, 775-783.

(14) Schomburg, I.; Chang, A.; Placzek, S.; Solingen, C.; Rother, M.; Lang, M.; Munaretto, C.; Ulas, S.; Stelzer, M.; Grote, A.; Scheer, M.; Schomburg, D. (2013) BRENDA in 2013: integrated reactions, kinetic data, enzyme function data, improved disease classification: new options and contents in BRENDA. *Nucleic Acids Res.* 41, D764-D772.

(15) Henne, A.; Daniel, R.; Schmitz, R. A.; Gottschalk, G. (1999) Construction of environmental DNA libraries in *Escherichia coli* and screening for the presence of genes conferring utilization of 4-hydroxybutyrate. *Appl. and Environ. Microbiol.* 65, 3901-3907.

(16) Qin, J.; Li, R.; Raes, J.; Arumugam, M.; Burgdorf, K. S.; Manichanh, C.; Nielsen, R.; Pons, N.; Levenez, F.; Yamada, T.; Mende, D. R.; Li, J.; Xu, J.; Li, S.; Li, D.; Cao, J.; Wang, B.; Liang, H.; Zheng, H.; Wie, Y.; Tap, J.; Lepage, P.; Bertalan, M.; Batto, J.-M.; Hansen, T.; Le Paslier, D.; Linneberg, A.; Nielsen, H. B.; Pelletier, E.; Renault, P.; Sicheritz-Ponten, T.; Turner, K.; Zhu, H.; Yu, C.; Li, S.; Jian, M.; Zhou, Y.; Li, Y.; Zhang, X.; Li, S.; Qin, N.; Yang, H.; Wang, H.; Brunak, S.; Dore, J.; Guarner, F.; Kristiansen, K.; Pedersen, O.; Parkhill, J.; Weissenbach, J. (2010) A human gut microbial gene catalogue established by metagenomic sequencing. *Nature.* 464, 59-65.

(17) Venter, J. C.; Remington, K.; Heidelverg, J. F.; Halpern, A. L.; Rusch, D.; Eisen, J. A.; Wu, D.; Paulsen, I.; Nelson, K.; Nelson, W.; Fouts, D. E.; Levy, S.; Knap, A. H.; Lomas, M. W.; Nealson, K.; White, O.; Peterson, J.; Hoffman, J.; Parsons, R.; Baden-Tillson, H.; Pfannkoch, C.; Rogers, Y.-H.; Smith, H. O. (2004) Environmental genome shotgun sequencing of the Sargasso Sea. *Science.* 304, 66-74.

(18) Borovkov, A. Y.; Loskutov, A. V.; Robida, M. D.; Day, K. M.; Cano, J. A.; Olson, T. L.; Patel, H.; Brown, K.; Hunter, P. D.; Sykes, K. F. (2010) High-quality gene assembly directly from unpurified mixtures of microarray-synthesized oligonucleotides. *Nucleic acids research.* 38, e180-e180.

(19) Kosuri, S.; Eroshenko, N.; LeProust, E. M.; Super, M.; Way, J.; Li, J. B.; Church, G. M. (2010) Scalable gene synthesis by selective amplification of DNA pools from high-fidelity microchips. *Nature Biotech.* 28, 1295-1299.

(20) Quan, J.; Saaem, I.; Tang, N.; Ma, S.; Negre, N.; Gong, H.; White, K. P.; Tian, J. (2011) Parallel on-chip gene synthesis and application to optimization of protein expression. *Nature Biotech.* 29, 449-452.

(21) Mardis, E. R. (2008) Next-generation DNA sequencing methods. *Annual Review of Genomics and Human Genetics.* 9, 387-402.

(22) Shendure, J.; Ji, H. (2008) Next-Generation DNA Sequencing. *Nature Biotech.* 26, 1135-1145.

(23) Kinney, S. M.; Chin, H. G.; Vaisvilla, R.; Bitinaite, J.; Zheng, Y.; Esteve, P. O.; Feng, S.; Stroud, H.; Jacobson, S. E.; Pradhan, S. (2011) Tissue-specific distribution and dynamic changes of 5-hydroxymethylcytosine in mammalian genomes. *J. Biol. Chem.* 286, 24685-24693.

(24) Laird, P. W. (2010) Principles and challenges of genome-wide DNA methylation analysis. *Nature Reviews Genetics.* 11, 191-203.

(25) Terragni, J.; Bitinaite, J.; Zheng, Y.; Pradhan, S. (2012) Biochemical Characterization of Recombinant β-Glucosyltransferase and Analysis of Global 5-Hydroxymethylcytosine in Unique Genomes. *Biochemistry.* 51, 1009-1019.

(26) Morera, S.; Imberty, A.; Aschke-Sonnenborn, U.; Ruger, W.; Freemont, P. S. (1999) T4 phage beta-glucosyltransferase: substrate binding and proposed catalytic mechanism. *J. Mol. Biol.* 292, 717-730.

(27) Robertson, A. B.; Dahl, J. A.; Vagbo, C. B.; Tripathi, P.; Krokan, H. E.; Klungland, A. (2011) A novel method for the efficient and selective identification of 5-hydroxymethylcytosine in genomic DNA. *Nucleic Acids Res.* 39, e55.

(28) Szwagierczak, A.; Bultmann, S.; Schmidt, C. S.; Spada, F.; Leonhardt, H. (2010) Sensitive enzymatic quantification of 5-hydroxymethylcytosine in genomic DNA. *Nucleic Acids Res.* 38, e181.

(29) Huang, Y.; Pastor, W. A.; Shen, Y.; Tahiliani, M.; Liu, D. R.; Rao, A. (2010) The behavior of 5-hydroxymethylcytosine n Bisulfite sequencing. *PLoS One.* 5, e8888.

(30) Jin, S.-G.; Kadam, S.; Pfeifer, G. P. (2010) Examination of the specificity of DNA methylation profiling techniques towards 5-methylcytosine and 5-hydroxymethylcytosine. *Nucleic Acids Res.* 38, e125.

(31) Xu, Y.; et al. (2011) Genome-wide regulation of 5hmC, 5mC, and gene expression by Tet1 hydroxylase in mouse embryonic stem cells. *Mol. Cell.* 42, 451-464.

(32) Choi, S. H.; Ryu, M.; Yoon, Y. J.; Kim, D-M.; Lee, E. Y. (2012) Glycosylation of various flavonoids by recombinant oleandomycin glycosyltransferase from *Streptomyces antibioticus* in batch and repeated batch modes. *Biotechnol Lett.* 34, 499-505.

(33) Gantt, R. W.; Peltier-Pain, P.; Thorson, J. S. Enzymatic methods for glycol (diversification/randomization) of drugs and small molecules. (2011) Nat. Prod. Rep. 28, 1811-1853.

(34) Gantt, R. W.; Goff, R. D.; Williams, G. J.; Thorson, J. S. (2008) Probing the aglycon promiscuity of an engineered glycosyltransferase. *Angew. Chem., Int. Ed.* 47, 8889-8892.

(35) Yang, M.; Proctor, M.; Bolam, D.; Errey, J.; Field, R.; Gilbert, H.; Davis, B. (2005) Probing the Breadth of Macrolide Glycosyltransferases: In Vitro remodeling of a polyketide antibiotic creates active bacterial uptake and enhances potency. *JACS Commun.* 127, 9336-9337.

(36) Lim, E. K.; Doucet, C.; Li, Y.; Elias, L.; Worrall, D.; Spencer, S.; Ross, J.; Bowles, D. (2002) The Activity of *Arabidopsis* Glycosyltransferases toward Salicylic Acid, 4-Hydroxybenzoic Acid, and Other Benzoates. *JBC.* 277, 586-592.

(37) Messner, B.; Thylke, O.; Shaffner, A. R. (2003) *Arabidopsis* glucosyltransferase with activities toward both endogenous and zenobiotic substrates. *Planta.* 217, 138-146.

What is claimed is:

1. An assay for enzyme activity comprising:
    (a) incubating an enzyme preparation comprising the enzyme of interest with at least one cofactor for the enzyme of interest and at least one substrate for the enzyme of interest under conditions sufficient for the enzyme of interest to modify the at least one substrate with a residue derived from the at least one cofactor;
    (b) following the incubating of (a), incubating the enzyme preparation with a polynucleotide preparation comprising the polynucleotide and a second enzyme using the at least one cofactor to modify a nucleic acid of the polynucleotide, wherein the incubating is under conditions sufficient for the second enzyme to modify the nucleic acid of the polynucleotide preparation wherein the polynucleotide preparation is in solution; and
    (c) determining whether the second enzyme modified the polynucleotide.

2. The method according to claim 1, further comprising:
    (d) prior to (a), expressing the enzyme of interest in a cell-free transcription/translation system.

3. The method of claim 1 wherein the enzyme of interest is a glycosyltransferase.

4. The method of claim 1 wherein the enzyme of interest is a glucosyltransferase.

5. The method of claim 1 wherein the modified nucleic acid is cytidine modified with a glycosyl moiety.

6. The method of claim 1 wherein the determining comprises FRET.

7. The method of claim 1 wherein the determining comprises qPCR.

8. The method of claim 1 wherein the determining comprises digesting the modified polynucleotide with at least one restriction enzyme.

9. The method of claim 1 wherein the substrate for the enzyme of interest is a glycosylation substrate.

10. The method of claim 1 wherein the cofactor for the enzyme of interest is a sugar nucleotide.

11. The method of claim 1 wherein the cofactor for the enzyme of interest is S-adenosyl methionine.

12. The method of claim 1 wherein the cofactor for the enzyme of interest is NADH.

13. The method of claim 1 wherein the enzyme of interest is separated from components of the cell free transcription/translation system prior to step (b).

14. The method of claim 1 wherein the enzyme of interest is produced in cell culture and is separated from components of the cell culture prior to step (b).

* * * * *